United States Patent [19]
Fabijanski et al.

[11] Patent Number: 5,426,041
[45] Date of Patent: Jun. 20, 1995

[54] BINARY CRYPTOCYTOTOXIC METHOD OF HYBRID SEED PRODUCTION

[75] Inventors: Steven F. Fabijanski, Gloucester; Paul G. Arinson, Orleans, both of Canada

[73] Assignee: Pioneer Hi-Bred International, Inc., Des Moines, Iowa

[21] Appl. No.: 30,096

[22] Filed: Mar. 22, 1993

Related U.S. Application Data

[63] Continuation of Ser. No. 556,917, Jul. 20, 1990, abandoned.

[51] Int. Cl.$^6$ .................... A01H 1/00; C12N 15/00
[52] U.S. Cl. .................... 435/172.3; 47/58; 47/DIG. 1; 800/205; 935/35; 935/59
[58] Field of Search ............ 800/200, 205; 47/58, 47/DIG. 1; 435/240.4, 240.49, 172.1, 172.3, 172.2

[56] References Cited

FOREIGN PATENT DOCUMENTS

| | | | |
|---|---|---|---|
| 611258 | 6/1991 | Australia | 435/172.3 |
| 0193259 | 9/1986 | European Pat. Off. | C12N 15/00 |
| 0329308 | 8/1989 | European Pat. Off. | 435/172.3 |
| 0412911 | 2/1991 | European Pat. Off. | 435/172.3 |
| WO89/10396 | 11/1989 | WIPO | 800/205 |
| WO90/08828 | 8/1990 | WIPO | 435/172.3 |

OTHER PUBLICATIONS

Sitbon, F. et al., *Phsiol. Plant.*, "Transgenic Tobacco Plants Overproducing IAA Display Abnormal Growth and Development", 79(2)(152): A27, (Jun. 1990).

Budar, F. et al., *Plant Science*, "Introduction and Expression of the Octopine T-DNA Oncogenes in Tobacco Plants and Their Progeny", 46(3): 195–206 (1986).

Howell, S. H. et al., *Science*, "Cloned Cauliflower Mosaic Virus DNA Infects Turnips (*Brassica rapa*)", 208: 1265–1267 (1980).

Goodman, R. M. et al., *J. Gen Virol.*, "Review Artical: Geminiviruses" 54: 9–21 (1981).

Horsch, R. B. et al., *Science*, "A Simple and General Method for Transferring Genes into Plants", 227: 1229–1231 (1985).

Charest, P. J. et al., *Theor. Appl. Genet.*, "*Agrobacterium*-Mediated Transformation of Thin Cell Layer Explants from *Brassica napus* L.", 75: 438–444 (1988).

(List continued on next page.)

*Primary Examiner*—Gary Benzion
*Attorney, Agent, or Firm*—Foley & Lardner

[57] ABSTRACT

The invention relates to a method for the preparation of a seed of a plant comprising crossing a male sterile plant and a second plant which is male fertile, and obtaining seed of said male sterile plant, said male sterile plant and said second plant being selected such that said seed has integrated into its genome a first recombinant DNA molecule having a first DNA sequence which encodes a first gene product and a first promoter which is capable of regulating the expression of said first DNA sequence, and a second recombinant DNA molecule which contains a second DNA sequence which encodes a second gene product and a second promoter which is capable of regulating the expression of said second DNA sequence, one of said first and said second recombinant DNA molecules originating from said male sterile plant and the other of said first and second recombinant molecules originating from said second plant, and said first and second gene products cooperating to selectively interfere with the function and/or development of cells of a plant that are critical to pollen formation and/or function of a plant grown from said seed whereby said plant grown from said seed is substantially male sterile. The invention also relates to a method of producing F1 hybrid seed from a plant regenerated from such seed, a method of producing F2 hybrid seed using plants regenerated from the F1 hybrid seed, the products produced from these methods and their use.

14 Claims, 17 Drawing Sheets

OTHER PUBLICATIONS

DeBlock, M. et al., *Plant Physiol.*, "Transformation of *Brassica napus* and *Brassica oleracea* Using *Agrobacterium tumefaciens* and the Expression of the *bar* and *neo* Genes in the Trans . . . ", 91: 694–701 (1989).

Feldman, K. A. et al., *Plant Science*, "Rapid and Efficient Regeneration of Plants from Explants of *Arabidopsis thaliana*", 47: 63–69 (1986).

Fry, J. et al., *Plant Cell Reports*, "Transformation of *Brassica napus* with *Agrobacterium tumefaciens* Based Vectors", 6: 321–325 (1987).

Moloney, M. M. et al., *Plant Cell Reports*, "High Efficiency Tranformation of *Brassica napus* Using *Agrobacterium* Vectors", 8: 238–242 (1989).

Neuhaus, G. et al., *Theor. Appl. Genet.*, "Transgenic Rapeseed Plants Obtained by the Microinjection of DNA into Microspore-Derived Embryoids", 75: 30–36 (1987).

Guerche, P. et al., *Plant Science*, "Direct Gene Transfer by Electroporation in *Brassica napus*", 52: 111–116 (1987).

Klein, T. M. et al., *Nature.*, "High-Velocity Microprojectiles for Delivering Nucleic Acids into Living Cells", 327: 70–73 (1987).

Barker et al., *Plant Moleulcar Biology*, "Nucleotides Sequence of the T-DNA Region from the *Agrobacterium tumefaciens* Octopine Ti Plasmid pTi15955", 2: 335–350 (1983).

Barton et al. (1987) Plant Physiology vol. 85, 1103–1109.

Albani et al. (1990) Plant Molecular Biology vol. 15: 605–622.

Follin et al. (1985) Mol. Gen. Genet. vol. 201: 178–185.

Watson et al. Molecular Biology of the Gene. 4th Edition. p. 313.

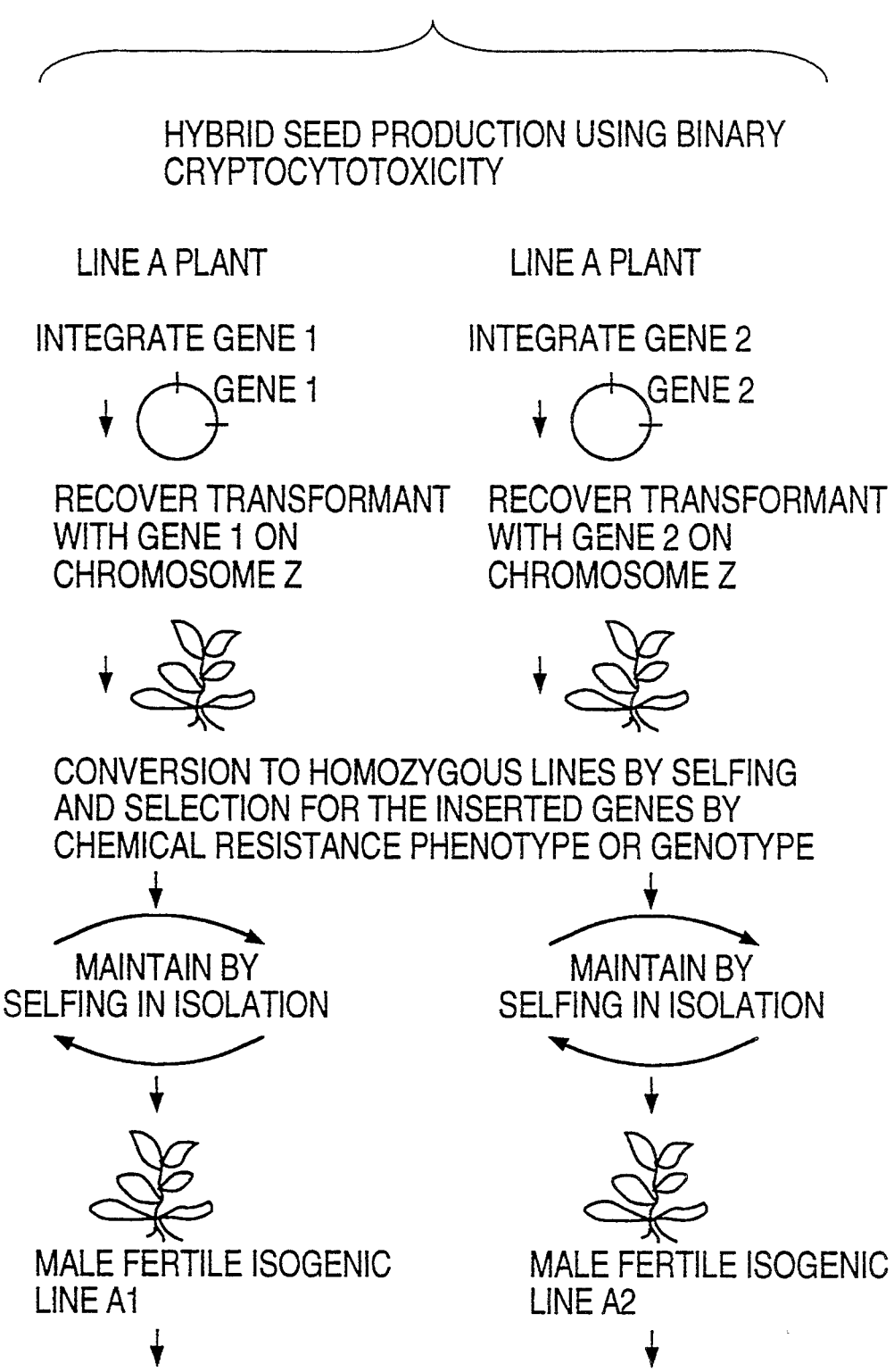

FIG. 2

SEGREGATION OF BINARY CRYPTOCYTOTOXICITY GENES IF BOTH GENES ARE LOCATED ON THE SAME CHROMOSOME OF A CHROMOSOME PAIR IN THE ISOGENIC MALE STERILE LINE

PREPRODUCTION OF MALE STERILE LINE   IAMS—|—IAMS   x   IAMH—|—IAMH

HYBRID SEED PRODUCTION   IAMS—|—IAMH   x   ||

F1 SELFING   IAMS—||   x   ||—IAMH

F2 POTENTIAL GENOTYPES
SELF   IAMS—||   IAMS—|—IAMS (2)   ||
SELF   IAMH—|—IAMH   ||   ||—IAMH (2)
CROSS   IAMS—|—IAMH   ||   ||—IAMH (2)
           MS
CROSS   IAMS—||   IAMS—|—IAMH (2)   ||
                    MS

FIG. 5B

HYBRID SEED PRODUCTION

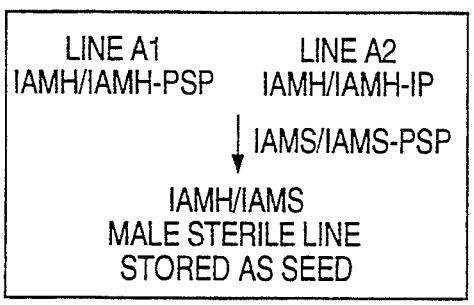

```
    LINE A1            LINE A2
IAMH/IAMH-PSP      IAMH/IAMH-IP
              ↓ IAMS/IAMS-PSP
          IAMH/IAMS
       MALE STERILE LINE
        STORED AS SEED
```
◯ CHEMICAL INDUCER SPRAY

IAMH/IAMS    x    MALE PARENT
MALE STERILE LINE

↓    NO CHEMICAL INDUCER SPRAYING REQUIRED FOR HYBRID SEED PRODUCTION

F1 HYBRID SEED
IAMH/ - OR IAMS/ - GENOTYPE

NOTE PLANTS OF GENOTYPE IAMS/ - ALSO CARRY THE IAMH GENE WHICH IS NOT EXPRESSED IN THE ABSENCE OF THE INDUCER

↓

SALE OF HYBRID SEED FOR PLANTING

↓

GROWTH OF HYBRID PLANT

↓

F2 SEED HARVESTED

PSP = POLLEN SPECIFIC PROMOTER
IP = INDUCIBLE PROMOTER

BINARY CRYPTOCYTOTOXIC METHOD OF HYBRID SEED PRODUCTION

This application is a continuing application of PCT/CA91/00255 which is a continuing application of application Ser. No. 07/556,917, filed Jul. 20, 1990, now abandoned.

FIELD OF THE INVENTION

The invention relates to a process for the preparation of a seed of a plant and to the products produced by the process. The invention also relates to a method of producing F1 hybrid seed from a plant grown from such seed, a method of producing F2 hybrid seed using plants grown from the F1 hybrid seed, the products produced from these methods and their use.

BACKGROUND ART

Production of hybrid seed for commercial sale is a large industry. Hybrid plants grown from hybrid seed benefit from the heterotic effects of crossing two genetically distinct breeding lines with the result that the agronomic performance of the offspring is superior to both parents, typically in vigour, yield, and uniformity. The better performance of hybrid seed varieties compared to open-pollinated varieties makes the hybrid seed more attractive for farmers to plant and thereby commands a premium price in the market place.

Genic male sterility has been utilized in hybrid seed production. Various methods of genic male sterility production and hybrid seed production using male sterile plants are described by the present inventors in published Australian Patent Application Serial No. 611258 and in published PCT Application No. PCT/CA90/00037 by Paladin Hybrids.

Other male sterility systems are disclosed for example in PCT Application No. PCT/WO89/10396 by Plant Genetic Systems.

SUMMARY OF THE INVENTION

The present invention relates to a method for the preparation of a seed of a plant comprising crossing a male sterile plant and a second plant which is male fertile, and obtaining seed of said male sterile plant, said male sterile plant and said second plant being selected such that said seed has integrated into its genome a first recombinant DNA molecule comprising a first DNA sequence which encodes a first gene product and a first promoter which is capable of regulating the expression of said first DNA sequence, and a second recombinant DNA molecule comprising a second DNA sequence which encodes a second gene product and a second promoter which is capable of regulating the expression of said second DNA sequence, one of said first and said second recombinant DNA molecules originating from said male sterile plant and the other of said first and second recombinant molecules originating from said second plant and said first and second gene products cooperating to selectively interfere with the function and/or development of cells of a plant that are critical to pollen formation and/or function of a plant grown from said seed whereby said plant grown from said seed is substantially male sterile.

Preferably, the male sterile plant is obtained by exposing a plant carrying a male sterile trait to a sterility actuating agent.

Preferably, the first recombinant DNA molecule and second recombinant DNA molecule are located on opposite chromatids of the same chromosome pair and most preferably on opposite chromatids of the same chromosome pair at the same genetic locus such that segregation of the first and second recombinant DNA molecules occurs during meiosis and the chance of recombination of the first and second recombinant DNA molecules to the same chromatid during meiotic crossing over is substantially reduced.

Preferably, the first DNA sequence encodes a first gene product which is capable of rendering a non-toxic substance cytotoxic to a cell of a plant which is critical to pollen formation and/or function and said second DNA sequence encodes a second gene product which is said non-toxic substance or encodes a second gene product which is capable of converting a substance endogenous to a plant cell to said non-toxic substance.

In accordance with one embodiment of the invention, the male sterile plant has integrated into its genome a first recombinant DNA molecule comprising a first DNA sequence which encodes a first gene product which is capable of rendering a non-toxic substance cytotoxic to a cell of a plant which is critical to pollen formation and/or function and a first promoter which is capable of regulating the expression of said first DNA sequence, the male sterile plant being produced by exposing a plant having said first recombinant DNA molecule integrated into its genome to said non-toxic substance, and wherein the second plant has integrated into its genome a second recombinant DNA molecule comprising a second DNA sequence which encodes a second gene product which is capable of converting a substance endogenous to a plant cell to the non-toxic substance and a second promoter which is capable of regulating the expression of said second DNA sequence. Preferably, the first DNA sequence encodes indole acetamide hydrolase (IamH), the second DNA sequence encodes indole acetamide synthase (IamS) and the first and second promoters are pollen specific promoters.

In accordance with another embodiment of the invention, the male sterile plant has integrated into its genome a first DNA sequence which encodes a first gene product which is capable of rendering a non-toxic substance cytotoxic to a cell of a plant which is critical to pollen formation and/or function and a first promoter which is capable of regulating the expression of said first DNA sequence, and a second DNA sequence which encodes a second gene product which is said non-toxic substance or encodes a second gene product which is capable of converting a substance endogenous to a plant cell to said non-toxic substance and a second promoter which is capable of regulating the expression of said second DNA sequence, one of said first promoter and said second promoter being an inducible promoter which is capable of being activated by an inducer throughout pollen formation, and the other of said first promoter or said second promoter is a pollen specific promoter, the male sterile plant being produced by exposing a plant having said first DNA sequence and said first promoter and said second DNA sequence and said second promoter integrated into its genome to said inducer, and wherein the second plant has integrated into its genome a pollen specific promoter or a constitutive promoter and either of said first or said second DNA sequences which is regulated by the inducible promoter which is integrated into the genome of said male sterile plant.

In particular, the male sterile plant may have integrated into its genome a first DNA sequence which encodes a first gene product which is capable of rendering a non-toxic substance cytotoxic to a cell of a plant which is critical to pollen formation and/or function regulated by an inducible promoter which is capable of being activated by an inducer throughout pollen formation, and a second DNA sequence which encodes a second gene product which is said non-toxic substance or a second gene product which is capable of converting a substance endogenous to a plant cell to said non-toxic substance regulated by a pollen specific promoter, the male sterile plant being produced by exposing a plant having said first DNA sequence regulated by said inducible promoter and said second DNA sequence regulated by said pollen specific promoter integrated into its genome to said inducer, and wherein the second plant has integrated into its genome said first DNA sequence and a pollen specific promoter or a constitutive promoter.

Preferably, the first DNA sequence encodes IamH, the second DNA sequence encodes IamS. The first DNA sequence may also encode an enzyme which is capable of rendering a protoxin cytotoxic to cells of a plant that are critical to pollen formation and/or function, and the second DNA sequence may encode a protoxin.

The male sterile plant may have integrated into its genome a first DNA sequence which encodes a first gene product which is capable of rendering a non-toxic substance cytotoxic to a cell of a plant which is critical to pollen formation and/or function regulated by a pollen specific promoter, and a second DNA sequence which encodes a second gene product which is said non-toxic substance or a second gene product which is capable of converting a substance endogenous to a plant cell to said non-toxic substance regulated by an inducible promoter which is capable of being activated by an inducer throughout pollen formation, the male sterile plant being produced by exposing a plant having said first DNA sequence regulated by said pollen specific promoter and said second DNA sequence regulated by said inducer integrated into its genome to said inducer, and wherein the second plant has integrated into its genome said second DNA sequence and a pollen specific promoter or a constitutive promoter. Preferably, the first DNA sequence encodes IamH, and the second DNA sequence encodes IamS. The first DNA sequence may also encode an enzyme which is capable of rendering a protoxin cytotoxic to cells of a plant that are critical to pollen formation and/or function, and the second DNA sequence may encode a protoxin.

It will be appreciated that the male sterile plants containing the first and second DNA sequences may have these DNA sequences located on the same recombinant DNA molecule or on different recombinant DNA molecules.

The invention also relates to a method for producing hybrid seed which comprises cross-pollinating a progeny male sterile plant grown from the seed obtained in accordance with the above described method of the invention, with a suitable male fertile plant which does not contain a first recombinant DNA molecule or second recombinant DNA molecule as hereinbefore described, and harvesting hybrid seed from the progeny male sterile plant. For ease of reference, this method of producing hybrid seed is hereinafter referred to as a binary cryptocytotoxic method of hybrid seed production.

A method is also provided for producing F2 plants by outcrossing F1 plants grown from the hybrid seed obtained from the progeny male sterile plant. The seed obtained from the F2 plants may be processed to obtain products such as edible oil, etc. Accordingly, the invention also relates to a method of using the seed of an F2 plant obtained in accordance with the methods of the present invention.

According to a preferred embodiment of the invention, the invention provides a method of producing seed of a male sterile plant, comprising:

(a) producing a male sterile plant line comprising
  (i) introducing into the genome of one or more plant cells of a pollen-producing plant a first recombinant DNA molecule comprising a DNA sequence which encodes a gene product which when produced in a cell of a plant which is critical to pollen formation and/or function is capable of rendering a non-toxic substance cytotoxic to said cell, preferably said non-toxic substance is a chemical agent, most preferably 2-amino-4-methoxy butanoic acid, a non-toxic analog of glucuronic acid, naphthalene acetamide or indole acetamide, preferably said first recombinant DNA molecule comprises a pollen specific promoter and a selection marker gene which encodes a selection gene product which permits the selection of a plant having said first recombinant DNA molecule integrated into its genome;
  (ii) selecting a plant cell into which the first recombinant DNA molecule is stably integrated;
  (iii) regenerating from the selected plant cell a plant which carries the male sterile trait;
  (iv) increasing the number of plants which carry the male sterile trait to produce a plant line having plants carrying the male sterile trait; and
  (v) exposing said plant line to the non-toxic substance to render plants of said plant line male sterile;

(b) cross pollinating plants of the male sterile plant line obtained in (a) above with plants of a second plant line having a genome which stably incorporates a second recombinant DNA molecule comprising a second DNA sequence encoding a second gene product which is capable of converting a substance which is endogenous to cells of said second plant line, to said non-toxic substance; a second promoter capable of regulating the expression of said second DNA sequence, preferably a pollen-specific promoter; preferably said first and second recombinant DNA molecules are incorporated into homologous chromosome pairs, and wherein plants of said second plant line are not capable of rendering the non-toxic substance cytotoxic to cells of plants of said second line which are essential to pollen formation and/or function; and (c) harvesting seed of plants of said male sterile line.

The above mentioned methods of the invention may be used to provide hybridization systems with the following advantages:
(a) Hybrid seed production is not labour intensive and can be achieved on a large scale with commercially acceptable costs;
(b) F1 hybrid seed is fully male fertile;

(c) the population of F2 plants produced by outcrossing F1 plants contain 12.5% male sterile plants, thereby discouraging seed saving or holdback for subsequent planting.

BRIEF DESCRIPTION OF THE DRAWINGS

FIGS. 1A and 1B illustrate an embodiment of the process of the invention using the IamH and IamS genes.

FIG. 2 illustrates the segregation patterns of the IamH and IamS genes in the F1 and F2 populations when the genes are on the same segregation unit.

FIGS. 5A and 5B illustrate an embodiment of the invention using an IamH gene and an IamS gene.

DETAILED DESCRIPTION OF THE INVENTION

Figure 1B:
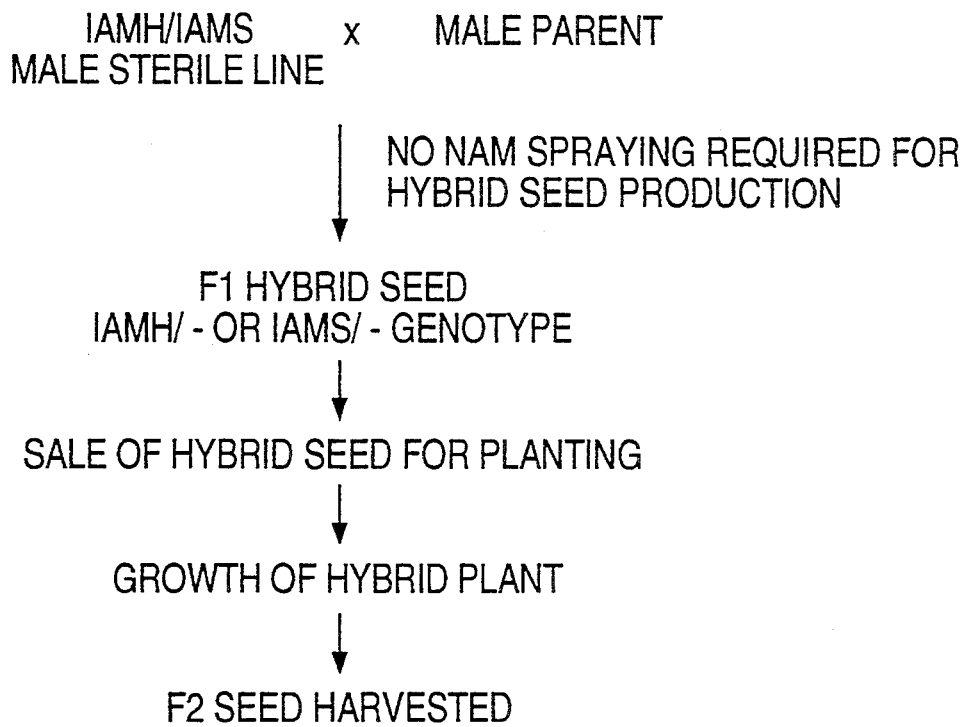

As hereinbefore mentioned the present invention relates to a method for the preparation of a seed of a plant comprising crossing a male sterile plant and a second plant which is male fertile, and obtaining seed of said male sterile plant, said male sterile plant and said second plant being selected such that said seed has integrated into its genome a first recombinant DNA molecule comprising a first DNA sequence which encodes a first gene product and a first promoter which is capable of regulating the expression of said first DNA sequence, and a second recombinant DNA molecule comprising a second DNA sequence which encodes a second gene product and a second promoter which is capable of regulating the expression of said second DNA sequence, one of said first and said second recombinant DNA molecules originating from said male sterile plant and the other of said first and second recombinant molecules originating from said second plant and said first and second gene products cooperating to selectively interfere with the function and/or development of cells of a plant that are critical to pollen formation and/or function of a plant grown from said seed whereby said plant grown from said seed is substantially male sterile.

The invention also relates to a method for producing hybrid seed which comprises cross-pollinating a progeny male sterile plant grown from the seed obtained in accordance with the above described method of the invention, with a suitable male fertile plant which does not contain a first recombinant DNA molecule or second recombinant DNA molecule as hereinbefore described, and harvesting hybrid seed from the progeny male sterile plant.

The methods of the invention described herein may be applicable to any species of pollen-bearing plant, particularly species of plants of the genus Brassica and the family Cruciferae (also known as Brassicaceae), the family Solanacae and more particularly other cultivars of *Brassica napus*. The methods of the invention will be illustrated below with reference to particular embodiments.

As hereinbefore mentioned the first DNA sequence may encode a first gene product which is capable of rendering a non-toxic substance cytotoxic to a cell of a plant which is critical to pollen formation and/or function and the second DNA sequence may encode a second gene product which is the non-toxic substance or encode a second gene product which is capable of converting a substance endogenous to a plant cell to said non-toxic substance.

A cell and/or tissue of a plant which is critical to pollen formation and/or function includes cells and/or tissues that are instrumental in the development or function of pollen, including cells and/or tissues from which pollen develops (e.g. premeiotic and uninucleate microspore cells), cells and/or tissues which form part of the male structure in which pollen develops (e.g. anther, tapetum or filament) and pollen itself.

The first DNA sequence may be any identifiable DNA sequence encoding gene products which are capable of rendering a non-toxic substance cytotoxic to a cell of a plant which is critical to pollen formation and/or function. Examples of such a DNA sequence includes a DNA sequence which encodes indole acetamide hydrolase (IamH) which converts naphthalene acetamide to the plant growth regulator alpha naphthalene acetic acid (NAA) which is toxic to developing pollen grains, or converts indole acetamide to indole acetic acid (IAA) which is a plant growth regulator. One source of the enzyme IamH is the bacterium *Agrobacterium tumefaciens* (Inze, D., et al, 1984, Mol. Gen. Genet. 194:265-74 and Koncz, C. and Schell, J., 1986, 204:383-396 re pPCV 311 plasmid derivative). Another source of an enzyme that is genetically equivalent to IamH is the gene coding for indole acetamide hydrolase from *Pseudomonas savastanoi* (Follin et al. (1985) Mol. Gen. Genet. 201: 178-185).

The first DNA sequence may also encode a gene product which is capable of rendering a non-toxic substance which is a protoxin cytotoxic to a cell of a plant that is critical to pollen formation and/or function. A protoxin has been identified which is inactive against plants but upon enzymatic conversion becomes cytotoxic. (Dotson, S. B. and G. M. Kishore, Isolation of a Dominant Lethal Gene with Potential Uses in Plants In The Genetic Dissection of Plant Cell Processes 1991).

The second DNA sequence may encode a second gene product which is the non-toxic substance or encode a second gene product which converts a substance which is endogenous to a plant cell into the non-toxic substance. For example, a cell may contain a DNA sequence which encodes IamH (which converts indole acetamide to cytotoxic levels of indole acetic acid), and a DNA sequence which encodes IamS. IamS converts tryptophan which is generally endogenous to plant cells, to indole acetamide which in turn is converted by IamH to cytotoxic levels of indole acetic acid. One source of the enzyme IaMS is the T-DNA gene 1 from the bacterium *Agrobacterium tumefaciens* (Inze, D., et al, 1984, Mol. Gen. Genet. 194:265–74). Another source of an enzyme that is functionally equivalent to IamS is the gene coding for tryptophan 2-mono-oxygenase from *Pseudomonas savastanoi* (Follin et al. (1985) Mol. Gen. Genet. 201: 178–185). The second DNA sequence may also encode non-toxic substances such as the above mentioned protoxin.

The promoters used in the methods of the invention may be a pollen specific promoter, an inducible promoter or a constitutive promoter.

A pollen specific promoter is a DNA sequence which regulates the expression of a DNA sequence selectively in the cells/tissues of a plant critical to pollen formation and/or function and/or limits the expression of such a DNA sequence to the period of pollen formation in the plant. Any identifiable pollen specific promoter may be used in the methods of the present invention.

DNA sequences have been isolated from a plant of the species *Brassica napus* ssp *oleifera* cv Westar which are expressed only in microspores and whose expression is essential to microspore function and/or development. A schematic representation of the restriction maps and coding regions of the microspore specific genes identified as L4 (SEQ. NOS. 3 and 4), L10 (SEQ. NOS. 5 and 6), L16 (SEQ. NOS. 1 and 2) and L19 (SEQ. NOS. 7 and 8) have been detailed in published PCT Application No. PCT/CA90/00037. The complete nucleotide sequence of clones L4, and relevant sequences of L10, L16 and L19 have also been detailed in published PCT Application No. PCT/CA90/00037. The construction of vectors containing pollen specific promoters is illustrated in examples 1 to 6 herein and FIGS. 7A to 7E, 8 and 9 herein.

Preferably, the pollen specific promoter is a DNA sequence corresponding to the promoter sequence in the microspore specific genes identified as L4, L10, L16 and L19 above or a functional fragment thereof; or a chimeric promoter sequence containing one or more of a promoter sequence from the microspore specific genes identified as L4, L10, L16 and L19 or portions of such promoter sequences. The L4, L10 and L19 promoter sequences function in tobacco and other plant species. In addition, promoters derived from the L10 gene hybridize to other pollen RNA.

The preferred pollen specific promoters may be used in conjunction with naturally occurring flanking coding or transcribed sequences of the microspore specific genes or with any other coding or transcribed sequence that is critical to pollen formation and/or function.

It may also be desirable to include some intron sequences in the promoter constructs since the inclusion of intron sequences in the coding region may result in enhanced expression and specificity. Thus, it may be advantageous to join the DNA sequences to be expressed to a promoter sequence that contains the first intron and exon sequences of a polypeptide which is unique to cells/tissues of a plant critical to pollen formation and/or function.

Additionally regions of one promoter may be joined to regions from a different promoter in order to obtain the desired promoter activity. Specific examples of chimeric promoter constructs are the chimeric promoters contained in the vectors PAL 1107 (FIG. 7a) and PAL 1106 (FIG. 7b) as outlined in example 1 and in published PCT Application No. PCT/CA90/00037.

The first promoter or the second promoter used in the method of the invention may be an inducible promoter. An inducible promoter is a promoter that is capable of directly or indirectly activating transcription of a DNA sequence in response to an inducer. In the absence of an inducer the DNA sequence will not be transcribed. Typically the protein factor that binds specifically to an inducible promoter to activate transcription is present in an inactive form which is then directly or indirectly converted to the active form by the inducer. The inducer may be a chemical agent such as a protein, metabolite (sugar, alcohol etc.), a growth regulator, herbicide, or a phenolic compound or a physiological stress imposed directly by heat, salt, toxic elements etc. or indirectly through the action of a pathogen or disease agent such as a virus. A plant cell containing an inducible promoter may be exposed to an inducer by externally applying the inducer to the cell such as by spraying, watering, heating, or similar methods. Examples of inducible promoters include the inducible 70 KD heat shock promoter of D. melanogaster (Freeling, M., Bennet, D. C., Maize ADN 1, Ann. Rev. of Genetics 19:297–323) and the alcohol dehydrogenase promoter which is induced by ethanol (Nagao, R. T., et al., Miflin, B. J., Ed. Oxford Surveys of Plant Molecular and Cell Biology, Vol. 3., p. 384–438, Oxford University Press, Oxford 1986). The inducible promoter may be in an induced state throughout pollen formation or at least for a period which corresponds to the transcription of the DNA sequence of the recombinant DNA molecule(s). A promoter that is inducible by a simple chemical is particularly useful since the male sterile plant can easily be maintained by self-pollination when grown in the absence of such a chemical.

It will be appreciated that the term pollen used herein and in particular with reference to the inducible promoter described in the disclosure and claims, includes cells and/or tissues from which pollen develops (e.g. premeiotic and uninucleate microspore cells), cells and/or tissues which form part of the male structure in which pollen develops (e.g. anther, tapetum or filament) and pollen itself.

Another example of an inducible promoter is the chemically inducible gene promoter sequence isolated from a 27 kd subunit of the maize glutathione-S-transferase (GST II) gene. Two of the inducers for this promoter are N,N-diallyl-2,2-dichloroacetamide (common name: dichloramid) or benzyl-2-chloro-4-(trifluoromethyl)-5-thiazolecarboxylate (common name: flurazole). In addition a number of other potential inducers mat be used with this promoter as described in published PCT Application No. PCT/GB90/00110 by ICI.

Another example of an inducible promoter is the light inducible chlorophyll a/b binding protein (CAB) promoter, also described in published PCT Application No. PCT/GB90/00110 by ICI.

Inducible promoters have also been described in published Application No. EP89/103888.7 by Ciba-Geigy. In this application, a number of inducible promoters are identified, including the PR protein genes, especially the tobacco PR protein genes, such as PR-1a, PR-1b, PR-1c, Pr-1, PR-Q, PR-S, the cucumber chitinase gene, and the acidic and basic tobacco beta-1,3-glucanase genes. There are numerous potential inducers for these promoters, as described in Application No. EP89/103888.7.

The first or second promoter may be a constitutive promoter. A constitutive promoter is a promoter that functions in all, many, or a variety of cell types including cells/tissues critical to pollen formation and/or function. An example of such a constitutive promoter is CaMV 35S or preferably HP 101 which has been isolated from Brassica napus, which is particularly described below in reference to FIG. 10.

Figure 10:
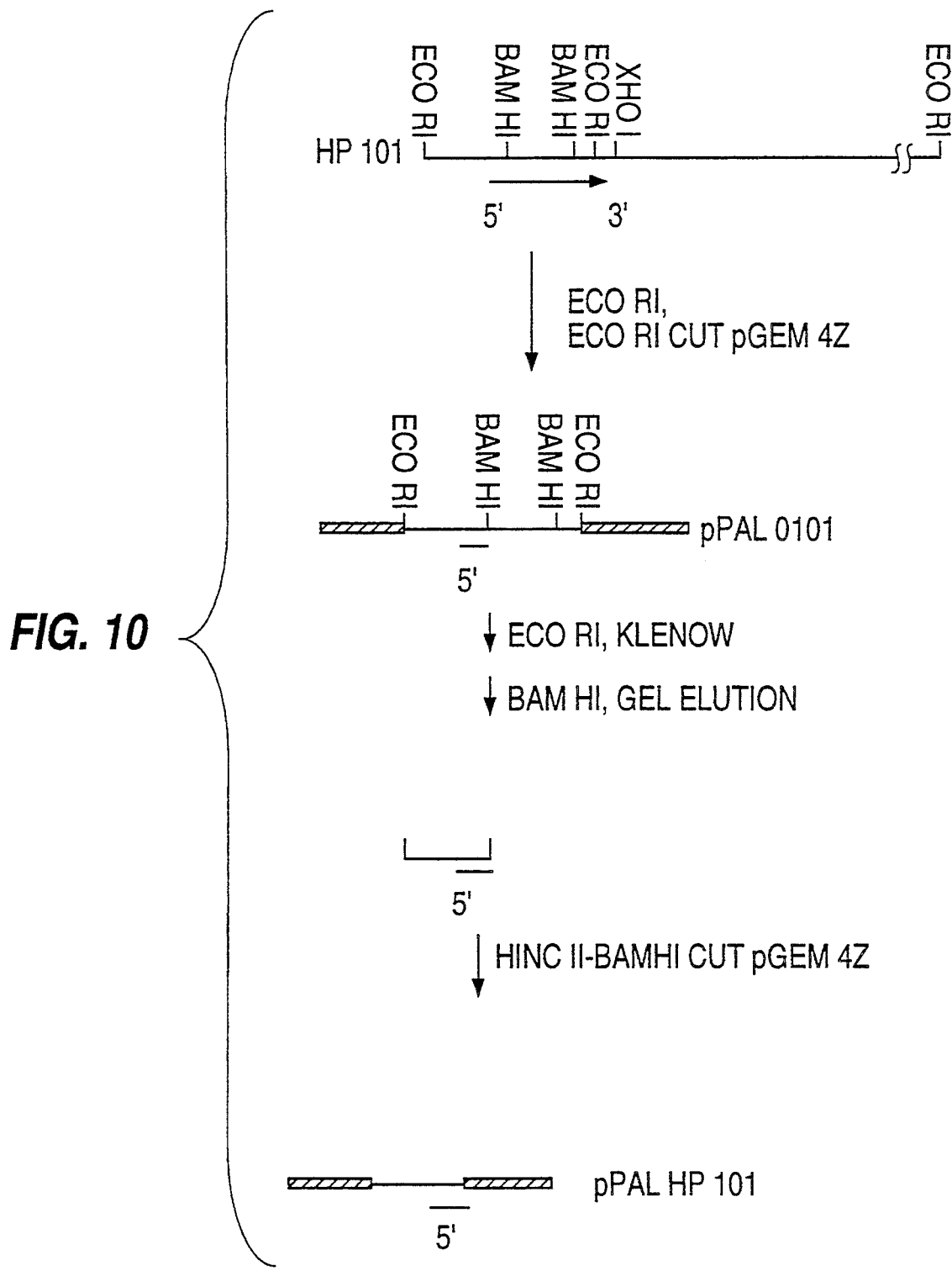
FIG. 10 is a schematic diagram showing the preparation of pPAL0101 and pPALHP101.

The restriction map of a Brassica napus genomic clone (HP 101) deposited Jan. 26, 1990 with the American Type Culture Collection (ATCC), 12301 Parklawn Drive, Rockville, Md, 20852, U.S.A. as pPAL0101/E. coli strain DH5 alpha under accession number ATCC 68210 that contains a constitutively expressed gene is shown in FIG. 10 and the fragment of this clone that contains a 5' promoter region along with a portion of transcribed sequence is identified. The fragment was isolated by first cloning the small 2.5 kb Eco RI fragment in pGEM 4Z, and obtaining a subclone that had this fragment inserted in the indicated orientation relative to the polylinker of pGEM 4Z. This subclone, pPAL 0101, was then digested with Eco RI, treated with Klenow fragment, then digested with Bam HI, which releases the promoter/transcribed region indicated. This fragment was cloned into Hinc II-Bam HI cut pGEM 4Z, resulting in the subclone pPAL HP101. The subclone can be used for the isolation of promoter sequences in vector constructs that utilize a constitutive promoter.

Recombinant DNA molecules containing any of the DNA sequences and promoters described herein may additionally contain selection marker genes which encode a selection gene product which confer on a plant cell resistance to a chemical agent or physiological stress, or confers a distinguishable phenotypic characteristic to the cells such that plant cells transformed with the recombinant DNA molecule may be easily selected using a selective agent. A preferred selection marker gene is neomycin phosphotransferase (NPT II) which confers resistance to kanamycin and the antibiotic G-418. Cells transformed with this selection marker gene may be selected for by testing in vitro phosphorylation of kanamycin using techniques described in the literature or by testing for the presence of the mRNA coding for the NPT II gene by Northern blot analysis in RNA from the tissue of the transformed plant. Transformed plant cells thus selected can be induced to differentiate into plant structures which will eventually yield whole plants. It is to be understood that a selection marker gene may also be native to a plant.

The male sterile plant may be produced by exposing a plant carrying a male sterile trait to a sterility actuating agent. For example, the male sterile plant may be produced by preparing a plant having integrated into its genome a first DNA sequence which encodes a first gene product which is capable of rendering a non-toxic substance cytotoxic to a cell of a plant which is critical to pollen formation and/or function regulated by a pollen specific promoter, and exposing the plant to a sterility actuating agent which is the non-toxic substance.

The male sterile plant may also be produced by preparing a plant having integrated into its genome a first DNA sequence which encodes a first gene product which is capable of rendering a non-toxic substance cytotoxic to a cell of a plant which is critical to pollen formation and/or function and a first promoter and a second DNA sequence which encodes a second gene product which is the non-toxic substance and a second promoter, the first or second promoter being an inducible promoter which is capable of being activated by a sterility actuating agent i.e. an inducer, throughout pollen formation, and the other of the first and second promoters being a pollen specific promoter, and exposing the plant to the inducer.

The male sterile plant may also be produced by preparing a plant having integrated into its genome a third DNA sequence which is an anti-sense gene which encodes an RNA which substantially interferes with the expression of a sense gene that is critical to pollen formation and/or function or a DNA sequence which encodes a substance which is cytotoxic to cells of a plant that are critical to pollen formation and/or function regulated by an inducible promoter, and exposing the plant to the inducer. The male sterile plant may also be produced by preparing a plant having integrated into its genome a 3rd DNA sequence which is an anti-sense gene which encodes an RNA which substantially interferes with the expression of a sense gene which confers on cells of a plant resistance to a chemical agent or physiological stress regulated by a pollen specific promoter, and exposing the plant to the chemical agent or physiological stress. The 3rd DNA sequence may be located on the same recombinant DNA molecules as the first or second DNA sequences which may be integrated into the genome of the male sterile plant or the 3rd DNA sequence may be located on a different recombinant DNA molecule. These and other methods which may be used for producing male sterility are described in Australian Patent Application Serial No. 611258 and in published PCT Application No. PCT/CA90/00037.

A recombinant DNA molecule containing any of the DNA sequences and promoters described herein may be integrated into the genome of the male sterile plant or second plant by first introducing a recombinant DNA molecule into a plant cell by any one of a variety of known methods. Preferably the recombinant DNA molecule(s) are inserted into a suitable vector and the vector is used to introduce the recombinant DNA molecule into a plant cell.

The use of Cauliflower Mosaic Virus (CaMV) (Howell, S. H., et al, 1980, Science 208: 1265) and gemini viruses (Goodman, R. M., 1981, J. Gen. Virol. 54: 9) as vectors has been suggested but by far the greatest reported successes have been with Agrobacteria sp. (Horsch, R. B., et al, 1985, Science 227: 1229–1231). Methods for the use of Agrobacterium based transformation systems have now been described for many different species. Generally strains of bacteria are used that harbour modified versions of the naturally occurring Ti plasmid such that DNA is transferred to the host plant without the subsequent formation of tumours. These methods involve the insertion within the borders of the Ti plasmid the DNA to be inserted into the plant genome linked to a selection marker gene to facilitate selection of transformed cells. Bacteria and plant tissues are cultured together to allow transfer of foreign DNA into plant cells then transformed plants are regenerated on selection media. Any number of different organs and tissues can serve as targets for Agrobacterium mediated transformation as described specifically for members of the Brassicaceae. These include thin cell layers (Charest, P. J., et al, 1988, Theor. Appl. Genet. 75: 438–444), hypocotyls (DeBlock, M., et al, 1989, Plant Physiol. 91: 694–701), leaf discs (Feldman, K. A., and Marks, M. D., 1986, Plant Sci. 47: 63–69), stems (Fry J., et al, 1987, Plant Cell Repts. 6: 321–325), cotyledons (Moloney M. M., et al, 1989, Plant Cell Repts 8: 238–242) and embryoids (Neuhaus, G., et al, 1987, Theor. Appl. Genet. 75: 30–36). It is understood, however, that it may be desirable in some crops to choose a different tissue or method of transformation.

It may be useful to generate a number of individual transformed plants with any recombinant construct in order to recover plants free from any position effects. It may also be preferable to select plants that contain more than one copy of the introduced recombinant DNA molecule such that high levels of expression of the recombinant molecule are obtained.

Other methods that have been employed for introducing recombinant molecules into plant cells involve mechanical means such as direct DNA uptake, liposomes, electroporation (Guerche, P. et al, 1987, Plant Science 52: 111–116) and micro-injection (Neuhaus, G., et al, 1987, Theor. Appl. Genet. 75: 30–36). The possibility of using microprojectiles and a gun or other devise to force small metal particles coated with DNA into cells has also received considerable attention (Klein, T. M. et al., 1987, Nature 327: 70–73).

It may also be possible to produce the male sterile plant by preparing a plant carrying a male sterile trait by fusing cells of a plant cell line containing cells having recombinant DNA molecules containing the DNA sequences and promoters described herein with cells of plant species that cannot be transformed by standard methods. A fusion plant cell line is obtained that carries a genetic component from both plant cells. Fused cells that carry the recombinant DNA molecule(s) can be selected and in many cases regenerated into plants that or carry the male sterile trait.

It is contemplated in some of the embodiments of the process of the invention that a plant cell be transformed with a recombinant DNA molecule containing at least two DNA sequences or be transformed with more than one recombinant DNA molecule. The DNA sequences or recombinant DNA molecules in such embodiments may be physically linked, by being in the same vector, or physically separate on different vectors. A cell may be simultaneously transformed with more than one vector provided that each vector has a unique selection marker gene. Alternatively, a cell may be transformed with more than one vector sequentially allowing an intermediate regeneration step after transformation with the first vector. Further, it may be possible to perform a sexual cross between individual plants or plant lines containing different DNA sequences or recombinant DNA molecules preferably the DNA sequences or the recombinant molecules are linked or located on the same chromosome, and then selecting from the progeny of the cross, plants containing both DNA sequences or recombinant DNA molecules.

Expression of recombinant DNA molecules containing the DNA sequences and promoters described herein in transformed plant cells may be monitored using Northern blot techniques and/or Southern blot techniques. The formation of microspores in plants which contain recombinant DNA molecule(s) such that they are rendered male sterile, is first monitored by visual microscopic examination of the anther structure. As maturation of the flower occurs, anther formation is expected to be delayed or completely inhibited such that no mature pollen grains are formed or released.

Where more than one recombinant DNA molecule of the invention is used to produce a male sterile plant as in the methods of the present invention, the recombinant DNA molecules may be inserted in the same chromosome pair in separate isogenic plant lines. The respective lines are preferably made homozygous for the respective recombinant DNA molecule(s) /gene prior to crossing the lines to produce a male sterile plant. Where a first and a second recombinant molecule are integrated into the same chromosome in the isogenic plant lines, a cross of these lines results in the first and second recombinant DNA molecules being located on separate chromosomes of the same chromosome pair in the male sterile plant. Consequently, when the male sterile plant is crossed with a suitable male fertile plant of a different line, both chromosomes of the chromosome pair segregate into separate F1 progeny with the result that the first and second recombinant DNA molecules are not expressed in the same plant. Thus, the F1 hybrid seed is fully fertile and thus has restored fertility. If the two recombinant DNA molecules are integrated into different chromosomes in the male sterile plant, then a portion of the F1 hybrid seed will be male sterile since there is a 25% probability of co-segregation of the chromosomes containing both recombinant DNA molecules into the male sterile plant. This latter approach may be advantageous with respect to outcrossing species. When the F1 male fertile plants outcross, a portion of the F2 seed will inherit both chromosomes containing the first and second recombinant DNA molecules and consequently will be male sterile. Where the seed is the commodity of commerce, it is advantageous for seed producing companies to use a scheme for hybrid seed production, where the saving of F2 hybrid seed is discouraged. The outcrossing in the F1 hybrid plants results in partial male sterility in the F2 generation, thereby reducing the seed yield of F2 plants, which is commercially desirable. An example of this method is as follows: a first male sterile plant line incorporating in its genome a recombinant DNA molecule having an IamH gene encoding IamH which converts non-toxic IAM to toxic levels of IAA, may be crossed with a second plant line having a genome incorporating a second recombinant DNA molecule having an IamS gene which converts tryptophan to IAM.

As indicated above, it may be desirable to produce plant lines which are homozygous for a particular gene. In some species this is accomplished rather easily by the use of anther culture or isolated microspore culture. This is especially true for the oil seed crop *Brassice napus* (Keller and Armstrong, Z. Pflanzenzucht 80: 100–108, 1978). By using these techniques, it is possible to produce a haploid line that carries the inserted gene and then to double the chromosome number either spontaneously or by the use of colchicine. This gives rise to a plant that is homozygous for the inserted gene, which can be easily assayed for if the inserted gene carries with it a suitable selection marker gene for detection of plants carrying that gene. Alternatively, plants may be self-fertilized, leading to the production of a mixture of seed that consists of, in the simplest case, three types, homozygous (25%), heterozygous (50%) and null (25%) for the inserted gene. Although it is relatively easy to score null plants from those that contain the gene, it is possible in practice to score the homozygous from heterozygous plants by southern blot analysis in which careful attention is paid to the loading of exactly equivalent amounts of DNA from the mixed population, and scoring heterozygotes by the intensity of the signal from a probe specific for the inserted gene. It is advisable to verify the results of the southern blot analysis by allowing each independent transformant to self-fertilize, since additional evidence for homozygosity can be obtained by the simple fact that if the plant was homozygous for the inserted gene, all of the subsequent plants from the selfed seed will contain the gene, while if the plant was heterozygous for the gene, the generation grown from the selfed seed will contain null plants. Therefore, with simple selfing one can easily select homozygous plant lines that can also be confirmed by southern blot analysis.

Two techniques may be used to produce plant lines which carry genes that segregate in a similar fashion or are on the same chromosome or a set of chromosome pairs. One may be a simple crossing strategy in which two transformants that are homozygous for a single inserted gene are crossed to produce F1 seed. The progeny plants from the F1 seed (F1 plant generation) may be crossed with a recipient plant and the segregation of the two inserted genes is determined (F2 plant generation). For example, where the IamH and IamS genes are the inserted genes, the F1 plants grown from the F1 seed will be male sterile. If the original transformants are homozygous for a single inserted gene, when crossed with a non-transformed plant to produce F2 seed, the F2 plants will be 100% male fertile if the two transformants originally used for the production of the F1 seed carried the IamH and the IamS genes on the same chromosome or in the same linkage group. If the genes are in separate linkage groups or on different chromosomes, a variable degree of male sterility will be seen, in theory 25% of the plants will be male sterile if the genes segregate completely independently of each other. This approach allows for the selection of breeding lines from the homozygous transformed plant lines that contain the IamS and IamH genes which will segregate substantially 100% in the hybrid seed sold for commercial use.

An alternative strategy may make use of extensive genetic maps available for many commercially grown crops and the many easily scoreable markers that are known for most linkage groups or chromosomes. In some cases, linkage groups and chromosomes may be equivalent, whereas in others, there may be more than one linkage group assigned to each chromosome. When there is a marker for each chromosome, identification of the chromosome into which the recombinant gene has been inserted is relatively simple. A cross is made between each individual transformant and a recipient plant that allows for visualization of the marker(s).

If there are scoreable markers that have been localized to each of the chromosomes in the plant, and the markers are scoreable in the generation produced by this cross, one can localize the segregation of the inserted gene with the marker, thereby establishing the chromosomal location of that gene. This therefore allows for the chromosomal or more importantly the linkage group with which the inserted gene segregates. Many crops such as corn, tomato and many cereal crops have extensive genetic maps that allow for the identification of the chromosome containing the inserted gene. It is contemplated that as more detailed chromosome maps are made, especially with the use of RFLP (restriction fragment length polymorphism) maps, the assignment of inserted genes to particular chromosomes will easily be done for most commercial crop species.

As a means of confirmation, or in plant species where chromosomal markers are not known, it is possible to use a technique called pulse-field electrophoresis (originally described by Schwartz and Cantor, Cell, 37: p67; 1984) to determine if different transformed plants contain inserted genes on the same chromosome. Pulse-field electrophoresis is a technique that can separate large DNA pieces, even chromosomal size, into a reproducible pattern on a gel. When this is done, it is possible to process this gel such that the chromosome spots can be analyzed by southern blotting techniques, localizing the inserted gene to a chromosome spot. When the entire population of primary transformants are analyzed in this fashion, it is a simple task to choose the two transformants that carry the inserted genes on the same chromosome spot.

In one embodiment of the process of the invention for producing hybrid seed a male sterile plant having a genome incorporating a recombinant DNA molecule having a first DNA sequence encoding a protein or polypeptide which renders a non-toxic substance substantially cytotoxic to a cell of a plant which is critical to pollen formation and/or function and a pollen specific promoter is crossed with a second plant which contains a second recombinant DNA molecule having a second DNA sequence which encodes a second gene product which converts a substance which is endogenous to a plant cell to the non-toxic substance. Preferably, the male sterile plant and second plant used in this method are isogenic and each line carries a homozygous loci for the first DNA sequence or the second DNA sequence. Most preferably the first and second DNA sequences are located on the same chromosome pair of the plant lines, such that in any cross of the two lines a single chromosome pair contains both the first and second DNA sequences. The first plant line is made male sterile by exposing the first plant line to the non-toxic substance. The protein or polypeptide encoded by the recombinant DNA molecule incorporated in the genome of the first plant line will render the non-toxic substance toxic in cells of the plant which are critical to pollen formation and/or function, thus producing a male sterile plant line. The male sterile plant line also preferably has a selection marker gene linked to the first DNA sequence encoding the protein or polypeptide which renders a non-toxic substance cytotoxic to facilitate harvesting of the seeds having cells containing the first and second DNA sequences.

When the first male sterile plant line and the second plant line are crossed, the first male sterile plant line produces seeds having cells containing the DNA sequence encoding a gene product capable of synthesizing the non-toxic substance (e.g. IAM) and the DNA sequence encoding the protein or polypeptide (IamH) which renders the non-toxic substance cytotoxic (e.g. IamH converts IAM to toxic level of IAA). The seed having cells containing the first and second DNA sequences will produce male sterile plants which may be pollinated with a male fertile line to produce commercial hybrid seed. If the first and second DNA sequences are located on the same chromosome or in the same linkage group, the DNA sequences will segregate completely in the F1 hybrid seed and the hybrid seed will be substantially male fertile.

Advantage is taken in the above-mentioned preferred method of the fact that-most plant species produce, per plant, many hundreds of seeds. In oilseed Brassica for example, one plant, under normal conditions can produce one thousand seeds. Using the method described above, one can expect a thousand-fold increase in seeds per unit area sprayed with the non-toxic substance. That is to say that, for example, when two isogenic lines are produced that carry the IamS and IamH genes, the first pre-production step involves the use of NAM to cause male sterility in the plant line that carries only the IamH gene. When cross pollinated with the pollen from the plant that contains the IamS gene, one can expect up to one thousand seeds per unit area, each seed capable of growing into a male sterile plant. When these seeds are planted and crossed with a male sterile plant, one can expect one thousand seeds per unit area. Therefore, if one were to plant one acre of the plant line carrying the IamH gene and the pollinator carrying the IamS gene, this acre would need to be sprayed with NAM. From this one acre however, enough seed would be obtained to grow 1000 acres of male sterile plants and pollinators, and from these 1000 acres, enough hybrid seed with restored fertility would be obtained to plant 1,000,000 acres of hybrid crop. The amount of management required to produce this hybrid seed is reduced over conventional methods because of the pre-production amplification step employed. If the IamH gene is linked to a herbicide resistance gene, one can plant the fields randomly to ensure high rates of cross pollination and use the herbicide to kill the pollinator plants after flowering. This method therefore allows for efficient hybrid seed production over methods where hybrid seed is harvested directly following the first cross pollination.

A preferred embodiment of the above method is described in more detail below with reference to FIGS. 1A, 1B and 2. As illustrated in FIGS. 1A and 1B, the method employs two plant lines which are homozygous, respectively, for the IamH gene (plant line A2) and the IamS (plant line A1) genes and otherwise isogenic. These genes are located on the same chromosome pair in each plant, preferably at the same genetic locus or a position such that the chance of a crossing over event is substantially reduced. Accordingly, plants produced from a cross of these two isogenic lines will contain the IamS and the IamH gene respectively on different chromosomes of a single chromosome pair. This will ensure that the two genes will segregate when this plant is crossed with a male fertile plant.

To produce the hybrid seed, a two step procedure is used. The first step involves a pre-production of an isogenic male sterile line, the second step is the hybrid seed production itself.

To accomplish the first step the following approach is used: The two isogenic lines A1 and A2 are planted in rows as shown, and when flowering starts, the plots are sprayed with NAM (naphthalene acetamide). NAM is also a substrate for the IamH enzyme. This chemical is a non-toxic version of the plant growth regulator NAA, and the action of the IamH gene converts NAM to NAA. Under the control of the pollen specific promoter, the IamH gene only is expressed in pollen of the A2 line, and as such NAA is only made in pollen of the A2 line. Since NAA is a plant growth regulator, normal anther and microspore development is altered, leading to male sterility in the A2 plant line when treated with NAM.

The IamH enzyme can use a number of other substrates, including indole acetamide, indole-3-acetonitrile, conjugates between glucose and IAA and conjugates between myo-inositol and IAA. (Follin et al. (1985) Mol. Gen. Genet. 201: 178-185). Spraying with any of these compounds will produce the same effect as spraying with NAM; namely male sterility in plants expressing the IamH gene.

The plants which contain the IamS gene under the control of the pollen specific promoter (plant line A1) are not affected by the NAM, since they are unable to convert NAM to NAA, therefore these plants remain fully male fertile and can cross pollinate the A2 plants which have now become male sterile after treatment with NAM. On the A2 line, seed is produced that contains both the IamH and IamS genes under the control of pollen specific promoters (plant seed A2/A1).

The seed produced on the A2 line (plant seed A2/A1) is harvested. This harvesting can be done by harvesting specific rows. Alternatively, the IamH gene (A2) may be linked to a gene for herbicide resistance so that the herbicide can be used for the roguing of the plant line A1. Herbicide application takes place after flowering and will kill the A1 plants so that only seed that has the genotype A1/A2 is produced. The seed harvested from such a field will produce substantially 100% male sterile plants. The cross produces plants that express both the IamS and the IamH genes only in the pollen. This leads to the conversion of tryptophan, an amino acid normally found in plant cells to IAM (indole acetamide) via the IamS activity and finally to IAA (indole acetic acid) via the IamH activity. The molecule IAA is a plant growth regulator that is cytotoxic in greater than normal concentrations in a cell of a plant that is critical to pollen formation and/or function, particularly, in the developing pollen grains or anther of the plant. Since the IAA and the precursor IAM are small molecules that can be transferred from cell to cell via diffusion or active transport, altered growth regulator levels are seen throughout the anther. This altered growth regulator level leads to abnormality in pollen and anther development, producing a male sterile plant. This plant can be pollinated with a male fertile line leading to commercial hybrid seed.

For the production of hybrid seed, the male sterile isogenic line can be planted in rows along side of a suitable male fertile plant, and the hybrid seed produced on the male sterile plant can be harvested. If the IamH gene is linked to a herbicide resistance gene, harvesting of hybrid seed is facilitated by using the herbicide to eliminate pollinator plants after cross pollination. The entire field can then be combined. All seed produced will therefore be hybrid. If the two genes (IamS and IamH) are located on the same chromosome or in the same linkage group, these two genes will segregate completely in the F1 hybrid seed. Since the plants will contain either the IamS or the IamH gene, but not both, the seed produced by this hybrid cross will be substantially 100% male fertile. Therefore the plants grown from the seed of this cross will be fully fertile and set normal levels of seed. The F2 seed that results from the harvest of this field however will contain a variable degree of male sterility, since in theory 12.5% or 2 out of 16 of the plants grown from this F2 seed will contain both the IamS and the IamH genes, as illustrated in FIG. 2.

Where there is poor outcrossing, the F2 sterility will be lower than the maximum of 12.5% since a portion of the plants will self and the progeny of selfed plants will not contain both genes. Accordingly, these plants will remain fertile in the F2 generation.

It is contemplated that as a variation of the above particularly preferred method, a number of different ways of producing the toxic molecule specifically in pollen can be envisioned. In all approaches, at least one step in the production of the cytotoxic molecule has to take place specifically within the pollen cells or anthers. For instance, it is possible to use a constitutively expressed IamS gene in a plant and to subsequently cross that plant with a plant that contains the IamH gene under the control of a pollen specific promoter such that IAM is produced in all cells of the plant, but the growth regulator IAA is produced only in pollen cells due to the action of the pollen specific IamH gene. Conversely, it is possible to have IamH constitutively expressed in a plant, and cross this plant with a plant that contains a pollen specific promoter driving the IamS gene. In this situation, the growth regulator IAA is only produced in pollen cells. It should be cautioned that in this case, one cannot use NAM to induce transitory male sterility in the plant that contains the IamH gene, since that application of NAM would be lethal to the plant. In this case then hand pollination would be the preferred way of combining those genes. With regards to these methods the preferred embodiment of the present invention places both the IamH gene and the IamS gene under the control of pollen specific promoters and preferably using the same pollen specific promoter or a pollen specific promoter whose expression substantially overlaps that of the other to each independently drive the expression of these two genes. Additionally, by linking the IamH gene to a selectable agent such as a herbicide, hybrid seed production is greatly facilitated.

Any number of genes could be used to carry out the process and methods of the invention providing that the simultaneous production of two or more enzymatic or synthetic activities specifically in pollen leads to the production of a substance which is toxic or inhibitory to normal pollen growth or specifically interferes with anther or pollen development. This implies that one or more of these activities could be constitutive in the plant, but that the final combination of all enzyme activities be limited to pollen. It is also envisioned that one of these activities could be inducible by natural or artificial means such that sterility could be induced in plants.

Specifically one embodiment of this method uses a plant line that carries a IamS gene under the control of an inducible promoter and a IamH gene under the control of a pollen specific promoter. These genes are preferably linked, but could be unlinked. When grown under inductive conditions, the plant becomes male sterile and can be pollinated by a suitable male fertile plant. The suitable plant could also carry a IamS gene under the control of a pollen specific promoter such that the progeny of this cross will be male sterile. These plants could then be crossed with a male fertile plant, producing hybrid seed.

Figure 5A:
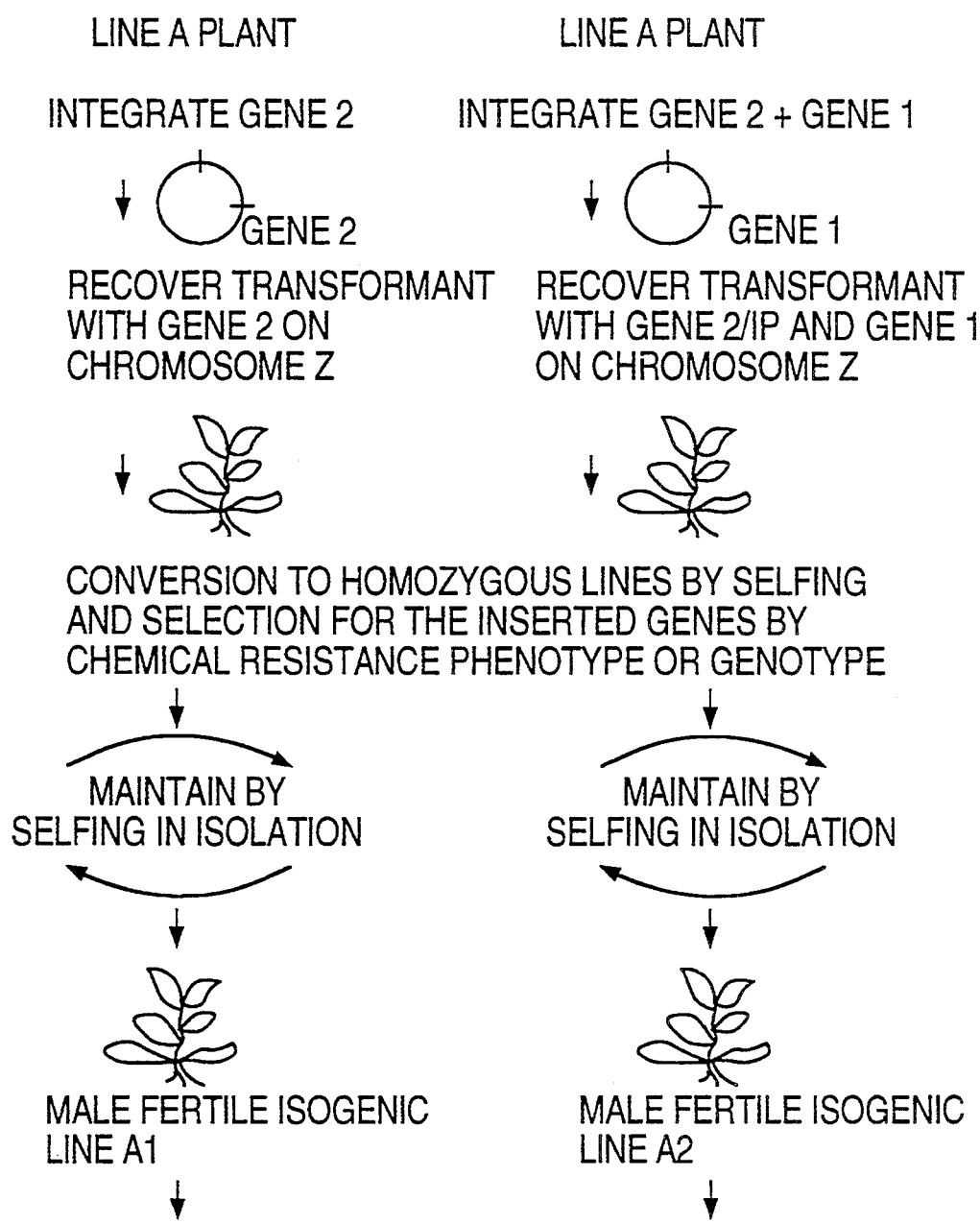
Figure 6:
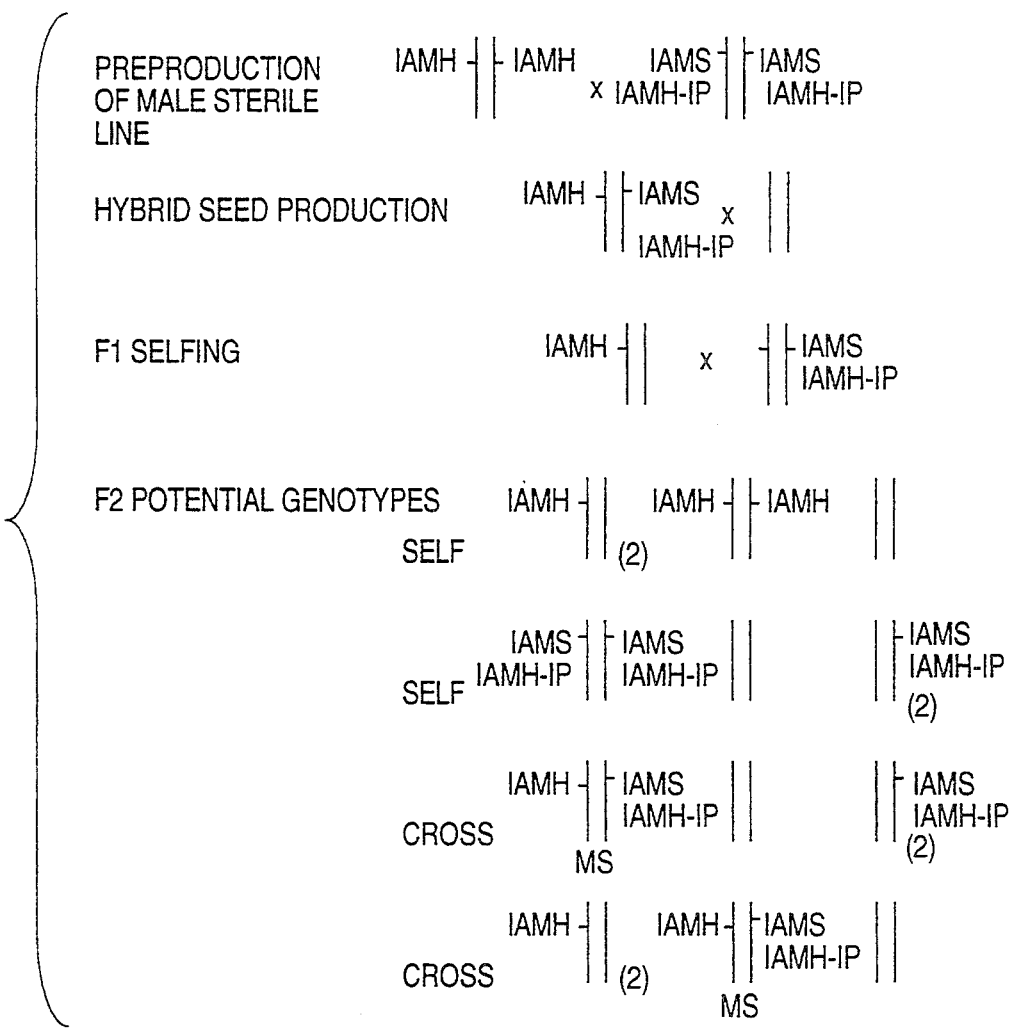
FIG. 6 illustrates the segregation patterns of an IamH gene and an IamS gene in the F1 and F2 populations produced as illustrated in FIGS. 5A and 5B.

The above mentioned embodiment employing a plant that carries a first recombinant DNA molecule having a DNA sequence encoding IamH and an inducible promoter, and a second recombinant DNA molecule having a gene encoding IamS regulated by a pollen specific promoter is described below with reference to FIGS. 5A, 5B and 6. It will be appreciated that the gene encoding IamH and are inducible promoter may be located on the second recombinant DNA molecule having the gene encoding IamS regulated by the pollen specific promoter. As illustrated in FIGS. 5A and 5B, the method employs two plant lines which are homozygous, respectively, for the first recombinant DNA molecule and second recombinant DNA molecule (plant line A2) and a first recombinant DNA molecule having a gene encoding IamH and a pollen specific promoter (plant line A1) and are otherwise isogenic. These genes are preferably located at the same genetic locus or a position such that the chance of a crossing over event on corresponding chromatids of a chromosome pair are substantially reduced. Accordingly, plants produced from a cross of these two isogenic lines will contain the first and second recombinant DNA molecules and the first recombinant DNA molecule on different chromatids of a single chromosome pair. This will ensure that the genes will segregate when this plant is crossed with a male fertile plant.

To produce the hybrid seed, a two step procedure is used. The first step involves a pre-production of an isogenic male sterile line, the second step is the hybrid seed production itself.

To accomplish the first step the following approach is used: The two isogenic lines A1 and A2 are planted in rows as shown, and when flowering starts, the plots are sprayed with an inducer. With reference to FIGS. 5A and 5B, the inducer is a chemical inducer. This chemical causes induction of the inducible promoter in the first recombinant DNA molecule such that expression of the gene encoding the IamH occurs in the A2 line. The IamS gene under the control of the pollen specific promoter is expressed only in pollen of the A2 line, and as such IAA is only made in pollen of the A2 line. In the presence of the enzyme IamH, IAM is rendered cytotoxic. Accordingly, normal anther and microspore development is altered, leading to male sterility in the A2 plant line when treated with the chemical inducer.

The plants which contain an IamH gene under the control of the pollen specific promoter (plant line A1) are not affected by the chemical inducer, since these plants do not produce IAM and are thus are unable to produce cytotoxic levels of IAA. Therefore these plants remain fully male fertile and can cross pollinate the A2 plants which have now become male sterile after treatment with the chemical inducer. On the A2 line, seed is produced that contains the first recombinant DNA molecule and the second recombinant DNA molecule from the A2 and the first recombinant DNA molecule from the A1 line (plant seed A2/A1).

The seed produced on the A2 line (plant seed A2/A1) is harvested, more particularly described as discussed above. The seed harvested from such a field will produce substantially 100% male sterile plants which may be pollinated with a male fertile line leading to a commercial hybrid seed as discussed above.

Table 1 outlines a number of possible embodiments according to the process of the invention. It is to be understood that this table does not represent all the possible embodiments but is merely representative of some of the various embodiments. In this Table the IamH and IamS genes are used to illustrate the methods but it is understood that any two DNA sequences which encode gene products which cooperate to selectively interfere with the function and/or development of cells that are critical to pollen formation and/or function may be utilized in the methods of the invention.

The following examples are further provided for illustrative purposes only and are in no way intended to limit the scope of the present invention.

EXAMPLES

Example 1

The construction of 6 vectors containing promoter and promoter fragments from the clone L4 is described in FIG. 7 (SEQ. NOS. 3 and 4) (a,b,c,d,e). The first step in the construction of these vectors was accomplished by first subcloning the Eco R1-Sst 1(nucl.1–2132) fragment containing the first gene of clone L4 (235 base pairs of promoter/exon/intron/second exon) in the commercially available vector pGEM-4Z(Promega Biotech, Madison, Wis., U.S.A.) using the Eco R1-Sst 1 sites of the polylinker of this vector. This plasmid was named pPAL 0402. The 2.7 Kb Eco RI fragment of clone L4 that contains the third gene (Bp4C) was then cloned into the Eco RI site of pGEM 4Z, leading to a plasmid called pPAL 0411. The plasmid pPAL 0402 was then digested with Eco R1 and the 2.7 Kb Eco R1 fragment from pPAL 0411(nucl. 5859–8579) that contains the gene number three (Bp4C) from clone L4 was added to it. Clones were recovered that contained this inserted 2.7 Kb Eco R1 fragment in both orientations relative to the promoter region of the first gene. A clone that contained this third gene fragment in a orientation such that the promoter from the third gene was opposite to the promoter in the first gene was chosen and called pPAL 0403. The plasmid pPAL 0403 contains the entire third gene from clone L4 oriented in such a fashion as to have the promoter region immediately adjacent to the 235 basepair promoter region of the first gene in pPAL 0403. This plasmid, pPAL 0403 was digested with Dde I, producing a fragment of approximately 1.9 Kb. The Dde I sites are located at nucleotides 303 and 7366. Because of the orientation of these fragments, digestion with Dde I produces a 1.9 Kb fragment. This 1.9 Kb fragment contains a copy of the third gene (Bp4C) oriented such that the direction of transcription of this third gene is from right to left, fused to the 235 base pair promoter fragment from the first gene of clone L4 (Bp4A) which is transcribed from left to right, ending in a Dde I site that is located 67 basepairs down stream of the major start site of transcription and precedes that ATG start of translation codon by 2 nucleotides. This 1.9 Kb Dde I fragment was made blunt with Klenow fragment and cloned into the Xba 1 site of the polylinker region of pGEM 4Z previously made blunt ended with Klenow fragment. The resultant plasmid pPAL 0408, was recovered and subsequently was digested with Sal 1 and Sst 1, which releases the cloned Dde 1 fragment bordered by on the left hand side, (nucl 7366) Sal 1 and on the right hand side (nucl 303) of this construct and contains a portion of the polylinker of pGEM 4Z containing the following unique sites: Bam HI, Sma I, Kpn I, and Sst I restriction enzyme sites. This Sal 1-Sst 1 fragment was cloned into the Sal 1-Sst 1 sites of PAL 1001. PAL 1001 is the binary vector Bin 19 (described by Bevan, M., Nucleic Acids Res., 1984, 12:8711–8721) to which has been added the nos ter polyadenylation signal as a 260 bp Sst 1-Eco R1 fragment isolated from the plasmid pRAJ 221 (available from Clonetech Laboratories, Palo Alto, Calif. U.S.A.) in the Sst 1-Eco R1 sites of the polylinker region of Bin 19. This nos ter is identified as a stippled box. The binary transformation vector that resulted from the insertion of the Sal I-Sst I fragment of pPAL 0408 into PAL 1001 was named PAL 1107. The details of the construction are shown in FIG. 7a. This vector has a copy of the third gene oriented such that the direction of transcription of this third gene is from right to left, fused to the 235 base pair promoter fragment from the first gene of clone L4 which is transcribed from left to right, followed by a polylinker with unique sites for the insertion of DNA which consist of: Bam HI, Sma I, Kpn I and Sst I followed by the nos ter signal. This vector has the feature in that additional 5' non-coding sequences were placed upstream to the 235 base pair core promoter on Bp4A, but these additional 5' sequences were in a opposite orientation. The provision of these sequences in this orientation does not affect the pollen specificity of the core 235 base pair promoter.

Figure 7A:
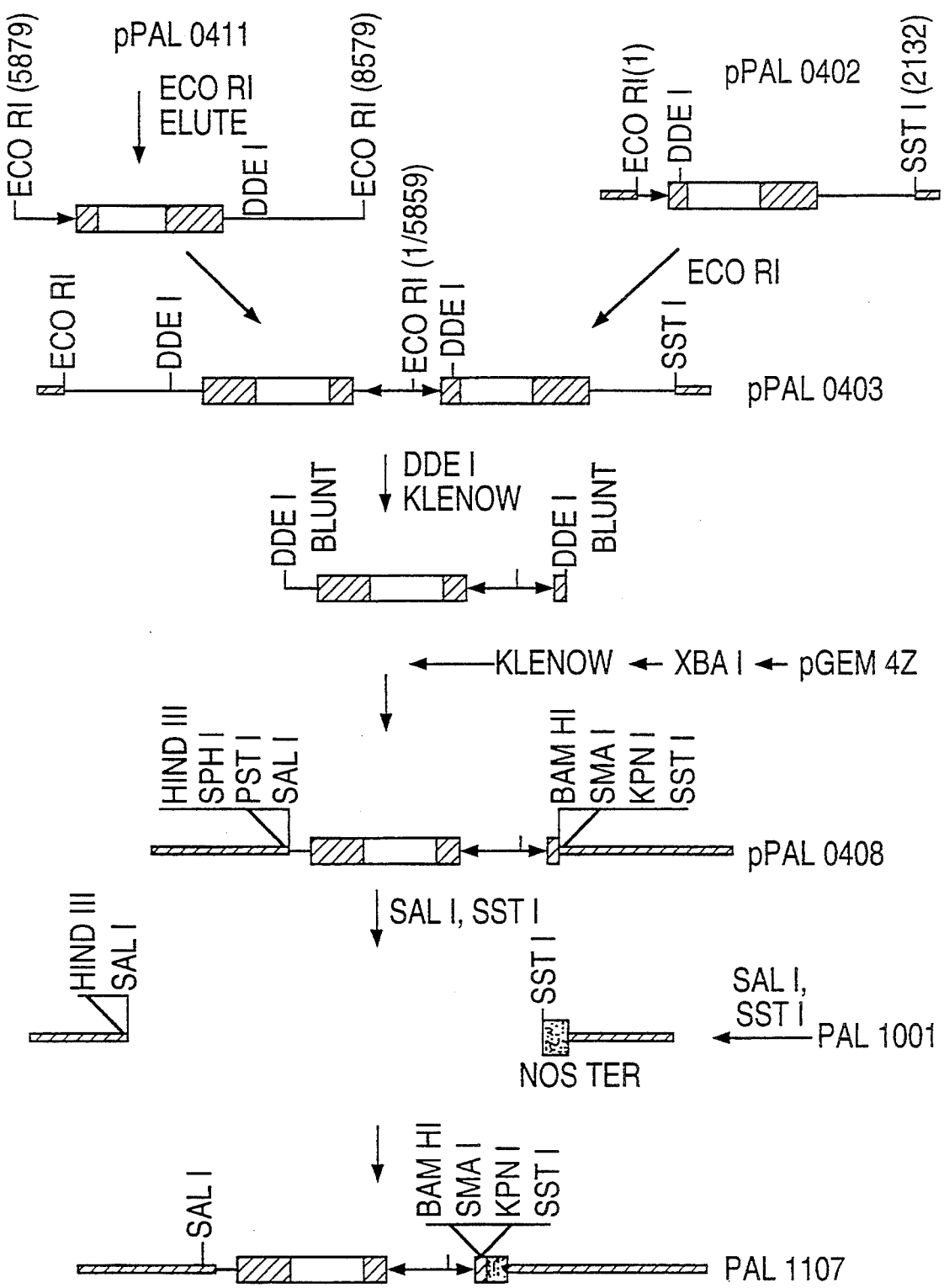
FIGS. 7A, 7B, 7C, 7D are schematic representations describing the production of vectors containing the promoter and promoter regions from clone L4 (SEQ. I.D. NOS. 3 and 4).
Figure 7B:
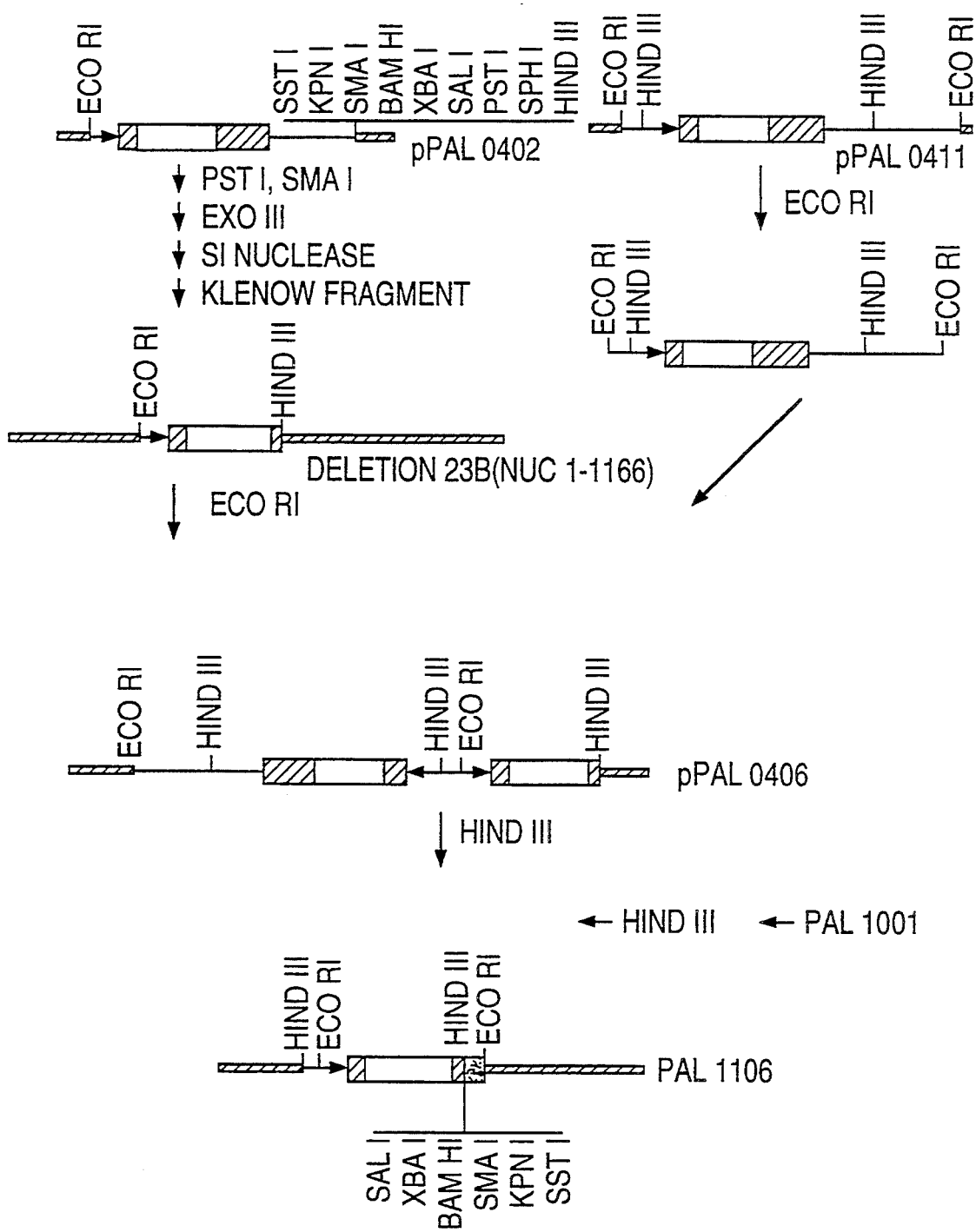

In addition to this vector, similarly structured vectors were made which contained essentially the same type of gene promoter arrangement but contained the intron of the first gene (Bp4A) of clone L4. Intron sequences in plant genes have been shown in some cases to play a role in gene expression. This intron containing vector was constructed by making a deletion series of the clone pPAL 0402. pPAL 0402 was first digested with Pst I and Sma I. Exonuclease III was used to unidirectionally digest the DNA as shown (FIG. 8b). After S1 nuclease treatment and repair with Klenow, the plasmid was relegated and clones that have had different portions of the coding regions of gene Bp4A digested out of them were recovered. Deletion subclones were sequenced. One was chosen for vector constructs. This is referred to as deletion 23B. This subclone represented a deletion that has most of the second exon of gene Bp4A removed but contains the intron splice site and first exon of gene Bp4A. This subclone contains a portion of the clone L4 that extends from nucleotide 1 to nucleotide 1166. To this subclone was added the 2.7 Kb Eco R1 fragment from pPAL 0411 that contains the third gene of L4 (Bp4C) in such an orientation that the direction of transcription of the third gene is from right to left (as in PAL 1107, pPAL 0408), fused to the 235 base pair promoter region from the first gene of clone L4 which is oriented to transcribe from left to right followed by the first exon of gene 1, the entire intron of gene 1 and 33 nucleotides of the second exon of gene Bp4A from clone L4. This plasmid containing deletion 23B and the 2.7 Kb Eco RI fragment containing the third gene fragment was named pPAL 0406. This plasmid was digested with Hind III, which yields a fragment containing a small portion of the promoter of the third gene as well as the entire promoter of the first gene, first exon, intron and a portion of the second exon. This Hind III fragment was inserted into the Hind III site of PAL 1001, resulting in the vector PAL 1106 (deletion 23B derived). This vector has in the following order, A portion of the promoter from the third gene in clone L4, the entire 235 base pair promoter of the first gene in clone L4, followed by the first exon, the intron and a portion of the second exon of gene 1 of clone L4, followed by a polytinker containing the following unique cloning sites: Sal I, Xba I, Bam HI, Sma I, Kpn I and Sst I and the nos ter polyadenylation signal. The construct is shown in FIG. 7b.

Example 2

Additional constructs with the promoter regions of the genes contained in clone L4 were done in order to provide a number of suitable vectors that are useful for pollen specific expression of gene sequences. The three genes within clone L4 (Bp4A, Bp4B, Bp4C) show very near-exact DNA homology and this is most apparent between the first (Bp4A) and third (Bp4C) gene. The second gene (Bp4B) is a homologous copy that has undergone sequence changes that appear to have lead to inactivation. The extensive similarity between the first, second and third genes in clone L4 is also maintained in the promoter region such that out of the first 235 nucleotides of the first and third gene promoter regions there are only 5 nucleotides that differ between them. Downstream of the TATA box in these two promoters the only difference between them is the presence of one additional nucleotide at the start of transcription. For example, comparison of Promoter 1, Bp4A, partially represented as: . . . TATGTTTtAAAA . . . (SEQ. NO. 9) with Promoter 3, Bp4C, partially represented as: . . . TATGTTTAAAA . . . (SEQ. NO. 10) shows that the transcribed region underlined and the single nucleotide difference in lower case. However, within the sequence of the first gene there is a nucleotide change that introduces a Dde I site (nucl 303) in the untranslated 5' leader sequence upstream of the ATG start codon that is not present in the untranscribed leader sequence of the third gene in clone L4. Chimeric promoter constructs were made which utilized this Dde I site in the first gene to combine with sequences from the third gene promoter. The region of the first promoter used for these constructs consisted of the sequences contained between the Sna BI site (nucl 210) near the TATA box to the Dde I site located immediately upstream of the ATG start codon in the first gene (nucleotide 303 is the first nucleotide in the recognition sequence for Dde I). The other region of this chimeric promoter (5' of the TATA box) was a fragment extending from the Eco R1 site of the third promoter (nucleotide 5858) to the Sna B1 site near the TATA box (nucleotide 6272). Therefore to facilitate construction of these pollen specific vectors, the following reconstructions were performed.

The Eco R1 to Dde 1 fragment that encompasses the promoter region of the first gene in clone L4 was isolated by first cutting pPAL 0402 with Dde 1, blunting with Klenow, and then cutting with Eco R1. The 235 base pair fragment corresponding to this region was cloned into the Eco R1-Sma 1 sites of pGEM 4Z. This plasmid (pPAL 0422), was then cut with Eco R1 and Sna B1. A DNA fragment that contained the Eco RI to Sna BI portion of the promoter for gene 3 in clone L4 was isolated by digesting pPAL 0411 with Eco R1 and Sna B1. This released an approximately 415 base pair Eco RI (nucl.5858) to Sna BI (nucl.6272) fragment that represents most of the 5' region of the gene 3 promoter from clone L4 (the Sna B1 recognition site is 2 base pairs downstream of the TATA box). This Eco R1-Sna B1 fragment was used to replace the shorter Eco R1-Sna B1 fragment removed for the first promoter subclone (pPAL 0422), reconstructing a promoter fragment of approximately 550 base pairs. This plasmid is referred to as pPAL 0421. This chimeric promoter fragment contains 415 base pairs of the promoter of gene three in clone L4, followed by approximately 99 nucleotides of the first gene promoter/untranslated leader sequence.

Example 3

For construction of a pollen specific cassette vector, the following plasmids were first constructed. The first plasmid constructed contained the nos ter polyadenylation signal with a polylinker in front of the nos ter signal. This was accomplished by first isolating from pRAJ 221 the nos ter as a Sst 1-Eco R1 fragment and this fragment was cloned in pGEM 4Z using the Sst 1 and Eco R1 sites in the polylinker. This subcloned is referred to as pPAL 001. To pPAL 001, a fragment coding for neomycin phosphotransferase (NPT II) derived from the plasmid pRAJ 162 was added to it in the anti-sense orientation as follows: The plasmid pRAJ 162 contains the NPT II gene from the transposon TN 5 inserted as a Sal I fragment and bounded by a polylinker in the plasmid pUC-9 (which was obtained from the Plant Breeding Institute, Cambridge, UK). pRAJ 162 was digested with Hind III and Sma I. The DNA fragment containing the NPT II gene was isolated by elution from an agarose gel. pPAL 001 was digested with Hind III and Sma I and the NPT II gene fragment was inserted. The resultant plasmid was called pPAL 002 and had such orientation of restriction sites and the NPT II gene and nos ter as follows: HIND III, Pst I, Sal I, 3' end NPT II coding sequence 5' end, Sal I, Bam HI, Sma I, Kpn I, Sst I, nos ter, Eco RI. pPAL 002 was cut with Hind III and the site made blunt ended by the use of Klenow fragment. pPAL 0421 was digested with Hinc II and Pvu II, both of which leave blunt ends, and the promoter fragment was ligated into Hind III cut blunt ended pPAL 002. Plasmids were obtained that contained the promoter in both orientations relative to the nos ter signal. One plasmid was chosen with the proper orientation (5' promoter/anti-sense NPT II/nos ter) and was named pPAL 0419. pPAL 0419 has the following DNA fragments: A small (approx. 130 bp) of pGEM 4Z that contains the SP6 promoter, the 550 base pair chimeric promoter, the NPT II gene in the anti-sense orientation relative to the promoter, followed by the nos ter polyadenylation signal. This entire promoter/NPT II/nos ter construct is excisable by Eco RI. pPAL 0419 was digested with Eco RI, and the promoter NPT II nos ter structure was cloned into BIN 19 using the single Eco RI site in the polylinker of BIN 19. The resultant transformation vector was named PAL 1419. In addition to the anti-sense NPT II gene, the vector contains a constitutive NPT II gene under the control of the nos promoter. This vector therefore confers resistance to kanamycin in all cell types with the exception of pollen cells where the gene expression from the constitutive promoter is inhibited by the anti-sense RNA produced from the promoter/NPT II/nos ter construct contained in PAL 1419.

Figure 7C:
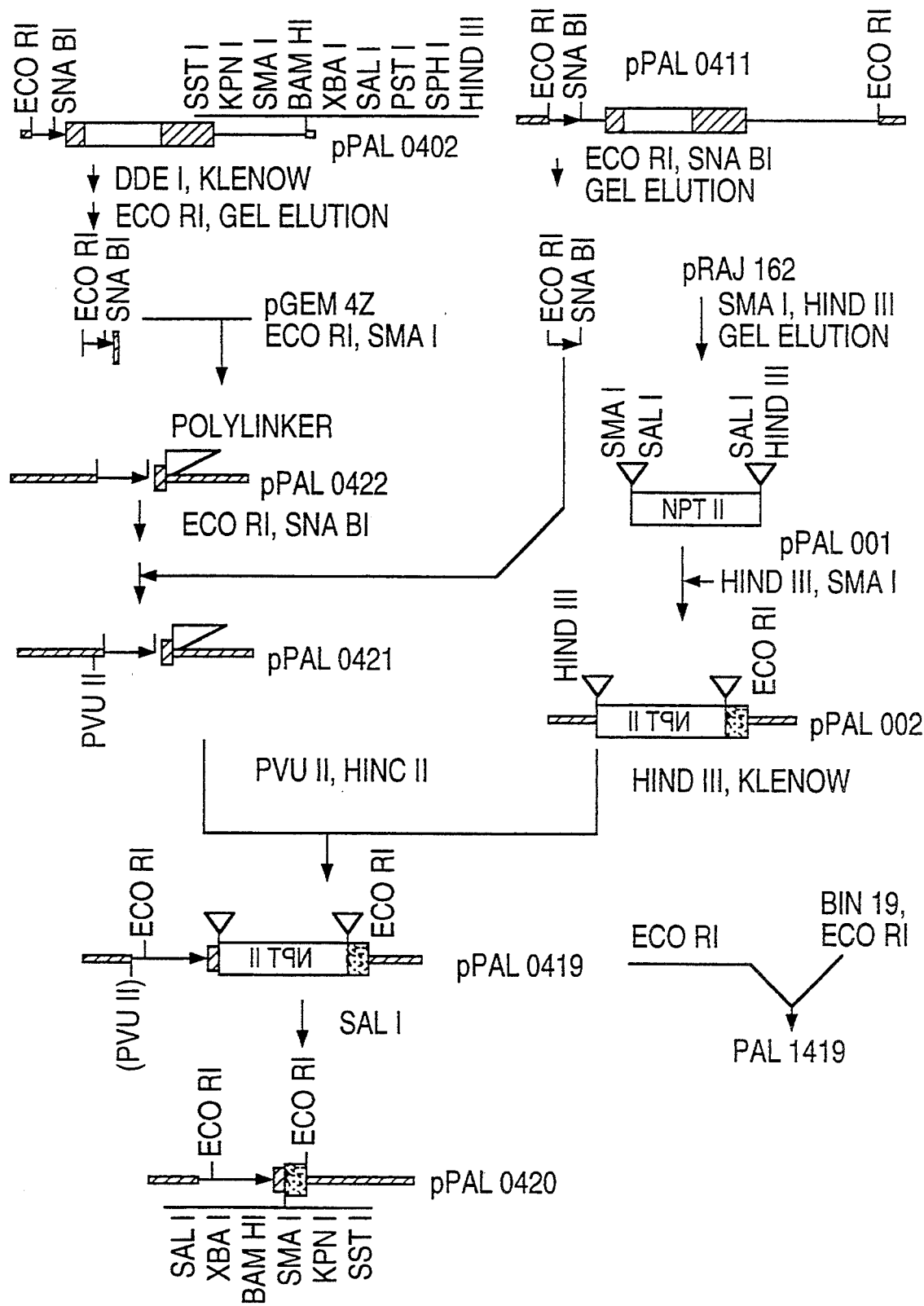

In order to provide promoter sequences that could be utilized with additional gene constructs, the plasmid pPAL 0419 was digested with Sal I. This digest removes the NPT II coding region and this Sal I digested pPAL 0149 was religated giving rise to pPAL 0420. pPAL 0420 represents the pollen specific promoter followed by a polylinker for insertion of genes that has the following unique sites: Hinc II, Pst I, Sal I, Bam HI, Sma I, Kpn I, Sst I, followed by the nos ter polyadenylation signal. The entire promoter/polylinker/nos ter construct can be conveniently excised as a single Eco RI fragment. details of this construct is shown in FIG. 7c.

Example 4

Figure 7D:
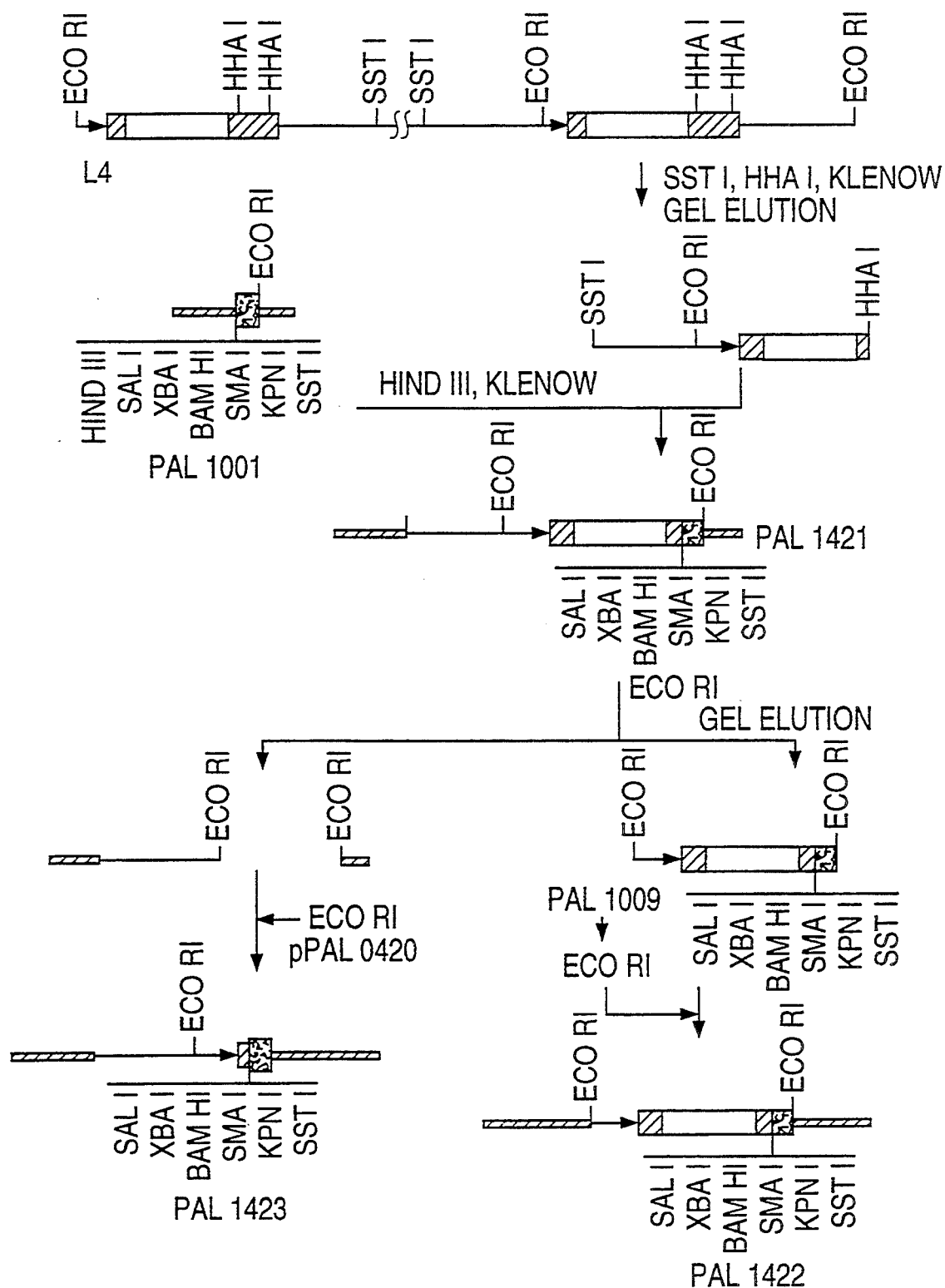

For additional pollen specific promoter constructs, the following approach was used. The intact L4 clone in the lambda cloning vector was digested to completion with the restriction enzymes Sst I and Hha I. The resultant fragments were separated by gel electrophoresis and a 2.65 Kb fragment that contains the promoter/first exon/intron/partial second exon region of gene three in clone L4 and corresponds to nucleotides 4565 to 7210 in the sequence of clone L4 was isolated. This fragment was made blunt ended with Klenow and cloned into the binary transformation vector PAL 1001 previously described. PAL 1001 was first cut with Hind III and made blunt ended with Klenow. Clones containing this fragment (promoter/first exon/intron/partial second exon) were recovered. A clone was chosen that contained this fragment in the proper orientation such that the direction of transcription was towards the nos ter in PAL 1001. This vector was named PAL 1421. This vector contains approximately 1.9 kb of upstream promoter region from the gene 3 in clone L4 followed by the first exon, the complete intron and 15 bases of the second exon of gene three followed by a polylinker containing the following unique sites: Sal I, Xba I, Bam HI, Sma I, Kpn I, SstI, and finally the nos ter polyadenylation signal. A variant of this vector was constructed by digesting PAL 1421 with Eco RI and isolating the fragment from this clone that contains the promoter polylinker nos ter sequences but contained less of the upstream region of the promoter. This fragment was re-cloned into PAL 1009. PAL 1009 is a BIN 19 derived vector from which most of the polylinker has been removed. This vector was constructed by digesting BIN 19 with Hind III and Sst I, making these sites blunt ended with Klenow and relegating such that a vector was recovered that contained a single unique Eco RI site for the insertion of fragments. PAL 1009 was digested with Eco RI and the Eco RI fragment from PAL 1421 that contains a shorter promoter/exon/intron/second exon/polylinker/nos ter structure was added to it. This gave rise to the vector PAL 1422, a vector that is essentially the same as PAL 1421 with the exception that there is less 5' promoter region. It should be noted that both PAL 1421 and PAL 1422 contain the intron from the third gene. For constructs which the presence of the intron may not be desired, intron sequences were removed from PAL 1421 by first digesting PAL 1421 with Eco RI and replacing the promoter/exon/intron/second exon/polylinker/noster structure with the promoter/polylinker/nos ter structure from pPAL 0420 using Eco R1 such that a longer 5' promoter region is reconstructed in the binary transformation vector. The resultant vector was named PAL 1423. The outline of this construction is shown in FIG. 7d.

Figure 7E:
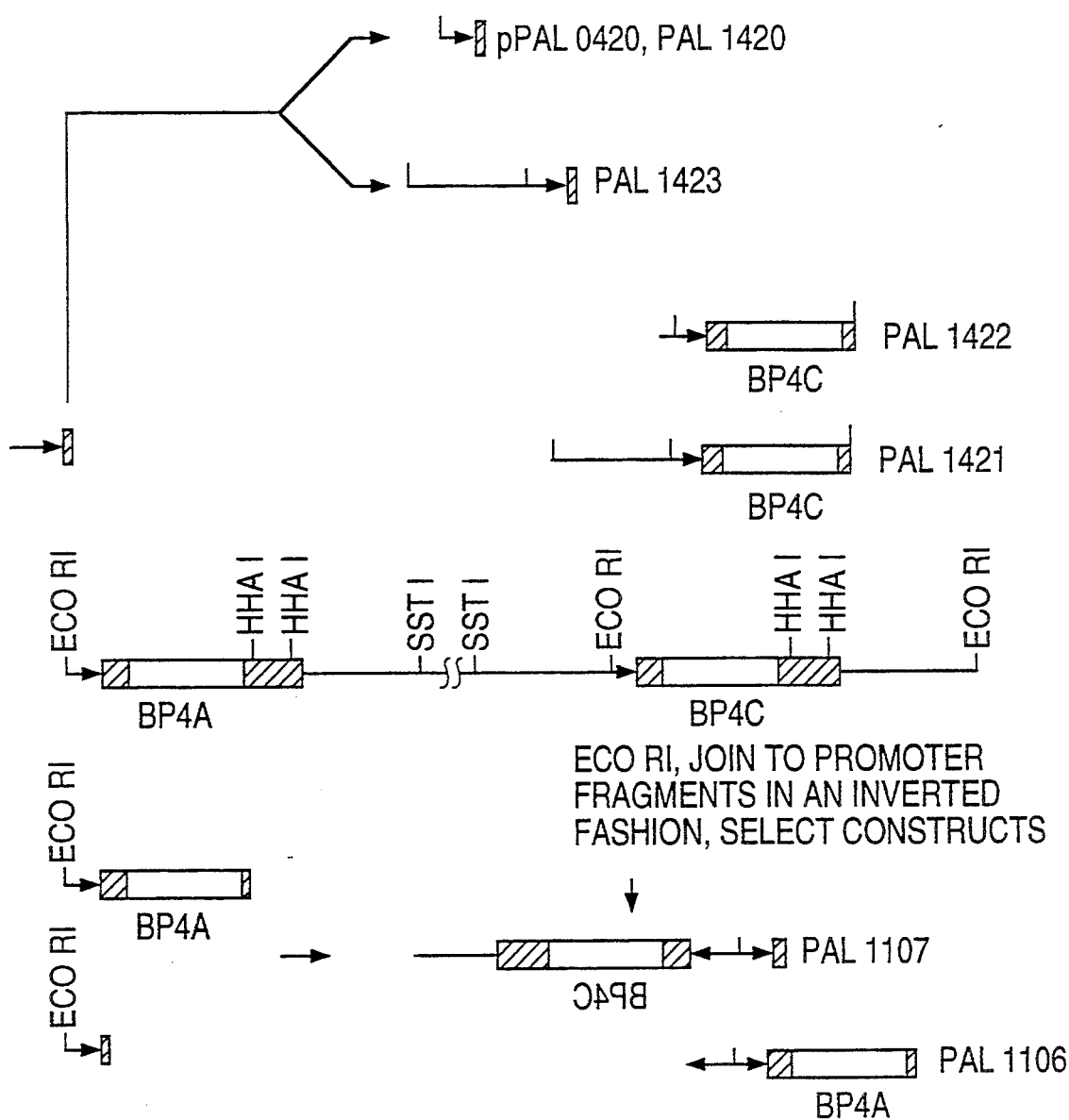
FIG. 7E shows a schematic representation of the promoter constructs produced as shown, schematically in FIGS. 7A to 7D.

In FIG. 7e, a schematic diagram of the relationship of the above described vectors is presented. It should be noted that the vectors outlined in this Figure fall into three categories: 1, vectors which contain 5' upstream promoter regions that are substantially derived from the upstream region of the gene Bp4C (pPAL 0420, PAL 1420, PAL 1423), 2, promoter constructs that contain 5' upstream promoter regions and intron sequences from the gene Bp4C (PAL 1422, PAL 1421) and, 3, promoters which contain a chimeric 5' upstream region in which a portion of the 5' DNA sequence is inverted relative to the arrangement which appears in the genomic clone and uses the promoter fragment of Bp4A as a core promoter structure (PAL 1107, PAL 1106). It should be noted that the functioning of each of these constructs can vary from plant species to plant species and it may be desirable to test a number of these promoter constructs when carrying out certain aspects of this invention.

Example 5

Figure 8:
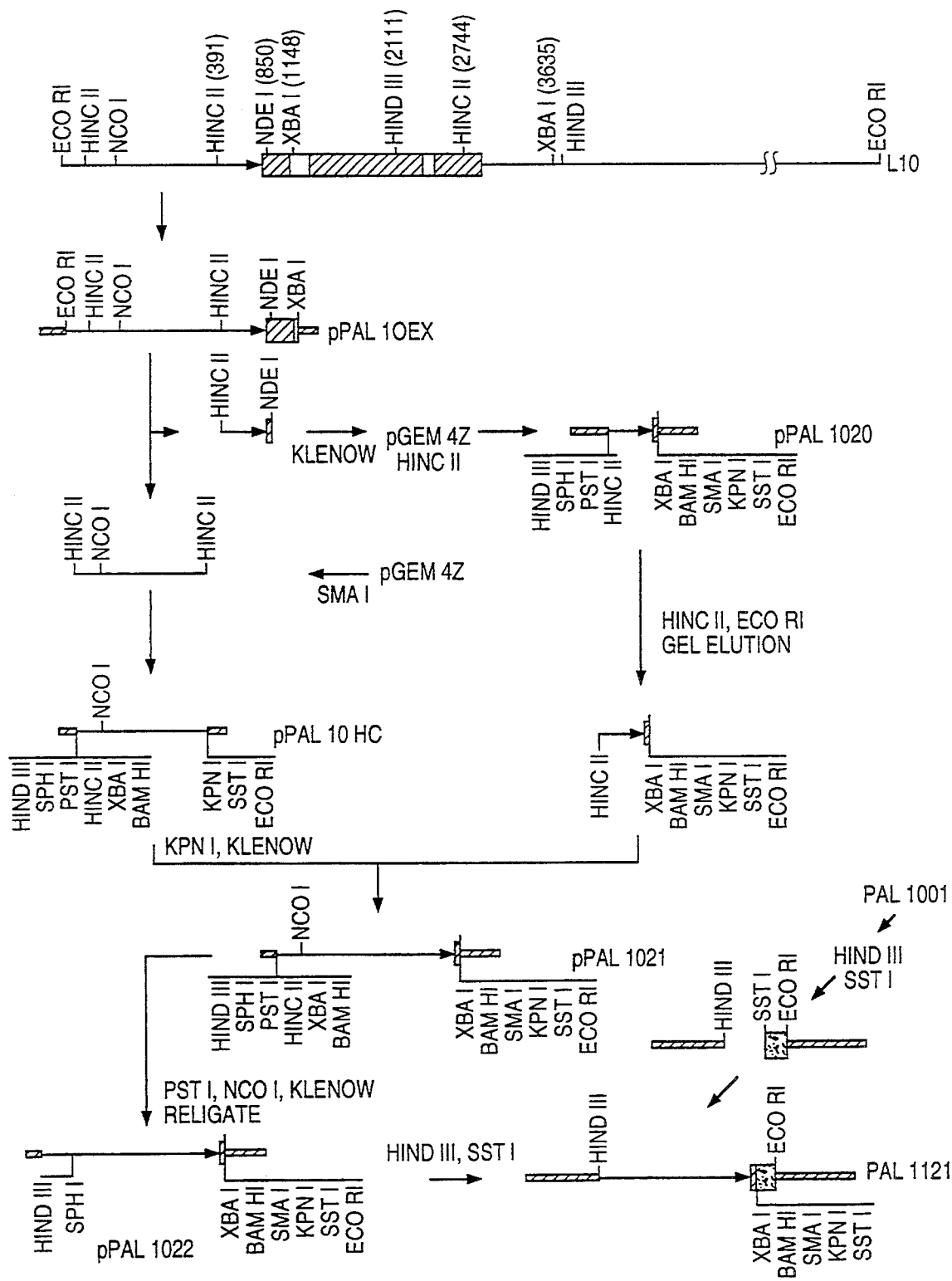
FIG. 8 is a schematic representation describing the production of vectors containing the promoter regions of clone L10 (SEQ. NOS. 5 and 6).

The construction of pollen specific vectors that utilize the promoter regions of clones L10 (SEQ. NOS. 5 and 6) and L19 (SEQ. NOS. 7 and 8) was conducted as follows. The construction of the pollen specific vectors depicted in FIG. 8 utilizes promoter regions from clone L10. The start of transcription of clone L10 is located at nucleotide 1. The ATG start codon is located at nucleotides 65–67. The promoter region of this clone was excised by first subcloning the Eco RI-Xba I fragment of the clone that encompasses the entire promoter region and a portion of the first exon (the Xba I site is nucleotide 359 in the DNA sequence). This subclone (pPAL 10EX) was then digested with Hinc II and Nde I. The Nde I site is located immediately upstream of the ATG start codon at nucleotide 62 and the Hinc II site is located at nucleotide number −399. The digestion with these two enzymes releases a DNA fragment of 460 nucleotides which contains 64 nucleotides of untranslated transcribed leader sequence, and 396 nucleotides of 5' promoter region. The Nde I site in this fragment was made blunt ended by the use of Klenow, and this fragment was subcloned into the Hinc II site of the polylinker of pGEM 4Z. Clones were recovered in both orientations and the clone that contained the fragment in the orientation: Hind III, Sph I, Pst I. Hinc II, promoter 64 base pair leader fragment (Nde I blunt/Hinc II, does not cut with either Hinc II or Nde I) Xba I, Bam HI, Sma I, Kpn I, Sst I, Eco RI was chosen and named pPAL 1020. To add additional upstream regions, the Hinc II-HincII fragment that is approximately 1 Kb in length and is immediately upstream of the Hinc II site at position −399 in the DNA sequence was isolated from pPAL 10EX by digestion with Hinc II and gel elution of this fragment. This Hinc II fragment was cloned into the Sma I site of pGEM 4Z. Clones which contained the fragment in both orientations were recovered and a clone that contained the fragment in the following orientation was chosen: Hind III, Sph I, Pst I, Hinc II, Sal I, Xba I, Bam HI, the Hinc II fragment in the same orientation as in the genomic clone, that being right to left, 5'-3' (as a Hinc II/Sma I insertion which does not cut with either enzyme), Kpn I, Sst I, Eco RI. This subclone (pPAL10Hc) was digested with Knp I, made blunt end by the use of Klenow, then digested with Eco RI. To this cut subclone was added the promoter/untranslated leader sequence of pPAL 1020 by digesting pPAL 1020 with Hinc II and Eco RI, and adding this promoter fragment to the cut pPAL 10Hc. The resultant subclone contained a reconstructed promoter region of clone L10 differing from the intact region by only the filled in Kpn I site used for the joining of the two promoter fragments. This construct was named pPAL 1021. This vector contains in the following order: Hind III, Pst I, Sph I, Hinc II, Sal I, Xba I, Bam HI, the approximately 1 Kb Hinc II fragment joined to the Hinc II-Nde I promoter fragment followed by Xba I, Bam HI, Sma I, Kpn I, Sst I, and Eco RI. This subclone allows for the convenient removal of the promoter region of clone L10 such that the promoter can be easily used in cassette transformation vectors. The outline of this construction is shown in FIG. 8. The promoter region of pPAL 1021 was used for the construction of a pollen specific cassette transformation vector by carrying out the following constructs: The plasmid pPAL 1021 was digested with Nco I and Pst I. The plasmid was treated with Klenow and religated.

This procedure effectively removed the portion of the polylinker that was 5' to the promoter in pPAL 1021. This plasmid was then digested with Hind III and Sst I, and cloned into the Hind III and Sst I sites of PAL 1001, giving rise to PAL 1121. PAL 1121 has in the following order: the pollen specific promoter of clone L10 (approximately 1.1–1.2 Kb), followed by a polylinker with the following unique sites: Xba I, Bam HI, Sma I, Kpn I, Sst I, followed by the nos ter. The construction of this is outlined in FIG. 8.

Example 6

Figure 9:
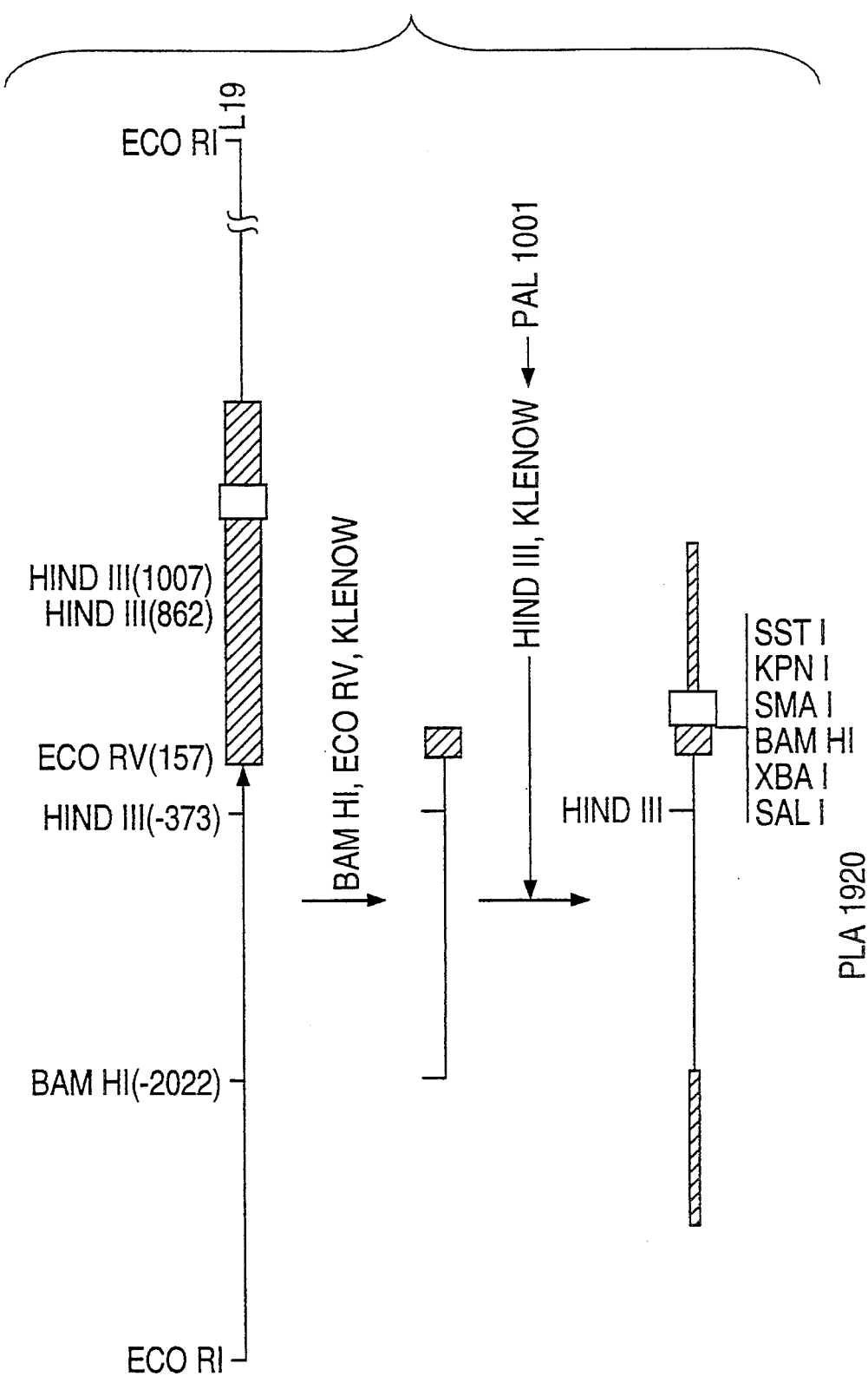
FIG. 9 is a schematic representation describing the production of vectors containing the promoter regions of clone L19 (SEQ. NOS. 7 and 8).

The promoter region of the clone L19 (SEQ. NOS. 7 and 8) as also used for construction of pollen specific vectors. The construction of these vectors is as shown in FIG. 9. Clone L19 has a single pollen specific gene contained with it. The start of transcription in this gene is located at position 1 in the DNA sequence. The ATG start codon is located at nucleotide position 136–138. The only intron is located at nucleotides 1202–1338, the stop translation codon is located at nucleotides 2025–2027. The end of transcription is located at approximately nucleotide 2074. The entire Eco RI fragment of this clone was subcloned into PGEM 4Z by using the Eco RI site located in the polylinker. The resultant clone was named pPAL 1901. The promoter region of this clone was excised as a single fragment by digesting pPAL 1901 with Bam HI and Eco RV, and a 2177 basepair fragment corresponding to the promoter region was isolated. This fragment covers from nucleotide −2022 (Bam HI) to nucleotide 156 (Eco RV). This promoter fragment contains over 2 Kb of 5' upstream region of the promoter in clone L19, 134 basepairs of 5' untranslated leader sequence and 23 basepairs of translated sequence. The Bam HI site in this fragment was made blunt ended by the use of Klenow and cloned into PAL 1001. This step was accomplished by cutting PAL 1001 with Hind III, making this site blunt ended by the use of Klenow and inserting the blunt ended Bam HI-Eco RV fragment in such an orientation that the promoter was oriented 5' to 3' with respect to the polylinker/nos ter polyadenylation signal. This vector was named PAL 1920 and contained within it in the following order: The promoter from clone L19 containing 135 base pairs of 5' untranslated leader sequence, 23 base pairs of translated sequence fused to a polylinker containing a former Hind III site inactivated by blunt ending, Sph I, Pst I, Sal I, Hinc II, Xba I, Bam HI, Sma I, Kpn I, Sst I (the unique cloning sites are underlined), the nos ter polyadenylation signal. This vector is convenient for the insertion of DNA sequences to be transcribed in pollen cells. The outline of this construct is shown in FIG. 9.

Example 7

This example describes methods used to transform tobacco and Brassica napus.

For tobacco transformation, the tobacco cultivar, *N. tabacum*, cv. Delgold was used. To accomplish this transformation, tobacco leaves less than 8 inches in length were surface sterilized by exposure to ethanol for 5–6 seconds, then subsequent exposure to 1% sodium hypochlorite for a few minutes, usually 5–10 minutes, or until the cut edge of the petiole turned white, then were rinsed several times in sterile distilled water. Leaf segments of approximately 0.5 to 1.0 square centimeters were excised from the sterile leaves, and were cocultured on shoot inducing media for two days with *Agrobacterium tumefaciens* GV 3101 carrying the Ti plasmid pMP 90 to provide vir functions in trans (described by Koncz, C. and Schell, J., 1986, Mol. Gen. Genet. 204:383–396) carrying the binary vector of interest. The vector is usually a derivative of Bin 19 which contains the NPT II gene driven by the nopaline synthase promoter and terminated by the nos ter for selection of plant cells with kanamycin. Bin 19 is available from Clonetech Laboratories, Palo Alto, Calif., U.S.A. Transformed tobacco cells are selected on a shoot-inducing medium containing 0.8% agar, MS salts, B5 vitamins, 3% sucrose, 1 mg per L of benzyladenine, 0.1 mg per L of alpha naphthalene acetic acid, (NAA) 300 $\mu$g/ml kanamycin and 500 $\mu$g/ml carbenicillin (essentially as described by Horsch et al. 1985, Science, 227:1229–1231). Regenerated shoots are then transferred to a root-inducing medium consisting of B5 medium with 2% sucrose, 500 $\mu$g/ml carbenicillin and 0.5 mg/L each of NAA and indoleacetic acid (IAA). Rooted transformants are transferred to a misting chamber containing high humidity, after which the humidity is gradually lowered and plants are subsequently transferred to the greenhouse.

For transformation of *Brassica napus*, the binary vector containing Agrobacterium strain GV 3101 carrying pMP 90 to provide vir functions in trans is used. Transformation was carried out either using the method described in Moloney, M. M., et al. (Plant Cell Reports 1989 8:238–242) or, transformation can be carried out with surface sterilized stem epidermal layers. For this procedure, seeds of *B. napus L.* ssp. *oleifera* cv. Westar were sown in 'Promix' mixed with 2 g/l of the slow-release fertilizer 'Nutricoate' in 8" pots. Plants were grown in the greenhouse under a 16 photoperiod (using natural and artificial lighting). For coculture and regeneration experiments stem-sections from the top three stem internodes of approximately 1.5 month old plants were used (i.e. those with elongated floral spikes and several open flowers). Intact stem-sections were surface sterilized for 30 seconds in 70% ethanol and 10 minutes in 1% sodium hypochlorite followed by three rinses in sterile distilled water.

For transformation *Agrobacterium tumefaciens* GV 3101 carrying the Ti plasmid pMP 90 to provide vir functions in trans and the binary vector of choice was grown on YEP media (which consists of 10 gm per L of Yeast Extract, 10 gm per L of Bacto-peptone and 5 gm per L of NaCl, pH 7.0 containing 100 ugs per mL kanamycin for selection of bacterial cells that contained the binary vectors). Cells were grown from one to two days at 28 C. The cells were collected by centrifugation and were resuspended at an approximate density of $10^6$–$10^7$ cells per mL in liquid EL which consists of MS micro- and macro-nutrients and B5 vitamins containing 40 mg/L of FeNa-EDTA (obtained from BDH chemicals) and 3% sucrose, 10 mg/L BenzylAdenine, and 0.5 mg/L alpha naphthalene acetic acid (NAA) and 18.8 mM $KNO_3$ plus 20.6 mM $NH_4NO_3$. Medium was solidified with 0.8% agar (Sigma) when the EL media was used for solid media plates.

The cell suspension was poured into the bottom of a sterile petri dish and sterilized stems were dissected directly in the bacterial suspensions. The segments were sectioned longitudinally into half segments and cut into approximately 5 mm sections. The dissected segments were placed on filter paper disc on solid EL media for a 3 day coculture under continuous fluorescent light (60 microeinsteins/m$^2$/sec$^2$) at 25° C. After a 2–3 day coculture, explants were transferred to solid EL media containing 500 ug/mL carbenicillin, and 100 ug/mL bekanamycin (Sigma). Shoots formed in 4-8 weeks, sections were transferred to fresh solid EL media with carbinicillin and bekanamycin every 3-4 weeks. Shoots that formed and did not bleach were excised and rooted on PDR media (B5- with 2% sucrose and 0.5 mg/L each of NAA and IAA). In some cases, green non-regenerating callus growing on selective medium was separated from explants and transferred to fresh medium to stimulate regeneration. Transformed plants were placed in misting chamber, and after two-four weeks transferred to the greenhouse. Plants were grown under a 16 hour photoperiod and allowed to flower.

Clonal propagation was used to increase plant lines as well as hand crossing and selection of seedlings from crossed plants on kanamycin containing media. This media consisted of 0.8% agar, one-tenth MS salts and 100 ugs per mL bekanamycin (available from Sigma Chemicals, St. Louis, Mo., U.S.A.) with no sucrose in the media. Surface sterilized seeds were used. The seeds were surface sterilized by rinsing in 70% ethanol for a few seconds, soaking in 1% sodium hypochlorate for 15 minutes, followed by rinsing three times in sterile distilled water. Seeds were placed on the surface of the agar in sterile dishes and allowed to sprout. Plants which did not carry the kanamycin gene linked to the antisense gene bleached and died, while those that carried the antisense gene stayed green and were subsequently transferred to soil and allowed to flower.

Example 8

Figure 4A:
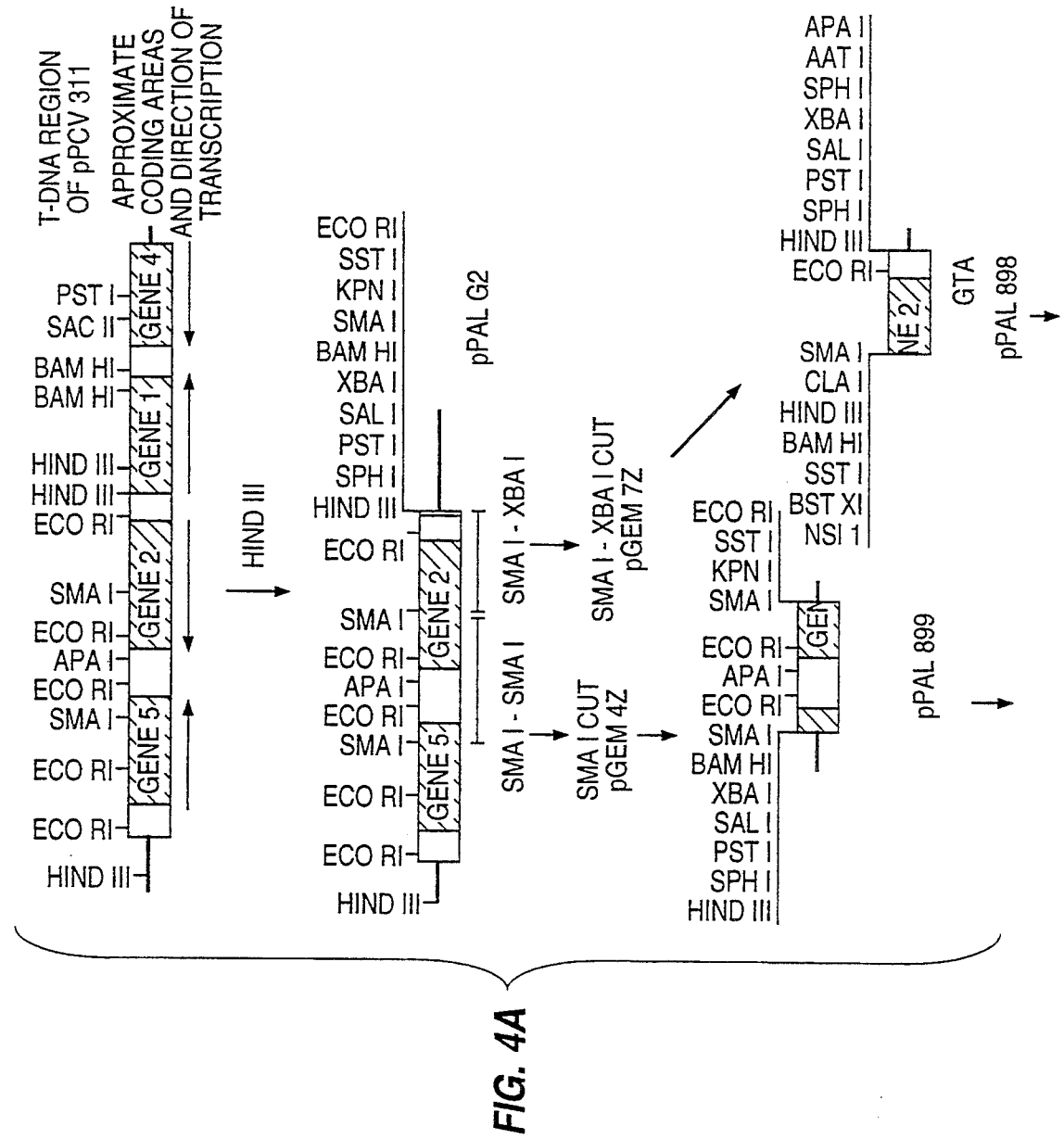
FIGS. 4A and 4B illustrate the procedure used for the isolation of the T-DNA gene 2 (the IamH: indole acetamide hydrolase gene) of the *Agrobacterium tumefaciens* Ti plasmid derivative pPCV 311 and the construction of a promoterless version of this gene.
Figure 4B:
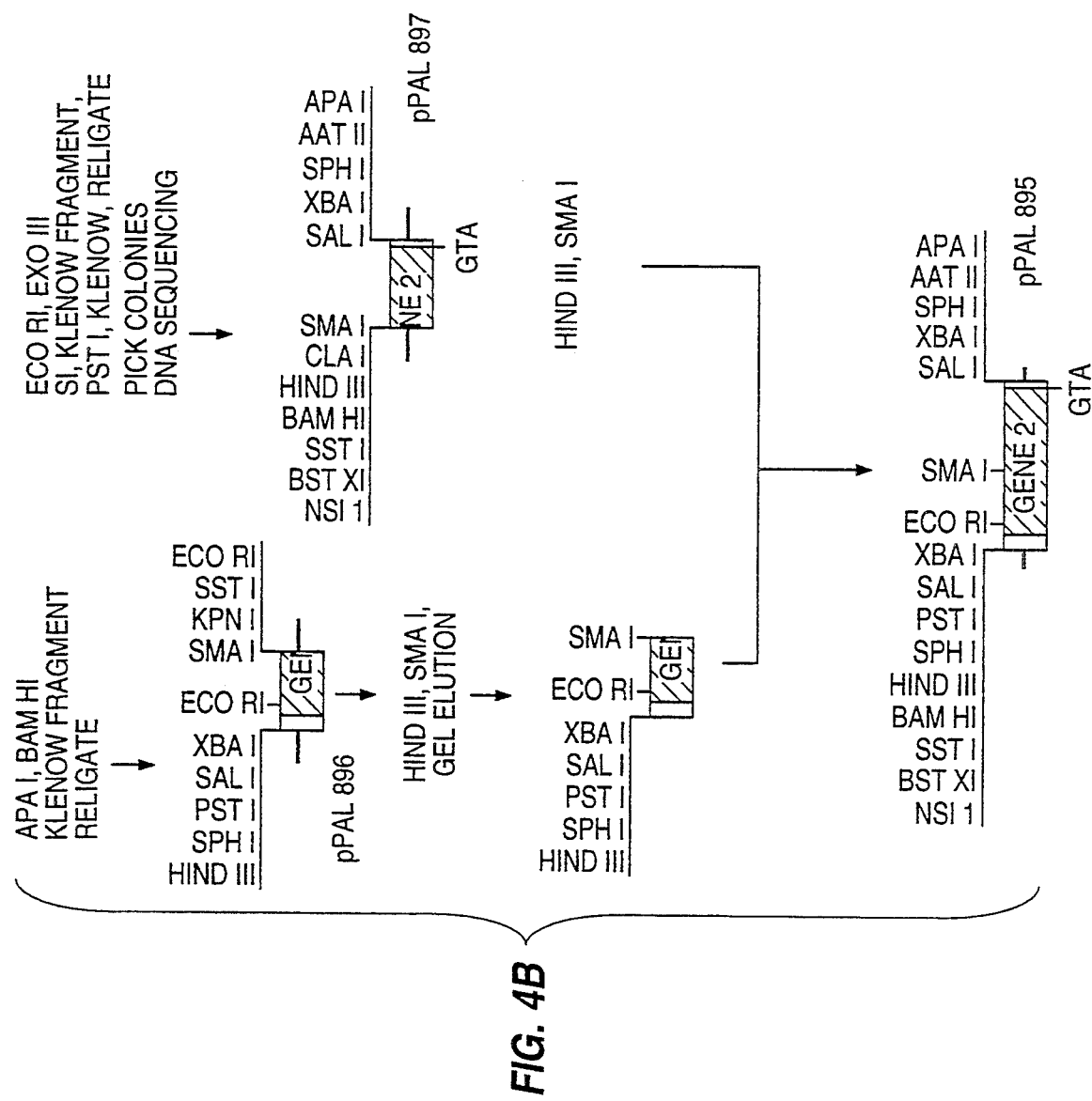

This example describes the isolation of two genes involved in tumour formation in plant tissues following infection with Agrobacterium, the IamS and the IamH genes from the Ti plasmid of the *Agrobacterium tumefaciens* strain C58. The isolation of the IamH gene is particularly described. The source of DNA coding for these genes was the plasmid pPCV 311. The plasmid pPCV311 is described in: Koncz, C. and Schell, J., Molecular and General Genetics, 1986, 204:383–396, and contains the oncogenic region of the T-DNA plasmid contained in the C58 strain of Agrobacterium. The plasmid pPCV 311, contains a region of T-DNA that when transferred to plant cells causes tumour formation. This oncogenic region of the T-DNA is entirely contained in the plasmid pPCV-311. This region of DNA contains four genes, that when expressed in plant cells are sufficient for tumour formation. The approximate coding regions of these four genes and the direction of transcription of these four genes are indicated in FIGS. 4A and 4B. The other portions of the vector pPCV 311 are not shown in that they are not relative to the following constructions. Additionally, the oncogenic region of the Agrobacterium strain C58 is located on the T-DNA plasmid within that bacterium, commonly referred to as the wild-type nopaline plasmid. A nearly identical oncogenic region is also found in wild type octopine strains which could also be used as a source of genes. The complete nucleotide sequence of an octopine strain oncogenic region is described by Barker et al., Plant Molecular Biology 2:335–350 (1983). The partial sequence obtained from various constructs of genes derived from pPCV 311 was compared to the published nucleotide sequence.

Two genes were isolated from pPCV 311, the IamH and the IamS genes, commonly referred to as genes 2 and 1 respectively. The IamH gene was isolated by first subcloning the indicated Hind III fragment, a fragment that contains all of the coding region of gene 2 and additional 5' sequences that were subsequently removed for the construction of a promoterless version of the gene. The restriction sites mapped in this subclone are shown in FIGS. 4A and 4B and the subclone is referred to as pPAL G2. For the isolation of coding sequences only, pPAL G2 was first split into two smaller clones and the gene later reconstructed. The Xba I-Sma I and Sma I-Sma I fragments shown in FIGS. 4A and 4B were isolated by gel elution and subsequently cloned into the following vectors: The Sma I-Sma I fragment was cloned into pGEM 4Z, giving rise to pPAL 899. The Xba I-Sma I fragment was subcloned into pGEM 7Z, giving rise to pPAL 898. The 5' non-coding sequences of the IamH gene that are present in this subclone were removed in the following fashion: pPAL 898 was digested with Eco RI, the Eco RI site is in the promoter region of the clone, and in this subclone is the only Eco RI site. This digested DNA was then treated with Exonuclease III, and following digestion treated with S1 nuclease and the Klenow fragment of DNA polymerase I. The treated DNA was then cut with Pst I and treated with Klenow fragment in order to make the Pst I site blunt. The linear, digested, blunt ended plasmid was then relegated and used to transform *E. coli* DH5-alpha according to standard protocols. Subclones were chosen, sequenced and one subclone was chosen that was deleted to 8 nucleotides in front of the ATG start of translation codon. The ATG start codon was determined by comparison of the nucleotide sequence obtained from the deleted subclones to the nucleotide sequence for the octopine strain described by Barker, et al. Plant Molecular Biology 2:335–350 (1983). The nucleotide sequences of both the 5' non-coding and the coding region were nearly identical. This subclone was named pPAL 897, the ATG codon is shown in FIGS. 4A and 4B, the direction of transcription in this case would be from right to left in FIGS. 4A and 4B. The plasmid contained the 5' half of the coding region from the IamH gene, with the promoter sequences deleted.

The construction of the 3' half of the lamH gene, contained in the plasmid pPAL 898 was carried out as follows. A 3' region of the gene that contains the polyadenylation signal naturally found in the gene was isolated by digestion pPAL 898 with the enzymes Bam HI and Apa I. The digested DNA was treated with Klenow fragment to make it blunt ended and was religated. This gave rise to the subclone pPAL 896, which is a plasmid that contains the 3' half of the IamH gene. To reconstruct the intact lamH gene, pPAL 896 was digested with Hind III and Sma I, and the 3' half gene fragment was isolated by gel elution. pPAL 897 was digested with Sma I and Hind III and the isolated 3' fragment from pPAL 896 was cloned into these sites, reconstructing a promoterless version of the gene that contains the indicated array of restriction sites flanking the gene. This plasmid was named pPAL 895 and is shown in FIGS. 4A and 4B.

Example 9

Figure 3:
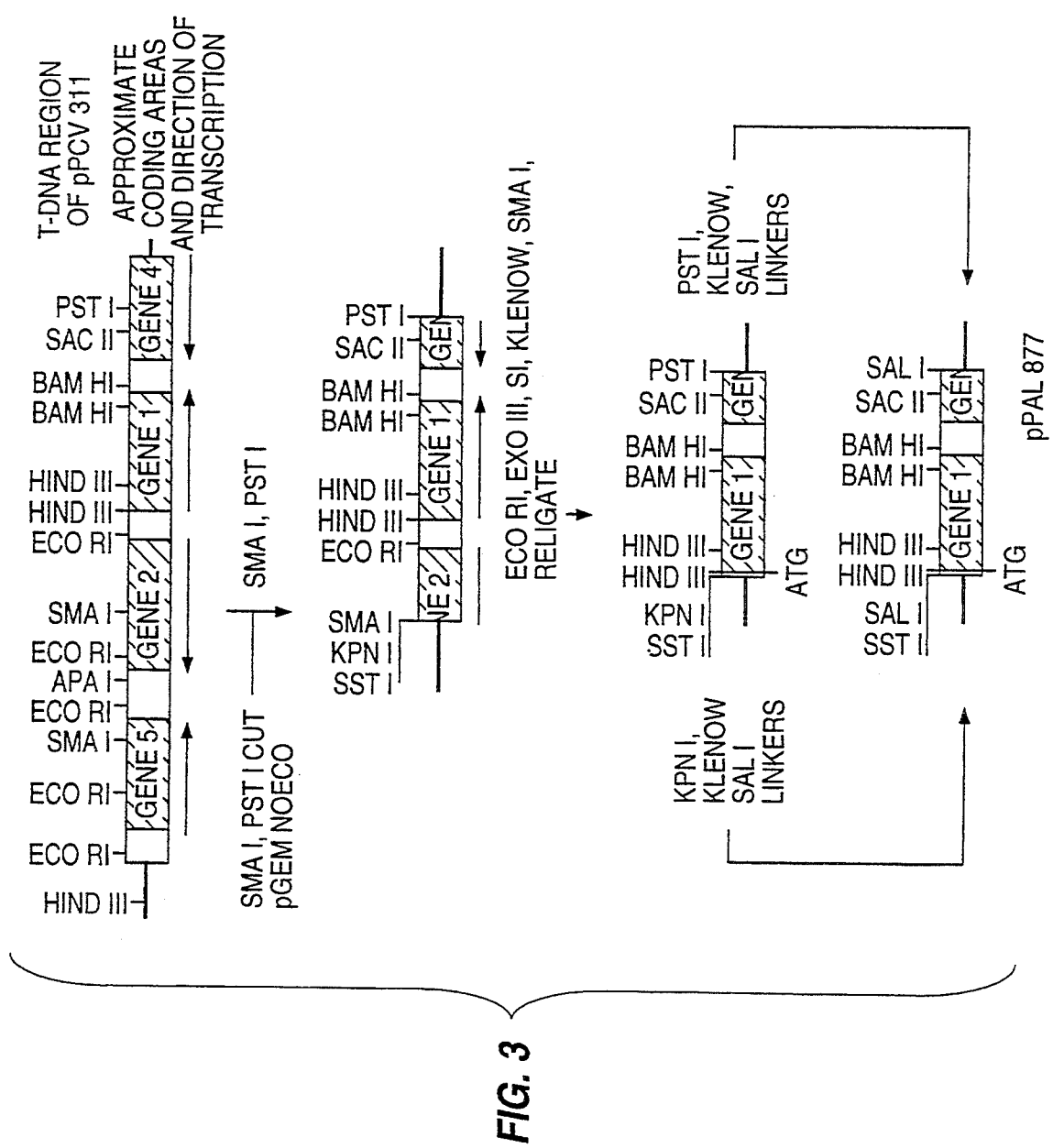
FIG. 3 illustrates the procedure used for the isolation of the T-DNA gene 1 (the IamS: indole acetamide synthase gene) of the *Agrobacterium tumefaciens* Ti plasmid derivative pPCV 311 and the construction of a promoterless version of this gene.

This example describes the isolation and construction of a promoterless version of the gene 1, IamS: indole acetamide synthase gene of the Ti plasmid of the Agrobacterium tumefaciens strain C58 which procedure is summarized in FIG. 3. The gene was isolated from the plasmid pPCV311. The Sma I-Pst I fragment that contains 5' and 3' regions of the IamS gene as well as the coding region was isolated by gel elution and subcloned into a derivative of pGEM 4Z called pGEM-noEco. pGEM-noEco is a plasmid from which the Eco RI site of pGEM 4Z has been removed by cutting with Eco RI and making blunt ended and relegating such that only the Eco RI site was removed. The fragment was inserted in the orientation shown relative to the polylinker. This subclone was called pPAL 889. pPAL 889 was digested with Eco RI, and briefly treated with Exonuclease III, followed by S1 nuclease. The DNA was digested with Sma I and treated with Klenow fragment to make it blunt ended. The DNA was relegated and clones recovered. Some of these clones were chosen, sequenced, and one clone was found which had 5' sequences deleted such that only approximate 15 bases upstream of the ATG start of translation codon remained. This plasmid was named pPAL 888. The Kpn I site at the 5' end of the gene as well as the Pst I site at the 3' end of the gene were both converted to Sal I sites by cutting with Kpn I, end filling with Klenow and adding synthetic Sal I linkers, and repeating the linker addition at the Pst I site such that the entire gene can be excised as a single Sal I fragment. This plasmid was named pPAL 887. This plasmid contains the promoterless version of the IamS gene and contains the array of restriction sites shown that flank the gene as shown in FIG. 3.

Example 10

In this example, a pollen specific promoter is used to synthesize the enzyme IamH specifically in pollen cells. The enzyme has activity that can cause the production of NAA from NAM, the substance NAA functioning as a plant hormone that is substantially toxic to developing pollen grains, while the precursor NAM being relatively non-toxic. For this example, the IamH gene was inserted into the vector PAL 1423. The IamH gene was isolated from pPCV311 as described in FIGS. 4A and 4B and cloned as a Sal I fragment in the Sal I site of PAL 1423, creating PAL 1426. This vector has the IamH gene (T-DNA gene 2) under the control of a pollen specific promoter from clone L4 in the sense orientation. PAL 1426 was used to transform Tobacco as outlined in Example 1.

Example 11

In this example, we use a pollen specific promoter to synthesize the enzyme IamH specifically in pollen cells. The enzyme has activity that can cause the production of NAA from NAM, the substance NAA functioning as a plant hormone that is substantially toxic to developing pollen grains, while the precursor NAM being relatively non-toxic. For this example, the IamH gene was inserted into the vector PAL 1423. The IamH gene was isolated from pPCV311 as described in FIGS. 4A and 4B and cloned as a Bam HI-Sst I fragment in the Bam HI-Sst I sites of PAL 1423, creating PAL 1424. This vector has the IamH gene (T-DNA gene 2) under the control of a pollen specific promoter from clone L4. PAL 1424 was used to transform Tobacco as outlined in example 1.

Example 12

In this example, two isogenic plant lines (A1, A2) were produced that carried either the IamS or the IamH genes. Tobacco plants were transformed with PAL 1426 containing the IamH gene as in Example 4, producing the A2 line. The IamS gene described in FIG. 3 was inserted as a Sal I fragment into the vector PAL 1423 in the sense orientation, giving rise to PAL 1425. PAL 1425 was used to transform tobacco as described and tobacco plants were produced that carried PAL 1425. These lines represented the A1 lines. Tobacco plants that contained both PAL 1426 and PAL 1425 were selfed and homozygous A1 and A2 lines were selected.

Example 13

In this example, PAL 1426 (see Example 10) and PAL 1425 were used to transform *Brassica napus*. Plants lines homozygous for the A1 and A2 genes were selected as in Example 6.

Example 14

In this example, tobacco pollen was harvested from control tobacco plants and from tobacco plants transformed with gene 2 of *Agrobacterium tumefaciens*, namely the IamH gene, as described in Examples 1 and 10, using PAL 1426. The pollen was then germinated in vitro on matrices containing either NAM or NAA in various concentrations.

In reference to Table 2, pollen from neither the control plants nor the transformed plants germinated in the presence of NAA, which is cytotoxic. The data shown in Table 2 is expressed as the percentage of pollen grains that germinated.

Both control and transformed pollen germinated in the absence of NAA and NAM.

In the presence of NAM, the germination of pollen from control plants was only inhibited at the highest concentration tested (50 ug/ml). By contrast, the germination of pollen from transformed plants was significantly inhibited at all concentrations of NAM tested. Furthermore, pollen tubes that did develop were less than 20% of the length of pollen tubes formed under control conditions. This indicates that the IamH gene is being expressed and that the gene product IamH is functional in transformed plants.

The present invention has been described in detail and with particular reference to the preferred embodiments; however, it will be understood by one having ordinary skill in the art that changes can be made thereto without departing from the spirit and scope thereof.

TABLE 1

| Transient Male Sterility Actuating Agent | Plant Line A2 | Plant A1 |
| --- | --- | --- |
| non toxic substance inducing molecule | psp + IamH | cp + IamS |
| | psp + IamH | psp + IamS |
| | psp + IamH and ip + IamS | psp + IamS |
| | psp + IamH and ip + IamS | cp + IamS |
| | ip IamH and psp + IamS | psp + IamH |
| | ip IamH and psp + IamS | cp + IamH |
| toxic molecule | cp + crg + psp + anti-sense to crg and psp + IamH | psp + IamS |
| | cp + crg + psp + anti-sense to crg and psp + IamH | cp + IamS |

TABLE 1-continued

| Transient Male Sterility Actuating Agent | Plant Line A2 | Plant A1 |
|---|---|---|
| | cp + crg + psp + anti-sense to crg and cp + IamH | psp + IamS |

Notes: psp = pollen specific promoter; cp = consitutive promoter; ip = inducible promoter; + = A plus sign between a specified promoter and a specified gene indicates that the promoter regulates the expression of the specified gene; crg = a gene conferring a chemical resistance.

TABLE 2

| Plant | NAA concentration (μg/ml) | | | | NAM concentration (μg/ml) | | | |
|---|---|---|---|---|---|---|---|---|
| | 0 | 12.5 | 25 | 50 | 0 | 12.5 | 25 | 50 |
| 501 | 100 | 0 | 1* | 0 | 100 | 45* | 10* | 0 |
| 503 | 100 | 0 | 0 | 0 | 100 | 70* | 36* | 0 |
| 507 | 84 | 0 | 0 | 0 | 84 | 2.5* | 0 | 0 |
| 508 | 100 | 0 | 0 | 0 | 100 | 51 | 0 | 0 |
| Control | 82 | 0 | 0 | 0 | 82 | 65 | 72 | 0 |

*pollen tubes were less than 20% of control length

---

We claim:

1. A method of producing seed of a male sterile plant, comprising:

(a) producing a male sterile plant line by a procedure comprising the steps of (i) introducing into the genome of one or more plant cells of a pollen-producing plant a isolated first recombinant DNA molecule comprised of (A) a DNA sequence that encodes a gene product which, when produced in a cell of a plant, said cell being essential to pollen formation or function, is capable of rendering an externally applied non-toxic substance cytotoxic to said cell and (B) a first promoter operably linked to said DNA sequence, (ii) selecting a plant cell into which the first recombinant DNA molecule is stably integrated, (iii) regenerating from the selected plant cell a plant which carries the male sterile trait, (iv) increasing the number of plants which carry the male sterile trait to produce a plant line having plants carrying the male sterile trait and (v) rendering plants of said plant line transiently male sterile by hand or by exposing said plants to an externally applied non-toxic substance wherein said first promoter is a pollen specific promoter;

(b) producing a male fertile second plant line by a procedure comprising the steps of (i) introducing into the genome of one or more plant cells an isolated second recombinant DNA molecule comprised of (A) a second DNA sequence encoding a second gene product which is capable of converting a substance which is endogenous to cells of said second plant line, to said non-toxic substance, and (B) a second promoter operably linked to said second DNA sequence, (ii) selecting a plant cell into which the second recombinant DNA molecule is stably integrated, (iii) regenerating from the selected plant cell a plant which carries said second recombinant DNA molecule and (iv) increasing the number of plants which carry said second recombinant DNA molecule;

(c) cross-pollinating plants of said male sterile first plant line with plants of said male fertile second plant line; and then (d) harvesting seed of plants of said male sterile line.

2. The method according to claim 1, wherein said non-toxic substance is a chemical agent selected from the group consisting of 2-amino-4-methoxy butanoic acid, a non-toxic analog of glucuronic acid, naphthalene acetamide and indole acetamide.

3. The method according to claim 1, wherein said first recombinant DNA molecule comprises a selection marker gene which encodes a selection gene product which permits the selection of a plant having said first recombinant DNA molecule integrated into its genome.

4. The method according to claim 1, wherein said second promoter is a pollen specific promoter or a regulatable promoter.

5. The method according-to claim 1, wherein said second recombinant DNA molecule comprises a selection marker gene which encodes a selection gene product which permits the selection of a plant having said first recombinant DNA molecule integrated into its genome.

6. The method according to claim 1, wherein said first DNA sequence encodes indole acetamide hydrolase (IamH) and said second DNA sequence encodes indole acetamide synthase (IamS).

7. The method according to claim 1, wherein each of said first and second promoters is a pollen specific promoter.

8. The method according to claim 1, wherein said first and second recombinant DNA molecules are incorporated into homologous chromosome pairs, and wherein plants of said second plant line are not capable of rendering the non-toxic substance cytotoxic to cells of plants of said second line which are essential to pollen formation or function.

9. The method according to claim 1, wherein the seed produced by the male sterile plant line has said first and second recombinant DNA molecules located on opposite chromatids of the same chromosome pair such that segregation of said first and said second recombinant DNA molecules occurs during meiosis.

10. The method according to claim 9, wherein said first and second recombinant DNA molecules are located on opposite chromatids of the same chromosome pair at substantially the same genetic locus such that segregation of said first and said second recombinant DNA molecules occurs during meiosis and the chance of recombination of the first and second recombinant DNA molecules to the same chromatid during meiotic crossing over is substantially reduced.

11. The method according to claim 1, wherein the steps of increasing the number of male sterile plants which carry said first recombinant DNA molecule and the number of male fertile plants which carry the second recombinant DNA molecule results in the production of plants which are isogenic for said recombinant DNA molecules.

12. A method of using the seed obtained using the method claimed in claim 1, comprising crossing a plant grown from said seed with a plant of another line to produce F1 seed.

13. The method according to claim 1, wherein said promoter is a pollen specific promoter selected from the group comprising a promoter sequence of a gene from *Brassica napus* which selectively regulates the expression of a DNA sequence in the cells or tissues critical to pollen formation or function.

14. The method according to claim 13 wherein said promoter comprises a promoter sequence of a gene in clone L4, (SEQ. NOS. 3 and 4) L10, (SEQ. NOS. 5 and 6), L16 (SEQ. NOS. 1 and 2) or L19 (SEQ. NOS. 7 and 8).

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 3293 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: join(3..125, 690..1796, 1913..2209)

( x i ) SEQUENCE DESCRIPTION: SEQ ID NO:1:

```
GA ATT CCT CAA CAN NTG ATT CTC ATC AAC GGA CAG TTC CCT GGT CCT        47
   Ile Pro Gln Xaa Xaa Ile Leu Ile Asn Gly Gln Phe Pro Gly Pro
   1               5                   10                  15

AAC CTA AAC TCC ACA TCC AAC AAC AAT GTC GTC ATC AAT GTT TTC AAC        95
Asn Leu Asn Ser Thr Ser Asn Asn Asn Val Val Ile Asn Val Phe Asn
            20                  25                  30

AAC CTT GAC GAG CCT TTC CTC TTG ACC TGG TTAGTCACCA TTTCCTCTCA         145
Asn Leu Asp Glu Pro Phe Leu Leu Thr Trp
        35                  40

TTTTATAGGC ATTCTGTTTC TAAAATTTAA ATGATATTTT AAAGCTACAA TTTTTTTTTC     205

ATTTTTAATA TAACTGTTCT TTTACAAAGG CCAAACGAGA AATGCAAATG GAAAGTTCTC     265

ATTTCGTTTG ATATTTTCAT TTACAGTTAA CATATGATTT TTTTTTTCAG ATCTTTGTAG     325

GTTTGTTTGA AAAAAGTTTT GGTATAGTTA TGTTATTTTG TTTCCTGGAT CTTAGGTTTG     385

AATAATTCAT AACCAAATTG AAAACAAAAA CTTTTGGATC GTTAATCAAA TCTTCTTCTT     445

ATTTTTTAAA TGTTATATTA ATTTCACATA ATTACATCTA TATATAATAT ATAAATACAA     505

ATAAAATGAT AATTTCAGTT TATCATATAT TAAATCAGAC TAAAATAATA AAAACAAAAA     565

GAAATTTAAA CACATTTTGA CTCAGTTTTA GATTAAGATT GGTTATATTA CCACAAGTAA     625

TTATGCTAGT CTTCATTGCA AATTTAAACA CATTTTAACT ATGTGGGTTC GGTGACATGG     685

CAGG AGT GGT CTC CAG CAC AGG AAG AAC TCA TGG CAA GAT GGT GTG ACC     734
     Ser Gly Leu Gln His Arg Lys Asn Ser Trp Gln Asp Gly Val Thr
         45                  50                  55

GGA ACC TCA TGC CCA ATC CCA GCA GGC ACC AAC TAC ACT TAC CAT TTC       782
Gly Thr Ser Cys Pro Ile Pro Ala Gly Thr Asn Tyr Thr Tyr His Phe
        60                  65                  70
```

-continued

| | | | | | | | | | | | | | | | | |
|---|---|---|---|---|---|---|---|---|---|---|---|---|---|---|---|---|
| CAG | CCT | AAG | GAC | CAG | ATC | GGT | AGC | TAC | TTC | TAC | TAC | CCA | TCA | ACC | GCC | 830 |
| Gln | Pro | Lys | Asp | Gln | Ile | Gly | Ser | Tyr | Phe | Tyr | Tyr | Pro | Ser | Thr | Ala | |
| | | 75 | | | | | 80 | | | | | 85 | | | | |
| CTG | CAC | CGT | TTC | TCC | GGT | GGT | TTC | GGT | GGC | CTC | CGT | GTC | AAC | AGC | CGT | 878 |
| Leu | His | Arg | Phe | Ser | Gly | Gly | Phe | Gly | Gly | Leu | Arg | Val | Asn | Ser | Arg | |
| | 90 | | | | 95 | | | | | 100 | | | | | | |
| CTC | CTC | ATC | CCC | NTC | CCT | TAC | GCT | GAC | CCC | GAA | GAT | GAC | CAC | ACC | ATC | 926 |
| Leu | Leu | Ile | Pro | Xaa | Pro | Tyr | Ala | Asp | Pro | Glu | Asp | Asp | His | Thr | Ile | |
| 105 | | | | 110 | | | | | 115 | | | | | 120 | | |
| CTC | ATC | AAC | GAC | TGG | TAC | ACC | AAG | AGC | CAC | ACC | GCT | CTC | AAG | ACC | TTC | 974 |
| Leu | Ile | Asn | Asp | Trp | Tyr | Thr | Lys | Ser | His | Thr | Ala | Leu | Lys | Thr | Phe | |
| | | | | 125 | | | | | 130 | | | | | 135 | | |
| CTT | GAC | AGC | GGC | CGC | ACT | CTT | GGT | TCC | CCT | GAC | GGT | GTC | CTC | ATC | AAC | 1022 |
| Leu | Asp | Ser | Gly | Arg | Thr | Leu | Gly | Ser | Pro | Asp | Gly | Val | Leu | Ile | Asn | |
| | | | 140 | | | | | 145 | | | | | 150 | | | |
| GGA | AAG | TCC | GGT | AAA | GTC | GGA | GGA | CAA | AAC | AAG | CCT | CTC | TTC | ACC | ATG | 1070 |
| Gly | Lys | Ser | Gly | Lys | Val | Gly | Gly | Gln | Asn | Lys | Pro | Leu | Phe | Thr | Met | |
| | | 155 | | | | | 160 | | | | | 165 | | | | |
| AAG | CCA | GGA | AAG | ACC | TAC | AAG | TAC | AGA | ATC | TGT | AAC | GTT | GGG | TTC | AAA | 1118 |
| Lys | Pro | Gly | Lys | Thr | Tyr | Lys | Tyr | Arg | Ile | Cys | Asn | Val | Gly | Phe | Lys | |
| 170 | | | | | 175 | | | | | 180 | | | | | | |
| TCC | ACT | CTT | AAC | TTC | AGG | ATC | CAA | GGA | CAC | AAG | ATG | AAG | CTT | GTT | GAG | 1166 |
| Ser | Thr | Leu | Asn | Phe | Arg | Ile | Gln | Gly | His | Lys | Met | Lys | Leu | Val | Glu | |
| 185 | | | | | 190 | | | | | 195 | | | | | 200 | |
| ATG | GAA | GGA | TCT | CAC | GTT | CTC | CAG | AAC | GAC | TAC | GAC | TCG | CTC | GAC | GTC | 1214 |
| Met | Glu | Gly | Ser | His | Val | Leu | Gln | Asn | Asp | Tyr | Asp | Ser | Leu | Asp | Val | |
| | | | | 205 | | | | | 210 | | | | | 215 | | |
| CAC | GTC | GGA | CAG | TCG | TTC | GCT | GTT | CTT | GTG | ACC | GCT | GAC | CAA | GAG | GCC | 1262 |
| His | Val | Gly | Gln | Ser | Phe | Ala | Val | Leu | Val | Thr | Ala | Asp | Gln | Glu | Ala | |
| | | | 220 | | | | | 225 | | | | | 230 | | | |
| AAG | AGC | TAC | TAC | ATG | GTT | GCA | TCC | ACT | AGG | TTC | CTC | AAG | AAG | GAA | GTG | 1310 |
| Lys | Ser | Tyr | Tyr | Met | Val | Ala | Ser | Thr | Arg | Phe | Leu | Lys | Lys | Glu | Val | |
| | | 235 | | | | | 240 | | | | | 245 | | | | |
| AGC | ACT | GTT | GGT | GTG | ATG | AGC | TAC | GAA | GGA | AGC | AAT | GTT | CAG | CCT | TCA | 1358 |
| Ser | Thr | Val | Gly | Val | Met | Ser | Tyr | Glu | Gly | Ser | Asn | Val | Gln | Pro | Ser | |
| | 250 | | | | | 255 | | | | | 260 | | | | | |
| AAT | GTG | CTT | CCC | AAG | GCT | CCA | GTT | GGA | TGG | GCT | TGG | TCT | CTT | AAC | CAG | 1406 |
| Asn | Val | Leu | Pro | Lys | Ala | Pro | Val | Gly | Trp | Ala | Trp | Ser | Leu | Asn | Gln | |
| 265 | | | | | 270 | | | | | 275 | | | | | 280 | |
| TTC | AGA | TCA | TTC | AGA | TGG | AAC | TTA | ACC | GCC | AGC | GCG | GCT | AGG | CCT | AAC | 1454 |
| Phe | Arg | Ser | Phe | Arg | Trp | Asn | Leu | Thr | Ala | Ser | Ala | Ala | Arg | Pro | Asn | |
| | | | | 285 | | | | | 290 | | | | | 295 | | |
| CCG | CAA | GGA | TCT | TAC | CAT | TAC | GGA | AAG | ATC | AAC | ATC | ACA | CGT | ACC | ATC | 1502 |
| Pro | Gln | Gly | Ser | Tyr | His | Tyr | Gly | Lys | Ile | Asn | Ile | Thr | Arg | Thr | Ile | |
| | | | 300 | | | | | 305 | | | | | 310 | | | |
| AAG | CTC | GCC | AAC | ACC | AAG | AAC | TTG | GTG | GAC | GGT | AAG | GTC | AGG | TTT | GGG | 1550 |
| Lys | Leu | Ala | Asn | Thr | Lys | Asn | Leu | Val | Asp | Gly | Lys | Val | Arg | Phe | Gly | |
| | | 315 | | | | | 320 | | | | | 325 | | | | |
| CTT | AAC | GGT | GTA | TCA | CAC | GTT | GAC | ACC | NAG | ACT | CCC | TTG | AAG | CTT | GCT | 1598 |
| Leu | Asn | Gly | Val | Ser | His | Val | Asp | Thr | Xaa | Thr | Pro | Leu | Lys | Leu | Ala | |
| | 330 | | | | | 335 | | | | | 340 | | | | | |
| GAG | TAC | TTC | NAG | ATG | TCC | GAG | AAG | GTC | TTC | AAA | TAC | AAT | GTC | ATC | AAG | 1646 |
| Glu | Tyr | Phe | Xaa | Met | Ser | Glu | Lys | Val | Phe | Lys | Tyr | Asn | Val | Ile | Lys | |
| 345 | | | | | 350 | | | | | 355 | | | | | 360 | |
| GAC | GAA | CCA | GCA | GCC | AAG | ATC | ACT | ACA | CTA | ACC | GTT | GAG | CCT | AAT | GTC | 1694 |
| Asp | Glu | Pro | Ala | Ala | Lys | Ile | Thr | Thr | Leu | Thr | Val | Glu | Pro | Asn | Val | |
| | | | | 365 | | | | | 370 | | | | | 375 | | |
| CTT | AAC | ATC | ACT | TTC | CGT | ACC | TTT | GTT | GAA | ATC | GTC | TTC | GAG | AAC | CAC | 1742 |
| Leu | Asn | Ile | Thr | Phe | Arg | Thr | Phe | Val | Glu | Ile | Val | Phe | Glu | Asn | His | |
| | | | 380 | | | | | 385 | | | | | 390 | | | |
| GAG | AAG | AGC | ATG | CAA | TCA | TTC | CAT | TTG | GAT | GGT | TAC | TCC | TTC | TTC | TCA | 1790 |
| Glu | Lys | Ser | Met | Gln | Ser | Phe | His | Leu | Asp | Gly | Tyr | Ser | Phe | Phe | Ser | |

|  |  |  |  |  | 395 |  |  |  | 400 |  |  |  | 405 |  |  |
|---|---|---|---|---|---|---|---|---|---|---|---|---|---|---|---|

```
GTC  GCG  TAAGCTTCAT  TAATAACTCT  ATAGGCCAAT  GTTTCACTTA  NTANGCGCAG              1846
Val  Ala
     410

AACCGGCGTG  ATCTTTTACT  TCAGATATAA  GATTCCTAAC  AATTTTTTA  ATATTTTTC               1906

AACAGT  TCT  GAG  CCA  GGA  ACA  TGG  ACA  CCA  GAG  AAG  AGA  AAC  AAC  TAC       1954
        Ser  Glu  Pro  Gly  Thr  Trp  Thr  Pro  Glu  Lys  Arg  Asn  Asn  Tyr
                            415                          420

AAC  TTG  CTC  GAT  GCG  GTC  AGC  AGA  CAC  ACC  GTG  CAA  GTN  TTC  CCC  AAG     2002
Asn  Leu  Leu  Asp  Ala  Val  Ser  Arg  His  Thr  Val  Gln  Xaa  Phe  Pro  Lys
425                      430                      435                      440

TCG  TGG  TCC  GCC  ATC  CTC  TTG  ACA  TTC  GAC  AAC  GCC  GGT  ATG  TGG  AAC     2050
Ser  Trp  Ser  Ala  Ile  Leu  Leu  Thr  Phe  Asp  Asn  Ala  Gly  Met  Trp  Asn
                    445                      450                      455

ATC  AGA  TCA  GAG  AAC  TGG  GAG  AGA  AGA  TAC  TTG  GGA  CAG  CAA  ATG  TAC     2098
Ile  Arg  Ser  Glu  Asn  Trp  Glu  Arg  Arg  Tyr  Leu  Gly  Gln  Gln  Met  Tyr
               460                      465                      470

GTC  AGT  GTT  CTT  TCC  CCT  GAG  AAA  TCA  CTA  AGA  GAC  GAA  TAC  AAC  ATC     2146
Val  Ser  Val  Leu  Ser  Pro  Glu  Lys  Ser  Leu  Arg  Asp  Glu  Tyr  Asn  Ile
          475                      480                      485

CCA  CTC  AAC  ACC  AAC  CTT  TGT  GGT  ATC  GTT  AAG  GGC  TTG  CCA  TTA  CCT     2194
Pro  Leu  Asn  Thr  Asn  Leu  Cys  Gly  Ile  Val  Lys  Gly  Leu  Pro  Leu  Pro
     490                      495                      500

ACA  CCC  TAC  ACT  ATT  TAATTAAACT  CACTTCCACA  AAAGTTTTAT  TTATTTATTT            2249
Thr  Pro  Tyr  Thr  Ile
505

GATATATGTA  AAATTCTACT  TTTTACAAGT  GAGTGTATTA  CGTGACTAAT  TAACCCTTTC             2309
CTAATTTCAT  TTAACATACT  ACTACTATAA  TTACAGATCC  CATTGTTGTT  TCACTAATAG             2369
TAATATATAC  AACATTTAGC  TTACTTAATA  TAATCCTGAT  CTAACACAA   AAGACTGTTA             2429
TTCATTTCAT  AATGAACAAA  ACTTGTTCAC  CCCCTATGGT  GAACCCTCTA  ATTCACCTCT             2489
ATTCTTAACA  CCAATCAAAT  TGACATGTAA  GATTAATAAA  AAAAGAAATA  AATTTAAAA              2549
GAAAAAAATA  GGTTTCCTAA  AAAAGGGTTT  ATTTGTCAAA  TAACCAAAAA  AAAATGAAAA             2609
TTANATTTTG  GGAGAGAGAG  TAGAGAGAGA  TAGGAANAAA  AAGTAGGAGA  GAGGAGAGAA             2669
TTTTAGTTAG  TTAGTGTATT  TAAGTTTTTT  TCATGTATAT  AGGGTGCAAT  TTCCCAAAAA             2729
AAAAAGTCTC  GGTTAACAAG  GAAAATAACG  TGTGTTTGT   TACGCCGTCC  ATCGACGTCT             2789
TCTTCTTTAT  AGCCCAGAGA  AGATAGAAAG  CTGAGTCTCC  AGTTCATGC   TTCCAAATCA             2849
AATTTCGATT  TCATCTTCTC  CAAATCAAAT  CAAGCCATGT  TGCCTTATGA  GTAGAAAGAG             2909
CGCTGATGGT  GGAGATGAAG  ATGATGGTAT  GGGATTCAAA  CTTGCAGGCC  CCAGGGAGGA             2969
AGAAGATGAC  TTACTTGTG   AACCAGNCTG  TGCCTAAAAT  TCAACAAAAG  AAACCGATGG             3029
CAATTGGAAA  TCAGACACTA  CAACTTGNTT  AAATAAAAC   GCTANTTGTA  ATGTATTCTT             3089
AGAATATAGA  CTTGCAAGTT  GATGAGAACT  CACTGATGCA  AGTGTCGTGA  TCTTTGATGT             3149
AGTAAGGTCA  CAGCAACAGA  CTTTTAATGT  ATTCTTAAAA  TATAGATTTG  CAAGTTCTTT             3209
GTTGTATTTC  TTCTTCTTCG  TGGGACATCT  GACCTGTAAA  TCAGAGATAT  AATCCCACCA             3269
AACCCAAGGT  TTCCTGGTTT  AATT                                                      3293
```

( 2 ) INFORMATION FOR SEQ ID NO:2:

( i ) SEQUENCE CHARACTERISTICS:
        ( A ) LENGTH: 509 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Ile | Pro | Gln | Xaa | Xaa | Ile | Leu | Ile | Asn | Gly | Gln | Phe | Pro | Gly | Pro | Asn |
| 1 | | | | 5 | | | | | 10 | | | | | 15 | |

| Leu | Asn | Ser | Thr | Ser | Asn | Asn | Asn | Val | Val | Ile | Asn | Val | Phe | Asn | Asn |
| | | | 20 | | | | | 25 | | | | | 30 | | |

| Leu | Asp | Glu | Pro | Phe | Leu | Leu | Thr | Trp | Ser | Gly | Leu | Gln | His | Arg | Lys |
| | | 35 | | | | | 40 | | | | | 45 | | | |

| Asn | Ser | Trp | Gln | Asp | Gly | Val | Thr | Gly | Thr | Ser | Cys | Pro | Ile | Pro | Ala |
| | 50 | | | | 55 | | | | | 60 | | | | | |

| Gly | Thr | Asn | Tyr | Thr | Tyr | His | Phe | Gln | Pro | Lys | Asp | Gln | Ile | Gly | Ser |
| 65 | | | | 70 | | | | | 75 | | | | | | 80 |

| Tyr | Phe | Tyr | Tyr | Pro | Ser | Thr | Ala | Leu | His | Arg | Phe | Ser | Gly | Gly | Phe |
| | | | | 85 | | | | | 90 | | | | | 95 | |

| Gly | Gly | Leu | Arg | Val | Asn | Ser | Arg | Leu | Leu | Ile | Pro | Xaa | Pro | Tyr | Ala |
| | | | 100 | | | | | 105 | | | | | 110 | | |

| Asp | Pro | Glu | Asp | Asp | His | Thr | Ile | Leu | Ile | Asn | Asp | Trp | Tyr | Thr | Lys |
| | | 115 | | | | | 120 | | | | | 125 | | | |

| Ser | His | Thr | Ala | Leu | Lys | Thr | Phe | Leu | Asp | Ser | Gly | Arg | Thr | Leu | Gly |
| | 130 | | | | | 135 | | | | | 140 | | | | |

| Ser | Pro | Asp | Gly | Val | Leu | Ile | Asn | Gly | Lys | Ser | Gly | Lys | Val | Gly | Gly |
| 145 | | | | | 150 | | | | | 155 | | | | | 160 |

| Gln | Asn | Lys | Pro | Leu | Phe | Thr | Met | Lys | Pro | Gly | Lys | Thr | Tyr | Lys | Tyr |
| | | | | 165 | | | | | 170 | | | | | 175 | |

| Arg | Ile | Cys | Asn | Val | Gly | Phe | Lys | Ser | Thr | Leu | Asn | Phe | Arg | Ile | Gln |
| | | | 180 | | | | | 185 | | | | | 190 | | |

| Gly | His | Lys | Met | Lys | Leu | Val | Glu | Met | Glu | Gly | Ser | His | Val | Leu | Gln |
| | | 195 | | | | | 200 | | | | | 205 | | | |

| Asn | Asp | Tyr | Asp | Ser | Leu | Asp | Val | His | Val | Gly | Gln | Ser | Phe | Ala | Val |
| | 210 | | | | | 215 | | | | | 220 | | | | |

| Leu | Val | Thr | Ala | Asp | Gln | Glu | Ala | Lys | Ser | Tyr | Tyr | Met | Val | Ala | Ser |
| 225 | | | | | 230 | | | | | 235 | | | | | 240 |

| Thr | Arg | Phe | Leu | Lys | Lys | Glu | Val | Ser | Thr | Val | Gly | Val | Met | Ser | Tyr |
| | | | | 245 | | | | | 250 | | | | | 255 | |

| Glu | Gly | Ser | Asn | Val | Gln | Pro | Ser | Asn | Val | Leu | Pro | Lys | Ala | Pro | Val |
| | | | 260 | | | | | 265 | | | | | 270 | | |

| Gly | Trp | Ala | Trp | Ser | Leu | Asn | Gln | Phe | Arg | Ser | Phe | Arg | Trp | Asn | Leu |
| | | 275 | | | | | 280 | | | | | 285 | | | |

| Thr | Ala | Ser | Ala | Ala | Arg | Pro | Asn | Pro | Gln | Gly | Ser | Tyr | His | Tyr | Gly |
| | 290 | | | | | 295 | | | | | 300 | | | | |

| Lys | Ile | Asn | Ile | Thr | Arg | Thr | Ile | Lys | Leu | Ala | Asn | Thr | Lys | Asn | Leu |
| 305 | | | | | 310 | | | | | 315 | | | | | 320 |

| Val | Asp | Gly | Lys | Val | Arg | Phe | Gly | Leu | Asn | Gly | Val | Ser | His | Val | Asp |
| | | | | 325 | | | | | 330 | | | | | 335 | |

| Thr | Xaa | Thr | Pro | Leu | Lys | Leu | Ala | Glu | Tyr | Phe | Xaa | Met | Ser | Glu | Lys |
| | | | 340 | | | | | 345 | | | | | 350 | | |

| Val | Phe | Lys | Tyr | Asn | Val | Ile | Lys | Asp | Glu | Pro | Ala | Ala | Lys | Ile | Thr |
| | | 355 | | | | | 360 | | | | | 365 | | | |

| Thr | Leu | Thr | Val | Glu | Pro | Asn | Val | Leu | Asn | Ile | Thr | Phe | Arg | Thr | Phe |
| | 370 | | | | | 375 | | | | | 380 | | | | |

| Val | Glu | Ile | Val | Phe | Glu | Asn | His | Glu | Lys | Ser | Met | Gln | Ser | Phe | His |
| 385 | | | | | 390 | | | | | 395 | | | | | 400 |

| Leu | Asp | Gly | Tyr | Ser | Phe | Phe | Ser | Val | Ala | Ser | Glu | Pro | Gly | Thr | Trp |
| | | | | 405 | | | | | 410 | | | | | 415 | |

| Thr | Pro | Glu | Lys | Arg | Asn | Asn | Tyr | Asn | Leu | Leu | Asp | Ala | Val | Ser | Arg |
| | | | 420 | | | | | 425 | | | | | 430 | | |

| His | Thr | Val | Gln<br>435 | Xaa | Phe | Pro | Lys | Ser<br>440 | Trp | Ser | Ala | Ile<br>445 | Leu | Leu | Thr |
|-----|-----|-----|-----|-----|-----|-----|-----|-----|-----|-----|-----|-----|-----|-----|-----|
| Phe | Asp<br>450 | Asn | Ala | Gly | Met | Trp<br>455 | Asn | Ile | Arg | Ser | Glu<br>460 | Asn | Trp | Glu | Arg |
| Arg<br>465 | Tyr | Leu | Gly | Gln | Gln<br>470 | Met | Tyr | Val | Ser | Val<br>475 | Leu | Ser | Pro | Glu | Lys<br>480 |
| Ser | Leu | Arg | Asp | Glu<br>485 | Tyr | Asn | Ile | Pro | Leu<br>490 | Asn | Thr | Asn | Leu | Cys<br>495 | Gly |
| Ile | Val | Lys | Gly<br>500 | Leu | Pro | Leu | Pro | Thr<br>505 | Pro | Tyr | Thr | Ile | | | |

( 2 ) INFORMATION FOR SEQ ID NO:3:

( i ) SEQUENCE CHARACTERISTICS:
        ( A ) LENGTH: 8585 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: join(308..370, 1136..1261, 6369..6428, 7198..7353)

( x i ) SEQUENCE DESCRIPTION: SEQ ID NO:3:

```
GAATTCTAAA AATAGCAATA ACTTTTTGAG AACATCAGAT TTATGTACAC GCATAGGACA      60

CATACCTTTT TATTTACTTA AAGGAAAATG AACGAGTCTA AATCTTCCAC ATGTTATATG     120

AGCAAAACAT GAATTTTTCT AAATTAGATT CGTTTAAATC AGAACATATT AATGTGAGTT     180

TCTTAAATTA GATTTTTAAT ATCTATATAT ACGTAAGAAT ACTTCTTATG TTTTAAAATA     240

AAAAATAGAA TACTTCATCT CTTTCCTAAA TTTTTAAGCC AATATCAATC CATTTCTATA     300

ATCTAAG ATG AAG AAA TCC CTT CAA CTC TCT TTT TCG TTC TTA ATT ATC       349
        Met Lys Lys Ser Leu Gln Leu Ser Phe Ser Phe Leu Ile Ile
          1               5                  10

TCC ATC ATT CTC TCA CAT GGT TTGTATTTTC ATCTTAATAT ATTGCATATA          400
Ser Ile Ile Leu Ser His Gly
 15              20

GTAATTCCAT AATAAATTGA TTATACTAAA ATTTGACTTT TAAATATTG TCAACCCCCA      460

TATAATAAAT TTATTTACT ATATAAAACA TAGCATTAAA TTATCTCTTT GTGTAAAATT     520

CATAACTTTG CAGAAGGCTA GAAAATATAG ATAGTATAGT CAGAAATGTT TGCGTTAAAA    580

TTGAAAGGAT CAACCATGGA GTATTTAAAT GTTTTTTATA CTTTATGCCA TTTATAATTT    640

TTTTAATGTA TGGGTTTATA TATGATGAAG AACTATTATG ATAAAATAAT ATTAAATAAT    700

TTCATTTTTA TCATCTATTT ATGAACATTT TGTCCTGCAC ATACAAATGA TTTAACCAAC    760

ATTTTTAATA ATATGGATGA ACTATAGCTC TTACGTAAAT TTATTTGATA TTTTTAATTA    820

AATTTATATA TTTTTATAGG TAATTTGTTA TGCTTTTCCA ATACATACAG TAGTTGTTAT    880

TAAAATATCA AAATTTAATA CGTAATGTTT ATTAATATGC ACACAATTCT TAAAACCATA    940

TTTTTAAAAA ATAATGTGTG ACCAACGAT ATGCTCATTT TTTTATTTAC TAGCAAAATA   1000

TATTTCTTTT CTTACTTATA ACGTTTAAAA AGAAATGTTA TTAAACATTT TTTGCTGATA    1060

AATAAATTTT ATATTTCATA AAATCTAAAT ATATTTTTA ACAATTAAAA TTTGAAATTT    1120

TTATATCTTA CAGGA ATG ATG GCA GAT GCG CAG AAA AAG AAT TGT CCT CAT    1171
              Met Met Ala Asp Ala Gln Lys Lys Asn Cys Pro His
                                 25                  30

AAA ATT CCA ATA AAA GGA AGT TAT TGT GCT CCA ACT ATA TGT TTG GAT      1219
Lys Ile Pro Ile Lys Gly Ser Tyr Cys Ala Pro Thr Ile Cys Leu Asp
```

|  |  |  |  |  |
|---|---|---|---|---|
| 35 | | 40 | | 45 |
| ATG TGT AAG | AAG CAA CAT | GGA ACT GTT | GGT AGT | TGT GCG GAA | 1261
| Met Cys Lys | Lys Gln His | Gly Thr Val | Gly Ser | Cys Ala Glu |
| 50 | | 55 | 60 | |

| | | | | |
|---|---|---|---|---|
| TAAAAATGAT | TTTGTAACTG | CGCTTGTAAG | TAAGGGTTCT | CACTAAGTGT TATGAATCTA | 1321
| GTAATGTCCA | ACCAAGTTT | TATATTATTT | CTTTTAACAA | TAAGTCTAAA TGTTTGTCTC | 1381
| AGATTTGTGG | ATCTATTTAT | AATAAATAAT | AATATGAATG | TTAAATAAAT ACAAATGTGT | 1441
| AAAACAAGAG | TGGACTATTA | ATAAATATA | TGATTACATT | ATTGTTAGAA GTAACCAATA | 1501
| TTACGTGTAA | ATCAAAATC | TTAAGACAAG | TTAAAAGAT | TGAGATGAAA TCACAACCAA | 1561
| TATTTAAATG | TGAGATAATC | AACTAACATG | TAATTTTGTA | CACATTGTAA AAAAAAAAA | 1621
| GCAAGAGTTC | ATTATCAAAC | AAGAAAGTGT | TAGAAAGAGC | AACAGATTCA TTGCAAGGGC | 1681
| AGTCTAGGTT | GAATTGGCTT | GACATAGGGA | AAATTGAAAG | CACTGTTTCT GAACATGACA | 1741
| ACGCTTGGTC | AGGAAGAACA | ATCTCACAAC | CAGAGTTTTG | GGTAGATTTC TCCAATGTCA | 1801
| TTATCAGGTA | CGAGTTATGA | GACTTCATCC | ACATCTCAGT | CCCAGTTCCC TTCTCAGGAA | 1861
| GTTTCCTTGA | GGAAGGAGGT | TATTACAGAA | AGCTAAGTTA | CATGAGCCTG ACATATCATG | 1921
| CAAGGGCAGT | CCCAACAAGA | AAATGTTAGA | AAGAGCAACA | TATCATGCAA GGACAGTCCA | 1981
| GGTTTGAATT | GGCTTGACAG | ATGGTTTGCA | GACATGCCAT | CTGAAGGTCC TACAAACTCA | 2041
| TCAGACAACG | AAGGAAAATT | GATAGCATTG | TTTCTGAACA | TGACAAAACT CTAGTCAGGA | 2101
| AGAAGAATCT | CACAACCAAA | GTTTTGGGTA | GAGCTCCTCC | AATGTCATCA TCAGCTACGA | 2161
| GTTCAAAGAC | TTCATCCACA | TCTTAGTCCC | CATTCTCTTC | TCATGAAGTT TCCTTTAGGA | 2221
| AAGAGGTTAT | TACAGAAAGC | CAAGTTACAT | GAGCCTAACA | CAATCTATCA AAGCTAAGAA | 2281
| GAGACGATTA | ACCATTATTC | TTCATCTTTT | TGTCCCAAAA | TCACTGTTTG AAAAGAAACA | 2341
| GTCCATGTCT | TACAACGAAG | ATGTGAATGT | AAAGCGTTGT | GCATGTTCGG ATCCATCTTG | 2401
| CAACCAGCAG | AGTTATCTAT | ATCCACATGC | TCAAGTAACA | AGGAAAAATA TGTGGGCAAA | 2461
| GAAGGTAAAG | TGAACATCGT | TTCATTAATT | CATTAAAGCA | TTTCAACACC TTGATGGTTC | 2521
| TAAATACACA | CAAAACACTG | ATTTATAGAT | ACATAAGCAA | CTTCTGTGTA TGTTCTTTTA | 2581
| CATACAAGTT | GGTATCAAGG | CTGTTGCAAT | GTTGTTGTTT | GACCACTTTT ATTATTTAAT | 2641
| AGTTAACTTT | TGATGCTTCT | AAGATAATAT | GTTCCTCCTA | ACTCTTGTCA ACATGAAAGA | 2701
| CCAATTAAAG | GTTTTGATTA | AATACATACT | AATTTTTTAA | TATAATCTTA AAGTTATGT | 2761
| TACGTGTGGG | ACATCCACCT | AATAAACTAT | AAATTTAAAT | AATAATGTTT GAAAAGGATT | 2821
| TTATTGACAT | TCCTTTAAAT | AAATTCATAA | TTTTAAAAAT | AGCGATAACT TTTTGAAAAC | 2881
| ATCAGAATTA | TGTACACGCA | GAGGACACAT | ACCTTTTTAT | TTACTTATAG AAAATGAAC | 2941
| GAGTCTAAAG | CTTCCACATG | TTATATGAGC | AAAACATGGA | TTTTTCTAAA TTAGATTCGT | 3001
| TTAAATCAGA | ACATATTAAT | GTAAGTTTCT | TAAATTAGAT | TTTTAATATG TATATATATG | 3061
| TAAAAATACT | TCTTTTTTT | TTTTTGTCA | TCAGCATTAC | AGATTTCTAA ATAAGTTACT | 3121
| TCTTATGTTT | TAACAAATAG | AATACTTCAT | CTCTTTCCTA | AATTTAAGT CAATATCAAT | 3181
| CCATTTCTAT | AATCCGAAGA | TGAAGAAATC | CCTTCATCTC | TAGAAAATAG GGTCAGAAAG | 3241
| TTTTGCGTTA | AAATTGAAAG | GATCATCCCT | GAAGTATTTA | TTTGTTTTTT TTATGCTTTA | 3301
| GTCCATTAAT | ATTTTTTAA | TGTATGGGTT | TATATATGAT | TAAGAACTTC CATGATAAAA | 3361
| TAATATTAAA | TAGTTTTATT | TCTTATCATC | TATTTATGAA | CGTTGTTCC TGCACACACA | 3421
| AATGATTTAA | CCAACATTTT | TCATAATATG | GATAAACTAT | AGTTCTTATG TAAATTTATG | 3481
| TGATATTTTA | ATTAGATTTA | TATATTTATA | GGTAATCTAT | TATGCTTTTC CAATACATAC | 3541

```
AGTAGTTGTT CTTAAAACAT CAAATTTTTA TATGTAATGT TTATTAATAT GCACACAATT    3601
CTTAAAACAA TATTTTCACA ACATAAAAAA ATAATGTTTG ACCAAACCAT ATGCTCATTT    3661
TCTTTATTTA CCGGCAAAAA CCATTTCTCC ATTTTTTTAC TTATAACGCT TAAGATAAAA    3721
AAATTATTAA ACAGTTTTTG TTGATAAATA AGTTTTATAT TTCAGAAAAT GTATTATATT    3781
TTCAAACAAT TAAAATTTGG GTTTTTATAT CTAACATAAA TGATGGCAGA AGCACAGAAA    3841
AATAATTGTC TTCATAAAAT TCCAATAAAA GGAAGCTAGT GCATTCCAAA TAAATGTTTG    3901
GCTATGTGTA AGAAGCAACA TGGAACTCTT GGTAGTTGTC CGGAAAAGA AATTTGTAGT     3961
TGTGCTTGTA AGTAAGGGTT CTCACTAAGT GTTATGAATC TAATAATGTC CAACCAAAGT    4021
TGTATATAAT TTTTTAACAA TAAATGTCTA AATGTTTGTC TCAGATTTGT GGATCTATTT    4081
ATAATAAATA ATAATATGAA TGTTAAATAA ATACAAATGT GTAAAAAAG ATTGGACTAT     4141
TAATAAAATA AATGATCACA TTATTATTAG ATGTAACCAA TATTGTGTAT AAGATCGTAA    4201
AAGCTTAAGA CGAGTTAAAA AGATAGAGAT GAAATCACAT CCAATATCTA AATGTGAGAT    4261
AATCAACTAA CATATAATTT TGTATATATT GTAAGATAAA ATAAAAATAA AAATTAAAAA    4321
GCAAGAGTTG ATTATCAAAC AAAGAAGTAT TAGAAAGAGC AACAGATCAT GCAAGAAGAG    4381
TCCATGTTTG AATTTCTTG ACAGATGGGT TGCAGACAAG TCATGGGAAG GTCATACAAA     4441
CTCATCAGAC AACGCAAAGA AAATTGATAG CACAGTTTCT GAACATGACA AGCTCTGGT     4501
CATGAAGAAC AATCTCACAA GCAGAGTTTT GGGTAGACCT CCTCCAATGT CATCATCAGC    4561
TACGAGCTCT GAGACTTCAT CCACATCTCA GTCCTCAGTT TCTTCCCAGG AAGTTTCCTT    4621
GAGGAAGGAG GTTATTACAG AAATCCAAGT TACATGAGCC TGGCAAAATC TATCAAAGCT    4681
AAGCAGAGAT GATCACGGTA TTCTTCATCG TCTTCTTCCA AAACCTGGTT TGAGAAAAAA    4741
CAATCCATGT CTTACAACAG AGATGTAAAT GTAAGTGTT GTGTTTGTTC GGATCAATCT     4801
TGCAACCAGT GGAGTGATCT ATATCGACCG GTTCAAGTAA CAAGGAGAAC TATGTGGGAA    4861
AGAGGCTAAA TTAAACATCG TTTCATCAAA GATTGTTGCA ATGTTGTTGT TTGGCCACTT    4921
TGATTATTTA ATAATTAACT TCGGATGCTT CTGAGACAAT CTGTTCCTCC CATTTTTGT     4981
CAATATGAAA CGAAGAGCAA TGCTTCATCT TTAGACATGA AAAGCCATTT AAATGACCAA    5041
ATAACATAGT TTATACCAAA GCTTCCTTAT AAATTTTACC CGTTCTAAAA ATTGCTCTTA    5101
CTATCAAAAT CTAAAACTGA ATTAAATTCA ATTATCTTAC TGTTACACAG TTTTCACTAA    5161
TCACTATTTT AATGTATAAA CTATAAAAAT AAATTAAATA CTTACTAAAT TTTTAGATTT    5221
AATCCATAAA TTATATTACA GTTCAGAGAT TTCATCCACA TTTCAGTCCC CAGTCCCTTA    5281
CTCATTAAAT TTTCCTGAGG AAGGAGGTTA TACAGAAAGT CAACTTACAT GAGCCTTACT    5341
CAATCTATCA AAGCTAAGAA GAGATGTCAG GTTCTTCTTC ATCTTCTGT TCCACATCAC     5401
CATTTAAGTA GAAACAGTAT ATGTCTTACA ACGGTGATGT GAATGTAAAG GGTTGTGCTG    5461
GTTCGGAGTA GACTGATCTA TATCCACCAG TGCAAGGAAC ATGGAGGCAT ATGTGGGCTA    5521
AAAAAAACAT CATTAACTGA ATCTTTAAAG CACTTTCAAC ATCTTGTTGG TTCCATGAAA    5581
TACATAAATG GATTATAGGT TATTGAAGCC ATTGTTGTAT ATGTTTCTTA CTTATAAATT    5641
AGTTTGAAGA CAGCAATGTT GTTGTTTGGC CACTTTGATT ATTTAATAAT TAACTTCTGA    5701
TCTTTCTGAG ACAATATGTT CCTCTTATTT CTTGTCAATA TGAAACCAAG AGCAAAGTTT    5761
CATCCTTAGA CATGAAAGGC TTATTAAATG ACCAAATAAC ATAGTTTAGA CGAAAGCTTC    5821
CTAATAAAAT TTATTCTCAC TATCTAAATC TAAAACTGAA TTCAATTCAT CTATCTGATT    5881
ATTATATAGT TTTCATTTTT TGTTATTTTA TTGAATGAGT AAAAAATTTA ATTAAATACT    5941
TACTATTTTT TTCATATAAT CTTATAAATT ATGTTACGTG TGGGACATCC ACCTAATAAC    6001
```

-continued

CTATTAATTT AAATAGTAAT ATTTGAAAAA TATTTTATTG ACATTGTTTT AAATAAATTC 6061

ATAATTCTAA AAATAGCAAT AACTTTTTGA AAACATCAGA TTTATGTACA CGCATAGGAC 6121

ACATACCTTT TTATTTACTT AAAGGAAAAT GAACGAGTCT AAAGCTTCCA CATGTTATCT 6181

GAGCAAAACA TGGATTTTTC TAAATTAGAT TCGTTTAAAT CAGAACATAT TAATGTGAGT 6241

TTCTTAAATT AGATTTTTAA TATGTATATA TACGTAAGAA TACTTCTTAT GTTTAAAAAA 6301

AAAAATAGAA TACTTTATCT CTTTCCTAAA TTTTTAAGCC AATATCAATC CATTTCTATA 6361

ATCCAAG ATG AAG AAA TCC CTT CAA CTC TCG TTT ACG TTC TTA ATT ATC 6410
Met Lys Lys Ser Leu Gln Leu Ser Phe Thr Phe Leu Ile Ile
65 70 75

TCC ATC ATT CTC TCA CAA GGTTTGTATT TACATCTTAA TATATTGCAT 6458
Ser Ile Ile Leu Ser Gln
80

ATAGTAATTC CATAATAAAT TGATTATACT AAACTTTGAC TTTTAAAATA TTGTAAACCC 6518

CCCATATAAT AAATTTTATT TACTATATAA AACATAGCAT TAAATTATCT CTTTGTGTAA 6578

AATTCATAAC TTTGCAGAAG GGAAGAAAAT ATAGAAAGTA TGGTCAGAAA TGTTTGCGTT 6638

AATATTGAAA GAATCAACCC TGAAGTATTT AACTGTTTTT TATACTTTAT GCCATTTATA 6698

ATTTTTTTAA TGTATGGGTT TATATATGAT GAAGAGCTAT TATGATAAAA TAATATTAAA 6758

TAGTTTCATT TTTATCATCT ATTTACGAAC ATTTTGTCTT GCACATACAA ATGATTTAAC 6818

CGACATTTTT CATAATATGG ATGAACTATA GTTCTTACGT AAATTTATTT GATATTTTTA 6878

ACTAATTTTA TATATTTTTA TGCTTTTCCA ATACATACAG TAGTTGTTCT TAAAATATCA 6938

AAATTTTATA CGTAATGTTT ATTAATATGC ACACAATTCT TAAAACCATA TTTTTCACAA 6998

AATAAAAAAT AAAGTGTGAC CAAACGATAT GCTCATTTTT TTTTATATAC TGGCAAAATA 7058

TATTTCTTTT TTTTTTTACT TATAACGTTT AAAATGAAAT GTTATTAAAC ATTTTTTGCT 7118

GATAAATAAA TTTTCTATTT CATAAAATCT ATATATATTT TCTAACAATT AAAATTTGAA 7178

ATTTTAATAT CTTACAGGA ATG ATG GCA GAT GCG CAG AAA AAG AAT TGT CCT 7230
Met Met Ala Asp Ala Gln Lys Lys Asn Cys Pro
85 90

CGT AAA ATT CCA ATA AAA GGA AGC TAT TGT GCT CCA ACT ATA TGT TTG 7278
Arg Lys Ile Pro Ile Lys Gly Ser Tyr Cys Ala Pro Thr Ile Cys Leu
95 100 105 110

GAT AAG TGT AAG AAG CAA CAT GGA ACT GTT GGT AGT TGT GCG GAA GAA 7326
Asp Lys Cys Lys Lys Gln His Gly Thr Val Gly Ser Cys Ala Glu Glu
115 120 125

AAA GGA TTT TGT AAC TGC GCT TGT AAG TAAGAGTTCT CACTAAGTGT 7373
Lys Gly Phe Cys Asn Cys Ala Cys Lys
130 135

AATGAATCTA GTAATGTCCA ACCAAAGTTT TATATTATTT CTTTTAACAA TAAGTCTAAA 7433

TGTTTGTCTC AGATTTGTGG ATCTATTTAT AATAAATATT AATATGAATG TTAAATAAAT 7493

ACAATTGTAT AAAACAAGAG TGGACTATTA ATAAAATATA TGATCACAGT ATTGTTAGAA 7553

GTAACCAATA TTACGTGTAA AATCAAAAGC TTAAGACTAG TTAAAAATAT AGAGATGAAA 7613

TCACAACCAA TATTTAAATG TTATATAATC AACTAACATG TAATTTTGTA CACATTGTAA 7673

AAAAAAAAAA AAAAAAAAAA AGCAAGAGTT GATTAACAAA CAAGAAAGTG TTAGAAAGAG 7733

CAACAGATCA TGCAAGAGCA GTCTAGGTTT GAATTGGCTT GACAGATGTG TTGCAGACAT 7793

GCCATGAGGA AGTCTTACAA ACTCATCAGA CAACACACAG AAAATTGATA GCATTGTTTC 7853

TGAACATGAC AAAGCTCTGG TCATGAAGAA AAATTTCACA GCCAAAGTTT TTGGTAGACC 7913

TTCTCCAGCT ACGAGTTTTG AGACTTCATC CACATCTCAG TCTCCATTTC CATTCTCATG 7973

AAGTTTTCTT TAGGGAAGAG GTTATTACAG AAAGCCAAGT TACATGAACC TAACACAATC 8033

| | | | | | |
|---|---|---|---|---|---|
| TATCAAAGGT | AAGAAGAGAC | GATCAACCAG | TATTCTTCAT | CTTCTTGTTC | CGAAATCACT | 8093
| GTTTGAAAAG | AAACAGTCAA | TGTCTTACAA | CGAAGATGTG | AATGTAAAGT | GTTGTGCATG | 8153
| TTCGGATCCA | TCTTGCACCC | AGTGGAATGA | TCTATATCTA | CATGCTCAAG | TAACAAGGAG | 8213
| AAATATGTGG | GCAAGAAGC | TAAAGTAAAC | ATTGTTTCAT | TAAATCTTTA | AAGCATTTCA | 8273
| ACACCTTGAG | AGTTCTAAAA | CACACACAAA | ATACCGATTT | ATAGATATAT | AAGCAACTTC | 8333
| TATGTATGTT | CTTTTACATA | CGAGTTAGTA | TGAAGACTGC | TGCAATGTTG | TTGTTTGACC | 8393
| ATTTTTATTA | TTTAATAGTT | AACTTCTGAT | GCTTCTAAAA | TAATATGTTC | TTCCCAACTC | 8453
| TTGTCAATAT | GAAACCAAGA | GCAAAGTTTT | AATTTTAGAC | ATGAAACGCC | TATTAAATGA | 8513
| CCAAATAACA | TAGTTTAGAC | GAAAACTTCC | TAATAAAATT | TATTCTCACT | ATCTAAATCT | 8573
| AAAACTGAAT | TC | | | | | 8585

( 2 ) INFORMATION FOR SEQ ID NO:4:

( i ) SEQUENCE CHARACTERISTICS:
        ( A ) LENGTH: 135 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Lys Lys Ser Leu Gln Leu Ser Phe Ser Phe Leu Ile Ile Ser Ile
 1               5                  10                  15

Ile Leu Ser His Gly Met Met Ala Asp Ala Gln Lys Lys Asn Cys Pro
            20                  25                  30

His Lys Ile Pro Ile Lys Gly Ser Tyr Cys Ala Pro Thr Ile Cys Leu
        35                  40                  45

Asp Met Cys Lys Lys Gln His Gly Thr Val Gly Ser Cys Ala Glu Met
    50                  55                  60

Lys Lys Ser Leu Gln Leu Ser Phe Thr Phe Leu Ile Ile Ser Ile Ile
 65                  70                  75                  80

Leu Ser Gln Met Met Ala Asp Ala Gln Lys Lys Asn Cys Pro Arg Lys
                85                  90                  95

Ile Pro Ile Lys Gly Ser Tyr Cys Ala Pro Thr Ile Cys Leu Asp Lys
            100                 105                 110

Cys Lys Lys Gln His Gly Thr Val Gly Ser Cys Ala Glu Glu Lys Gly
        115                 120                 125

Phe Cys Asn Cys Ala Cys Lys
    130                 135
```

( 2 ) INFORMATION FOR SEQ ID NO:5:

( i ) SEQUENCE CHARACTERISTICS:
        ( A ) LENGTH: 3641 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: join(854..1105, 1266..2375, 2463..2779)

( x i ) SEQUENCE DESCRIPTION: SEQ ID NO:5:

| | | | | | |
|---|---|---|---|---|---|
| TTTTTTCCAA | AACGAAACAC | ATATGCGAGC | CAGCNNCTAT | CACCCTCCGC | CACGTGCACA | 60
| AGGATCAACT | CCTTAAGCTC | CTTATCTACG | GACTCATCCT | TAGTTATCTT | AACCAAAATA | 120
| TTATTATAAA | ATTGCATAAT | CCATCGGTTT | AGCTGCTAAG | GACTCCCAAC | GTGCCTCCGT | 180

| | | |
|---|---|---|
| TGCATATGCT CTTATAAAAC TTAACTTAAG TGCCGCCTAA ACGGTCGTGT ATACCATTTT | 240 |
| CTTTGGAGTT AAGTCACTAT CTTCTTCATT TTCTTTCATC TATGTTTCTT TTGTTGGCCG | 300 |
| CGAATACAAT GATGTGGCGG ACTCCCTTGC GAAGTCTGCT CTCCAGAACT ATGTAGTAAA | 360 |
| CATTTTTCTT TTAGATTTAT TATTCAGTTG GTTGACAAAA AAAAGAGTG TTTAACCAAA | 420 |
| AAAACTAATA ATAATAATAA TAATAATAAT AATAGTTCTG TAAATTTATC AGTTTGCATG | 480 |
| TGAACTTCTT GAAATACATT CAAGTTATG TCTATAACTT ATTCACGTGA CTAATAGATT | 540 |
| TTTCTCTCTC AGAGTATTCT TTTAAAATCC AAAATAGCCA AATTCTCAAA GACATGGAAA | 600 |
| CCAAAGCCAA AAATTAGAAA AGGGAGAAAA ATGTTAAGAG AAACTAAAAA CACTAATAAT | 660 |
| AGCGAGAGGT TAAACTTCAA TGTTCCCAAA TATGGAAATG AATAGCGAAA TGAGAGGAGA | 720 |
| TGCCAAAGAA AATCAGAAAA AGCAGTCTTA AAAAACCCTA TAAAAACGTC CTCAAGCATT | 780 |
| TTCACAACTC GAAATTCAAA CCCCGAAACA TAACCAAATA AAAATAAAAC ATTAATACCC | 840 |

```
CACAAAAACA CAT ATG CGA GGG GTT AAA CTA TTG GCC GCG TGC CTC TAC        889
        Met Arg Gly Val Lys Leu Leu Ala Ala Cys Leu Tyr
         1               5                    10

CTG GCC GCA GCC GCA ACG GTG GTG GTC CAT GCC GAA GAC CCT TAC TTC        937
Leu Ala Ala Ala Ala Thr Val Val Val His Ala Glu Asp Pro Tyr Phe
     15              20                  25

CAC CAC GTA TGG AAC GTG ACC TAT GGA ACC GCT TCT CCT CTA GGC GTT        985
His His Val Trp Asn Val Thr Tyr Gly Thr Ala Ser Pro Leu Gly Val
 30              35                   40

CCA CAA CAA GTC ATT CTA ATC AAC GGC CAA TTC CCT GGT CCT AAC ATC       1033
Pro Gln Gln Val Ile Leu Ile Asn Gly Gln Phe Pro Gly Pro Asn Ile
45              50                  55                      60

AAC TCA ACC TCC AAC AAC AAT GTC ATC ATC AAC GTC TTC AAC AAC CTT       1081
Asn Ser Thr Ser Asn Asn Asn Val Ile Ile Asn Val Phe Asn Asn Leu
            65                  70                      75

GAT GAA CCC TTC CTC CTC ACT TGG TAATATTAAT AACCATTCAT TCATCTACAA      1135
Asp Glu Pro Phe Leu Leu Thr Trp
                80

ACATATCTTT TCTCTAGAAA AAAAAAAGAA CTCTTTAGCC ATGGTCGAAT CTAAAATTTA     1195
GAAAACATAA ACATAAGGAG TCTGATCATT TACATTATTA ATAAGTTATA ATATATTTTT     1255

GCATTTTAGG AAT GGA ATC CAG CAC AGG AAG AAC TGT TGG CAA GAT GGA        1304
          Asn Gly Ile Gln His Arg Lys Asn Cys Trp Gln Asp Gly
           85                  90                      95

ACT CCG GGG ACT ATG TGT CCG ATC ATG CCC GGC ACC AAC TAC ACT TAC       1352
Thr Pro Gly Thr Met Cys Pro Ile Met Pro Gly Thr Asn Tyr Thr Tyr
         100                 105                     110

CAT TTC CAG CCT AAA GAT CAG ATA GGA AGC TAC TTC TAC TAT CCC ACC       1400
His Phe Gln Pro Lys Asp Gln Ile Gly Ser Tyr Phe Tyr Tyr Pro Thr
 115                 120                     125

ACA GGG ATG CAC CGT GCC GCT GGT GGA TAT GGT GGA CTC CGA GTG AAC       1448
Thr Gly Met His Arg Ala Ala Gly Gly Tyr Gly Gly Leu Arg Val Asn
130             135                 140                         145

AGC CGT CTC CTC ATC CCG GTC CCT TAC GCT GAT CCC GAA GAT GAC TAC       1496
Ser Arg Leu Leu Ile Pro Val Pro Tyr Ala Asp Pro Glu Asp Asp Tyr
             150                 155                     160

ACT GTC CTC ATC GGT GAC TGG TAC ACT AAG AGC CAC ACC CAG TTG AAG       1544
Thr Val Leu Ile Gly Asp Trp Tyr Thr Lys Ser His Thr Gln Leu Lys
         165                 170                     175

AAG TTC CTC GAC GGT GGT CGT ACT ATT GGT CGT CCA GAC GGT ATT GTC       1592
Lys Phe Leu Asp Gly Gly Arg Thr Ile Gly Arg Pro Asp Gly Ile Val
 180                 185                     190

ATC AAC GGA AAG TCC GGA AAA GGT GAT GGA TCA GAC GCA CCG CTC TTC       1640
Ile Asn Gly Lys Ser Gly Lys Gly Asp Gly Ser Asp Ala Pro Leu Phe
195                 200                     205
```

| | | | | | | | | | | | | | | | | |
|---|---|---|---|---|---|---|---|---|---|---|---|---|---|---|---|---|
| ACC | TTG | AAG | CCT | GGA | AAG | ACT | TAC | AGG | GTT | AGG | ATC | TGT | AAC | GTG | GGT | 1688 |
| Thr | Leu | Lys | Pro | Gly | Lys | Thr | Tyr | Arg | Val | Arg | Ile | Cys | Asn | Val | Gly | |
| 210 | | | | 215 | | | | | 220 | | | | | | 225 | |
| GTC | AAG | ACA | TCT | ATC | AAC | TTT | AGG | ATT | CAG | AAT | CAC | AAG | ATG | AAG | CTC | 1736 |
| Val | Lys | Thr | Ser | Ile | Asn | Phe | Arg | Ile | Gln | Asn | His | Lys | Met | Lys | Leu | |
| | | | | 230 | | | | | 235 | | | | | 240 | | |
| GTT | GAA | ATG | GAA | GGA | TCG | CAC | GTT | CTT | CAA | AAC | GAT | TAC | GAC | TCT | CTT | 1784 |
| Val | Glu | Met | Glu | Gly | Ser | His | Val | Leu | Gln | Asn | Asp | Tyr | Asp | Ser | Leu | |
| | | | 245 | | | | | 250 | | | | | 255 | | | |
| GAC | GTT | CAC | GTT | GGC | CAG | TGC | TTT | GGC | ACC | ATC | GTT | ACC | GCG | AAT | CAA | 1832 |
| Asp | Val | His | Val | Gly | Gln | Cys | Phe | Gly | Thr | Ile | Val | Thr | Ala | Asn | Gln | |
| | | 260 | | | | | 265 | | | | | 270 | | | | |
| GAA | CCT | AAA | GAT | TAC | TAC | ATG | GTT | GCA | TCC | TCT | AGG | TTC | TTG | AAG | ACG | 1880 |
| Glu | Pro | Lys | Asp | Tyr | Tyr | Met | Val | Ala | Ser | Ser | Arg | Phe | Leu | Lys | Thr | |
| | 275 | | | | | 280 | | | | | 285 | | | | | |
| GTT | ATC | ACA | ACA | ACC | GGA | CTT | CTC | CGC | TAC | GAG | GGA | GGC | AAA | GGA | CCC | 1928 |
| Val | Ile | Thr | Thr | Thr | Gly | Leu | Leu | Arg | Tyr | Glu | Gly | Gly | Lys | Gly | Pro | |
| 290 | | | | | 295 | | | | | 300 | | | | | 305 | |
| GCC | TCT | TCA | CAG | CTT | CCG | GCT | GGT | CCG | GTC | GGA | TGG | GCC | TGG | TCG | TTG | 1976 |
| Ala | Ser | Ser | Gln | Leu | Pro | Ala | Gly | Pro | Val | Gly | Trp | Ala | Trp | Ser | Leu | |
| | | | | 310 | | | | | 315 | | | | | 320 | | |
| AAC | CAG | TTC | CGA | TCC | TTC | AGG | TGG | AAC | TTG | ACC | GCT | AGT | GCA | GCT | AGG | 2024 |
| Asn | Gln | Phe | Arg | Ser | Phe | Arg | Trp | Asn | Leu | Thr | Ala | Ser | Ala | Ala | Arg | |
| | | | 325 | | | | | 330 | | | | | 335 | | | |
| CCT | AAC | CCT | CAG | GGA | TCT | TAC | CAT | TAT | GGA | AAG | ATC | AAC | ATC | ACA | CGC | 2072 |
| Pro | Asn | Pro | Gln | Gly | Ser | Tyr | His | Tyr | Gly | Lys | Ile | Asn | Ile | Thr | Arg | |
| | | 340 | | | | | 345 | | | | | 350 | | | | |
| ACA | ATC | AAG | CTC | GTG | AAC | ACT | CAA | GGC | AAG | GTC | GAT | GGT | AAG | CTT | AGG | 2120 |
| Thr | Ile | Lys | Leu | Val | Asn | Thr | Gln | Gly | Lys | Val | Asp | Gly | Lys | Leu | Arg | |
| | 355 | | | | | 360 | | | | | 365 | | | | | |
| TTT | GCA | TTG | AAC | GGA | GTC | TCC | CAC | ACA | GAA | CCT | GAG | ACC | CCT | CTG | AAG | 2168 |
| Phe | Ala | Leu | Asn | Gly | Val | Ser | His | Thr | Glu | Pro | Glu | Thr | Pro | Leu | Lys | |
| 370 | | | | | 375 | | | | | 380 | | | | | 385 | |
| CTG | GCC | GAA | TAC | TTT | GGT | ATT | TCC | GAC | AAG | GTG | TTT | AAG | TAT | GAT | ACC | 2216 |
| Leu | Ala | Glu | Tyr | Phe | Gly | Ile | Ser | Asp | Lys | Val | Phe | Lys | Tyr | Asp | Thr | |
| | | | | 390 | | | | | 395 | | | | | 400 | | |
| ATC | ACC | GAT | GAC | CCT | ACC | CCG | GAA | CAG | ATC | AAA | AAC | ATC | AAG | ATC | GAG | 2264 |
| Ile | Thr | Asp | Asp | Pro | Thr | Pro | Glu | Gln | Ile | Lys | Asn | Ile | Lys | Ile | Glu | |
| | | | 405 | | | | | 410 | | | | | 415 | | | |
| CCT | AAC | GTT | CTT | AAC | ATC | ACT | CAC | CGT | ACC | TTC | GTC | GAG | GTG | GTG | TTT | 2312 |
| Pro | Asn | Val | Leu | Asn | Ile | Thr | His | Arg | Thr | Phe | Val | Glu | Val | Val | Phe | |
| | | 420 | | | | | 425 | | | | | 430 | | | | |
| GAG | AAC | CAC | GAG | AAG | AGT | GTT | CAG | TCT | TGG | CAC | TTG | GAT | GGT | TAT | TCT | 2360 |
| Glu | Asn | His | Glu | Lys | Ser | Val | Gln | Ser | Trp | His | Leu | Asp | Gly | Tyr | Ser | |
| | 435 | | | | | 440 | | | | | 445 | | | | | |
| TTC | TTC | TCC | GTT | GCG | TAAGTAAAAC | AAACACACAC | TTTGTTTCTT | GCATCACAAG | | | | | | | | 2415 |
| Phe | Phe | Ser | Val | Ala | | | | | | | | | | | | |
| 450 | | | | | | | | | | | | | | | | |
| TAACTCTTCA | TTTTAACCTA | ATTTTGACTT | TTACTATCTT | TTAAAGT | GTT | GAG | CCA | | | | | | | | | 2471 |
| | | | | | Val | Glu | Pro | | | | | | | | | |
| | | | | | 455 | | | | | | | | | | | |
| GGG | ACT | TGG | ACC | CCA | GAG | AAG | AGG | AAG | AAC | TAC | AAC | CTC | TTG | GAT | GCA | 2519 |
| Gly | Thr | Trp | Thr | Pro | Glu | Lys | Arg | Lys | Asn | Tyr | Asn | Leu | Leu | Asp | Ala | |
| | | 460 | | | | 465 | | | | | 470 | | | | | |
| GTG | AGC | AGA | CAC | ACA | GTT | CAA | GTC | TAC | CCA | AAG | TGC | TGG | GCA | GCA | ATC | 2567 |
| Val | Ser | Arg | His | Thr | Val | Gln | Val | Tyr | Pro | Lys | Cys | Trp | Ala | Ala | Ile | |
| | 475 | | | | | 480 | | | | | 485 | | | | | |
| TTG | CTC | ACA | TTT | GAT | AAC | TGT | GGA | ATG | TGG | AAC | GTT | CGT | TCT | GAG | AAC | 2615 |
| Leu | Leu | Thr | Phe | Asp | Asn | Cys | Gly | Met | Trp | Asn | Val | Arg | Ser | Glu | Asn | |
| 490 | | | | | 495 | | | | | 500 | | | | | 505 | |
| ACA | GAG | AGA | CGT | TAC | TTA | GGA | CAG | CAG | TTT | ACG | CCA | GTG | TCT | TGT | CTC | 2663 |
| Thr | Glu | Arg | Arg | Tyr | Leu | Gly | Gln | Gln | Phe | Thr | Pro | Val | Ser | Cys | Leu | |

|   |   |   |   |   |   |   |   |   |   |   |   |   |   |   |   |      |
|---|---|---|---|---|---|---|---|---|---|---|---|---|---|---|---|------|
|   |   |   |   | 510 |   |   |   | 515 |   |   |   | 520 |   |   |   |      |
| CAG | AGA | AAT | CAC | TTA | GAG | ATG | AAT | ACA | ACA | TGC | CTG | AGA | CAA | GCC | TCC | 2711 |
| Gln | Arg | Asn | His | Leu | Glu | Met | Asn | Thr | Thr | Cys | Leu | Arg | Gln | Ala | Ser |      |
|     |     | 525 |     |     |     |     | 530 |     |     |     |     |     | 535 |     |     |      |
| AAT | GTG | GTC | TCG | TCA | AAA | ACA | CAC | CTA | AAC | CTG | TTA | ACC | CTT | ACG | CTG | 2759 |
| Asn | Val | Val | Ser | Ser | Lys | Thr | His | Leu | Asn | Leu | Leu | Thr | Leu | Thr | Leu |      |
|     |     | 540 |     |     |     |     | 545 |     |     |     |     | 550 |     |     |     |      |
| GTG | CCT | AAG | TTT | AAC | TTTTAAATAC | AACTAAAGAG | TTTTGATTCT | TCTGTTGATC |   |   |   |   |   |   |   | 2814 |
| Val | Pro | Lys | Phe | Asn | Phe |   |   |   |   |   |   |   |   |   |   |      |
|     | 555 |     |     |     |     |   |   |   |   |   |   |   |   |   |   |      |

```
TGAAAATTAA TTTCTAAAAT TATATGGTTT ACTCGTATAT ACATGGAATT GAAAATGTAT  2874
GTATGTGTCT ATACCTTTTA AGTAATTTTT CTTTCTTTCA AGAAGCATTA GTCTTCTCTT  2934
TGTTTTTTGT TCTTCACTTT TTTGTAACAA TTATGTAATG TATTATGTAT CCATAATCTT  2994
CGATGAAATA AGCAAAAGAG ATCTTATTTC TCCCAAAAAA AAAACTTTAC AATAAAAGTA  3054
TTTCTCTATA GCCTAGAACC ATGTATGATG ATAACAAAAC CCTTCTTCTT AGTCTGAGCC  3114
TTTTTCTAAG GCTCTTTATC TCGTGGTTCT TCCACCAACG GAGTTTCCTT GAGAGAGAAG  3174
TCATCGAGGC TATCATCATT CTCTGTATCG ACCTGAACAA ACTCTTTGAA CATCGCCATT  3234
ACTTGAATCA TAGTTGGTCT TTTGAACGGT CGATCGTCCA GACACTGAGA CGCAATCTTC  3294
AAGTAATGAA ACAGCTCAAC GTCGCCAGAT TTCTCAGTTA TCAGGTCCGA ATCAAGAATC  3354
TCAGCTCCTC TACTCTCCTT ATAAAGCTGT TTAGCCCATC CACGAGATT  GTTGTCCTCA  3414
CCAAACTCCT CTGGATCGAT CGGTTTCTTC CCCGAGAGAA GCTCCAGAAG TATAACCCCG  3474
TAGCTATACA CATCTCCTTT GGTCGTGCAC CTGAAACTCT GGTAATACTC TGGCGGAACG  3534
TAACCGGGAG TTCCCGCGAG CGTGTCACGC TCAAATGCGT GTCCAGAGCG CTCACCAGCC  3594
TTGCCATACC GAAGTCCGAG ACGCGTGCTG TGAAGTCTTG GTCTAGA              3641
```

( 2 ) INFORMATION FOR SEQ ID NO:6:

( i ) SEQUENCE CHARACTERISTICS:
    ( A ) LENGTH: 559 amino acids
    ( B ) TYPE: amino acid
    ( D ) TOPOLOGY: linear ( i i ) MOLECULE TYPE: protein ( x i ) SEQUENCE DESCRIPTION: SEQ ID NO:6:

| Met | Arg | Gly | Val | Lys | Leu | Leu | Ala | Ala | Cys | Leu | Tyr | Leu | Ala | Ala | Ala |
|---|---|---|---|---|---|---|---|---|---|---|---|---|---|---|---|
| 1 |   |   |   | 5 |   |   |   |   | 10 |   |   |   |   | 15 |   |

| Ala | Thr | Val | Val | Val | His | Ala | Glu | Asp | Pro | Tyr | Phe | His | His | Val | Trp |
|---|---|---|---|---|---|---|---|---|---|---|---|---|---|---|---|
|   |   |   | 20 |   |   |   |   | 25 |   |   |   | 30 |   |   |   |

| Asn | Val | Thr | Tyr | Gly | Thr | Ala | Ser | Pro | Leu | Gly | Val | Pro | Gln | Gln | Val |
|---|---|---|---|---|---|---|---|---|---|---|---|---|---|---|---|
|   |   | 35 |   |   |   | 40 |   |   |   |   | 45 |   |   |   |   |

| Ile | Leu | Ile | Asn | Gly | Gln | Phe | Pro | Gly | Pro | Asn | Ile | Asn | Ser | Thr | Ser |
|---|---|---|---|---|---|---|---|---|---|---|---|---|---|---|---|
|   | 50 |   |   |   |   | 55 |   |   |   |   | 60 |   |   |   |   |

| Asn | Asn | Asn | Val | Ile | Ile | Asn | Val | Phe | Asn | Asn | Leu | Asp | Glu | Pro | Phe |
|---|---|---|---|---|---|---|---|---|---|---|---|---|---|---|---|
| 65 |   |   |   |   | 70 |   |   |   |   | 75 |   |   |   |   | 80 |

| Leu | Leu | Thr | Trp | Asn | Gly | Ile | Gln | His | Arg | Lys | Asn | Cys | Trp | Gln | Asp |
|---|---|---|---|---|---|---|---|---|---|---|---|---|---|---|---|
|   |   |   |   | 85 |   |   |   |   | 90 |   |   |   |   | 95 |   |

| Gly | Thr | Pro | Gly | Thr | Met | Cys | Pro | Ile | Met | Pro | Gly | Thr | Asn | Tyr | Thr |
|---|---|---|---|---|---|---|---|---|---|---|---|---|---|---|---|
|   |   |   | 100 |   |   |   |   | 105 |   |   |   | 110 |   |   |   |

| Tyr | His | Phe | Gln | Pro | Lys | Asp | Gln | Ile | Gly | Ser | Tyr | Phe | Tyr | Tyr | Pro |
|---|---|---|---|---|---|---|---|---|---|---|---|---|---|---|---|
|   |   | 115 |   |   |   |   | 120 |   |   |   | 125 |   |   |   |   |

| Thr | Thr | Gly | Met | His | Arg | Ala | Ala | Gly | Gly | Tyr | Gly | Gly | Leu | Arg | Val |
|---|---|---|---|---|---|---|---|---|---|---|---|---|---|---|---|
|   | 130 |   |   |   |   | 135 |   |   |   | 140 |   |   |   |   |   |

| Asn | Ser | Arg | Leu | Leu | Ile | Pro | Val | Pro | Tyr | Ala | Asp | Pro | Glu | Asp | Asp |
|---|---|---|---|---|---|---|---|---|---|---|---|---|---|---|---|

|     |     |     |     |     |     |     |     |     |     |     |     |     |     |     |     |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |
| Tyr | Thr | Val | Leu | Ile | Gly | Asp | Trp | Tyr | Thr | Lys | Ser | His | Thr | Gln | Leu |
|     |     |     |     | 165 |     |     |     |     | 170 |     |     |     |     | 175 |     |
| Lys | Lys | Phe | Leu | Asp | Gly | Gly | Arg | Thr | Ile | Gly | Arg | Pro | Asp | Gly | Ile |
|     |     |     | 180 |     |     |     |     | 185 |     |     |     | 190 |     |     |     |
| Val | Ile | Asn | Gly | Lys | Ser | Gly | Lys | Gly | Asp | Gly | Ser | Asp | Ala | Pro | Leu |
|     |     | 195 |     |     |     |     | 200 |     |     |     | 205 |     |     |     |     |
| Phe | Thr | Leu | Lys | Pro | Gly | Lys | Thr | Tyr | Arg | Val | Arg | Ile | Cys | Asn | Val |
|     | 210 |     |     |     |     | 215 |     |     |     |     | 220 |     |     |     |     |
| Gly | Val | Lys | Thr | Ser | Ile | Asn | Phe | Arg | Ile | Gln | Asn | His | Lys | Met | Lys |
| 225 |     |     |     |     | 230 |     |     |     |     | 235 |     |     |     |     | 240 |
| Leu | Val | Glu | Met | Glu | Gly | Ser | His | Val | Leu | Gln | Asn | Asp | Tyr | Asp | Ser |
|     |     |     |     | 245 |     |     |     |     | 250 |     |     |     |     | 255 |     |
| Leu | Asp | Val | His | Val | Gly | Gln | Cys | Phe | Gly | Thr | Ile | Val | Thr | Ala | Asn |
|     |     |     | 260 |     |     |     |     | 265 |     |     |     |     | 270 |     |     |
| Gln | Glu | Pro | Lys | Asp | Tyr | Tyr | Met | Val | Ala | Ser | Ser | Arg | Phe | Leu | Lys |
|     |     | 275 |     |     |     |     | 280 |     |     |     | 285 |     |     |     |     |
| Thr | Val | Ile | Thr | Thr | Thr | Gly | Leu | Leu | Arg | Tyr | Glu | Gly | Gly | Lys | Gly |
|     | 290 |     |     |     |     | 295 |     |     |     |     | 300 |     |     |     |     |
| Pro | Ala | Ser | Ser | Gln | Leu | Pro | Ala | Gly | Pro | Val | Gly | Trp | Ala | Trp | Ser |
| 305 |     |     |     |     | 310 |     |     |     |     | 315 |     |     |     |     | 320 |
| Leu | Asn | Gln | Phe | Arg | Ser | Phe | Arg | Trp | Asn | Leu | Thr | Ala | Ser | Ala | Ala |
|     |     |     |     | 325 |     |     |     |     | 330 |     |     |     |     | 335 |     |
| Arg | Pro | Asn | Pro | Gln | Gly | Ser | Tyr | His | Tyr | Gly | Lys | Ile | Asn | Ile | Thr |
|     |     |     | 340 |     |     |     |     | 345 |     |     |     |     | 350 |     |     |
| Arg | Thr | Ile | Lys | Leu | Val | Asn | Thr | Gln | Gly | Lys | Val | Asp | Gly | Lys | Leu |
|     |     | 355 |     |     |     |     | 360 |     |     |     | 365 |     |     |     |     |
| Arg | Phe | Ala | Leu | Asn | Gly | Val | Ser | His | Thr | Glu | Pro | Glu | Thr | Pro | Leu |
|     | 370 |     |     |     |     | 375 |     |     |     |     | 380 |     |     |     |     |
| Lys | Leu | Ala | Glu | Tyr | Phe | Gly | Ile | Ser | Asp | Lys | Val | Phe | Lys | Tyr | Asp |
| 385 |     |     |     |     | 390 |     |     |     |     | 395 |     |     |     |     | 400 |
| Thr | Ile | Thr | Asp | Asp | Pro | Thr | Pro | Glu | Gln | Ile | Lys | Asn | Ile | Lys | Ile |
|     |     |     |     | 405 |     |     |     |     | 410 |     |     |     |     | 415 |     |
| Glu | Pro | Asn | Val | Leu | Asn | Ile | Thr | His | Arg | Thr | Phe | Val | Glu | Val | Val |
|     |     |     | 420 |     |     |     |     | 425 |     |     |     |     | 430 |     |     |
| Phe | Glu | Asn | His | Glu | Lys | Ser | Val | Gln | Ser | Trp | His | Leu | Asp | Gly | Tyr |
|     |     |     | 435 |     |     |     |     | 440 |     |     |     |     | 445 |     |     |
| Ser | Phe | Phe | Ser | Val | Ala | Val | Glu | Pro | Gly | Thr | Trp | Thr | Pro | Glu | Lys |
|     | 450 |     |     |     |     | 455 |     |     |     |     | 460 |     |     |     |     |
| Arg | Lys | Asn | Tyr | Asn | Leu | Leu | Asp | Ala | Val | Ser | Arg | His | Thr | Val | Gln |
| 465 |     |     |     |     | 470 |     |     |     |     | 475 |     |     |     |     | 480 |
| Val | Tyr | Pro | Lys | Cys | Trp | Ala | Ala | Ile | Leu | Leu | Thr | Phe | Asp | Asn | Cys |
|     |     |     |     | 485 |     |     |     |     | 490 |     |     |     |     | 495 |     |
| Gly | Met | Trp | Asn | Val | Arg | Ser | Glu | Asn | Thr | Glu | Arg | Arg | Tyr | Leu | Gly |
|     |     |     | 500 |     |     |     |     | 505 |     |     |     |     | 510 |     |     |
| Gln | Gln | Phe | Thr | Pro | Val | Ser | Cys | Leu | Gln | Arg | Asn | His | Leu | Glu | Met |
|     |     |     | 515 |     |     |     |     | 520 |     |     |     |     | 525 |     |     |
| Asn | Thr | Thr | Cys | Leu | Arg | Gln | Ala | Ser | Asn | Val | Val | Ser | Ser | Lys | Thr |
|     |     | 530 |     |     |     |     | 535 |     |     |     |     | 540 |     |     |     |
| His | Leu | Asn | Leu | Leu | Thr | Leu | Thr | Leu | Val | Pro | Lys | Phe | Asn | Phe |     |
| 545 |     |     |     |     | 550 |     |     |     |     | 555 |     |     |     |     |     |

( 2 ) INFORMATION FOR SEQ ID NO:7:

( i ) SEQUENCE CHARACTERISTICS:
( A ) LENGTH: 4977 base pairs (B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: join(2158..3225, 3663..4046)

(xi) SEQUENCE DESCRIPTION: SEQ ID NO:7:

```
GGATCCGTTC CTTTCCGGTC ATTTTCTCTC TCCGTCCATA GGAGAACATC CGATCATGAT      60
CACTCCGATC AAACTAGCCT TTCTCTTATT ATTCATCACC ACAACAGCAA CCGCTGCACC     120
CAAAGCCAAA CGCAGGAACT ACCTTTTCAC ACCGCATGCA AAAGCAGTCG CGGAATATGC     180
ACTGTTGTCC TAACAAACAC AAGTCCATGC TGTAAAACCC TTAAACACGT TCCTACCGAT     240
GACCCTATCG AATTGATCCG AGCGTTAGCG GCTGCGACTG AATCTTCTGT GAAAAGAAGT     300
GTGGTTTTCC TCTCCGAGAT CAAACCAAAA CACAAATCAA ACGCAACCGC AGCTGCAGTG     360
GTCAACAGCT GCGAAAAAAA CTTGAAGTAC GCATTAGAAG ATTTCACTGA TTTTTGGAAC     420
GCTATGGGGA AGATGTAAA GACGTTGGCT CATAACTATT TCACGTGTAA AAGAAGTTA       480
ATGTCGATCA TGGGGTACCA TTGGACTTGT TTGGATGATA TTGATGATAA GAATCTGTTG     540
AAGGAANTGG AGACTGGGAT TAGTGTTGGG AAGAATCTAA GCAGTAATAC GTATGATGTG     600
TTTAATGGTT TGAAAACTAT TTTTAAGACG TTTGGTATCA AGGTGAAACT TAACGAGGAA     660
GACACTTCGC CCCAACCGCC ACCATTGTCG AATTATTACT ACTGATTAAA TGATTTGGAT     720
GTAATAAATA ATTAATATCA CTCGTATAAT GCCTAAAGCG ACCATATATG TACGATGTAT     780
GTTCTAGGTT TTATACATGT ACGGATGGAT TTCGAGATGA TTGGAAAGGA TATATTAATG     840
GAATGTGAGT TTTTTTATAA GTTTTTGAAT TGTCATCAAA ATGAAGCTGA AAGTATATAT     900
GTTGATTACA TAATTATTTG ATAGACCTTG ATAACTCGAA CAAATATACT ATCGCAATCA     960
TTATTGGTTA AATGTTTTCG GATACATGTC CTACGTCAAA CAAATAATT GTGCATTTTT     1020
CATATATTTG ATGCATGAAA GTTTCATATA TTTGATGATG AAACCATGCA TTTGTTTCCT    1080
TGTGCTCCCG GGACTTGTCA ACATTCAACG AACCTTCAGT AATCAACTAC ATATGATACT    1140
GATCTAGATG ATGTATGTAC ATGTACGACC ATGCATGAAT CACGCCGATG TTTCTTTTAT    1200
CAAGGCGATG TTTAAAATGT ACCCCGCTTT CTCGTTCTGG TAGGTATAAA TACGAGTGAA    1260
ATAACATTCC TATGTATAGT ATAGTAGTTC ATTTGTTGA CCAAAATTTA AATATATAGG     1320
ACATAATTAT ATTTCTCAA ATGAATTTGA GTTTTGAGTG CCTCCTGAAA AGATGATTCC     1380
AGCTTTCAAT TTTACAATGC TGGGTCAACC CCCCCAAGTA TTATCGTTAT AAAAAAAATAC   1440
TCAGAATAAT CTCACACCTA AAACTGCGCA TGAACTTGTT AATAGTCTAA AAAGATGTCC    1500
ATGAACTGAA TGAATAATAC CATTCATGTT TGAGTAACAC CATAGATGAC ACAATTTTCT   1560
TACTACCACT AATAGATGAC ACAATTGTCT TTGTTACATG TTGTAGTGTC CGATTAATTT   1620
GGGTTGAAGA AGATGAGAAC TCTCGATGAG AAGCTTTAGA ACATGCATT TACTTTCGTT     1680
ACTTTCGAAA TTCGGATGTA AAACTAGTAC TAGGAATGAA AATCCCAAAA TAAGTTGTTT    1740
ATTCTCTCTA ATCCTAAAAT TAATAAAATT ATAATAGACT AACTTTTCCA TCCTTAAGTT    1800
ACTTCTTATT TTTAGTAATC GAAGCTACAC CTCTTGATCA GGACAAAGAC ATAATCAAAT    1860
CATCTTGTGG TGAATAATTT TTAATCTCAA ATCCAATATT TGATTAGAGA AGTTTCAGCC   1920
ATTCAACTAC CTAAAATGTC TCCCTCCATG CAAAGCTCAT GCGAACCTAA TTTTAGAAAC    1980
TACAACTTCT ATAAGAATCT CCCATAATGC ACCATAATCT CCACCAGCCC CCATTAAATA    2040
ATCCACCGGG TCTGAATAAA TAAAAATAAG TCCCCTCCCT CTCCTATTTA CCTCCTAAAT    2100
```

| | | | | | | | | | | | | | | | | |
|---|---|---|---|---|---|---|---|---|---|---|---|---|---|---|---|---|
| AAAACCTGAG | GGAGAAAAAA | CAAAAAAAAA | ACAAAAAAAT | AGATTAAAAA | ATAAATA | | | | | | | | | | | 2157 |

| | | | | | | | | | | | | | | | | |
|---|---|---|---|---|---|---|---|---|---|---|---|---|---|---|---|---|
| ATG | GCG | GTC | GGG | AAA | ATT | GTG | ATA | TCA | GTG | GCA | TCC | ATG | CTT | CTA | GTG | 2205 |
| Met 1 | Ala | Val | Gly | Lys 5 | Ile | Val | Ile | Ser | Val 10 | Ala | Ser | Met | Leu | Leu 15 | Val | |
| GTG | GGT | GTT | GCC | ATA | GGA | GTT | GTC | ACC | TTT | GTT | AAT | AAA | GGT | GGT | GGT | 2253 |
| Val | Gly | Val | Ala 20 | Ile | Gly | Val | Val | Thr 25 | Phe | Val | Asn | Lys | Gly 30 | Gly | Gly | |
| GCA | GGT | GGC | GAC | AAG | ACT | CTG | AAC | TCG | CAT | CAG | AAA | GCG | GTT | GAG | TCA | 2301 |
| Ala | Gly | Gly 35 | Asp | Lys | Thr | Leu | Asn 40 | Ser | His | Gln | Lys | Ala 45 | Val | Glu | Ser | |
| CTT | TGT | GCG | TCA | GCC | ACA | GAC | AAA | GGT | TCA | TGC | GCA | AAA | ACA | CTT | GAC | 2349 |
| Leu | Cys 50 | Ala | Ser | Ala | Thr | Asp 55 | Lys | Gly | Ser | Cys | Ala 60 | Lys | Thr | Leu | Asp | |
| CCA | GTC | AAA | AGC | GAC | GAT | CCA | AGT | AAA | CTT | ATC | AAA | GCC | TTC | ATG | TTA | 2397 |
| Pro 65 | Val | Lys | Ser | Asp | Asp 70 | Pro | Ser | Lys | Leu | Ile 75 | Lys | Ala | Phe | Met | Leu 80 | |
| GCT | ACA | AAA | GAT | GCT | GTC | ACA | AAA | TCC | ACA | AAC | TTC | ACG | GCT | TCA | ACC | 2445 |
| Ala | Thr | Lys | Asp | Ala 85 | Val | Thr | Lys | Ser | Thr 90 | Asn | Phe | Thr | Ala | Ser 95 | Thr | |
| GAA | GAA | GGT | ATG | GGG | AAA | AAC | ATT | AAC | GCG | ACG | AGC | AAA | GCC | GTT | CTT | 2493 |
| Glu | Glu | Gly | Met 100 | Gly | Lys | Asn | Ile | Asn 105 | Ala | Thr | Ser | Lys | Ala 110 | Val | Leu | |
| GAT | TAC | TGC | AAG | AGA | GTG | CTG | ATG | TAC | GCT | CTC | GAG | GAT | CTT | GAG | ACC | 2541 |
| Asp | Tyr | Cys 115 | Lys | Arg | Val | Leu | Met 120 | Tyr | Ala | Leu | Glu | Asp 125 | Leu | Glu | Thr | |
| ATT | GTT | GAA | GAA | ATG | GGT | GAA | GAT | CTT | CAG | CAG | AGT | GGG | AGT | AAG | ATG | 2589 |
| Ile | Val 130 | Glu | Glu | Met | Gly 135 | Glu | Asp | Leu | Gln | Gln 140 | Ser | Gly | Ser | Lys | Met | |
| GAC | CAG | CTT | AAA | CAA | TGG | TTA | ACC | GGA | GTT | TTT | AAT | TAC | CAA | ACC | GAT | 2637 |
| Asp 145 | Gln | Leu | Lys | Gln | Trp 150 | Leu | Thr | Gly | Val | Phe 155 | Asn | Tyr | Gln | Thr | Asp 160 | |
| TGT | ATT | GAT | GAT | ATT | GAA | GAA | TCG | GAA | CTA | AGA | AAA | GTC | ATG | GGC | GAA | 2685 |
| Cys | Ile | Asp | Asp | Ile 165 | Glu | Glu | Ser | Glu | Leu 170 | Arg | Lys | Val | Met | Gly 175 | Glu | |
| GGA | ATC | GCT | CAC | TCC | AAG | ATT | TTG | TCC | AGT | AAC | GCT | ATC | GAT | ATC | TTC | 2733 |
| Gly | Ile | Ala | His 180 | Ser | Lys | Ile | Leu | Ser 185 | Ser | Asn | Ala | Ile | Asp 190 | Ile | Phe | |
| CAT | GCT | CTA | ACC | ACC | GCA | ATG | TCC | CAA | ATG | AAT | GTT | AAG | GTC | GAT | GAC | 2781 |
| His | Ala | Leu | Thr 195 | Thr | Ala | Met | Ser | Gln 200 | Met | Asn | Val | Lys | Val 205 | Asp | Asp | |
| ATG | AAG | AAA | GGG | AAC | CTC | GGA | GAA | ACT | CCA | GCT | CCT | GAT | CGT | GAT | CTT | 2829 |
| Met | Lys | Lys | Gly | Asn 210 | Leu | Gly | Glu | Thr | Pro 215 | Ala | Pro | Asp | Arg | Asp 220 | Leu | |
| CTT | GAA | GAC | TTG | GAC | CAA | AAA | GGA | TTA | CCT | AAA | TGG | CAT | TCT | GAC | AAA | 2877 |
| Leu 225 | Glu | Asp | Leu | Asp | Gln 230 | Lys | Gly | Leu | Pro | Lys 235 | Trp | His | Ser | Asp | Lys 240 | |
| GAC | AGG | AAG | CTT | ATG | GCT | CAG | GCC | GGA | CGC | CCT | GGT | GCA | CCT | GCT | GAT | 2925 |
| Asp | Arg | Lys | Leu | Met 245 | Ala | Gln | Ala | Gly | Arg 250 | Pro | Gly | Ala | Pro | Ala 255 | Asp | |
| GAA | GGT | ATC | GGT | GAA | GGC | GGT | GGT | GGC | GGT | AAG | ATC | AAG | CCG | ACT | | 2973 |
| Glu | Gly | Ile | Gly | Glu 260 | Gly | Gly | Gly | Gly | Gly 265 | Lys | Ile | Lys | Pro | Thr 270 | | |
| CAT | GTG | GTG | GCT | AAG | GAC | GGA | AGT | GGA | CAG | TTT | AAG | ACG | ATT | TCT | GAG | 3021 |
| His | Val | Val | Ala | Lys 275 | Asp | Gly | Ser | Gly | Gln 280 | Phe | Lys | Thr | Ile | Ser 285 | Glu | |
| GCG | GTT | AAA | GCT | TGT | CCG | GAG | AAA | AAT | CCT | GGA | CGT | TGC | ATT | ATC | TAT | 3069 |
| Ala | Val | Lys | Ala 290 | Cys | Pro | Glu | Lys | Asn 295 | Pro | Gly | Arg | Cys | Ile 300 | Ile | Tyr | |
| ATT | AAG | GCT | GGT | GTC | TAC | AAG | GAA | CAA | GTC | ACT | ATC | CCT | AAG | AAG | GTA | 3117 |
| Ile | Lys | Ala | Gly | Val 305 | Tyr | Lys | Glu | Gln | Val 310 | Thr | Ile | Pro | Lys | Lys 315 | Val 320 | |

```
AAC AAC GTT TTC ATG TTT GGT GAT GGT GCA ACA CAG ACA ATC ATT ACT        3165
Asn Asn Val Phe Met Phe Gly Asp Gly Ala Thr Gln Thr Ile Ile Thr
            325             330                 335

TTT GAC AGA AGT GTT GGT CTT AGC CCT GGA ACC ACT ACT TCA CTC AGT        3213
Phe Asp Arg Ser Val Gly Leu Ser Pro Gly Thr Thr Thr Ser Leu Ser
            340             345                 350

GGC ACC GTT CGT AAGTCTCATT TAATTAATCT TGTCTTTAAT TTTTCCTATC            3265
Gly Thr Val Arg
        355

TAAACTAAAT TGCACCGTGC AATATCTAAA TATACGTTGG TATCTAAATA TACACATGCA      3325

CGTTGATATC TAATCATATA CATGCATGCA TGCAGAGGTT GAATCTGAGG GATTCATGGC      3385

GAAATGGATC GGGTTTCAGA ACACTGCTGG TCCATTAGGA CACCAAGCTG TCGCGTTCCG      3445

TGTGAACGGA GACCGTGCGG TCATATTCAA CTGCAGATTT GACGGTTACC AAGACACGCT      3505

CTACGTCAAC AACGGACGTC AGTTCTACAG GAACATTGTT GTATCCGGTA CAGTCGATTT      3565

CATCTTCGGA AAATCTGCGA CCGTGATTCA AAACTCTCTA ATCCTCTGCC GAAAGGGAAG      3625

CCCCGGACAA ACCAACCACG TCACAGCCGA CGGTAAC GAG AAG GGT AAA GCG GTG      3680
                                          Glu Lys Gly Lys Ala Val
                                                          360

AAG ATT GGT ATC GTT CTC CAT AAC TGC CGT ATC ATG GCG GAC AAA GAG        3728
Lys Ile Gly Ile Val Leu His Asn Cys Arg Ile Met Ala Asp Lys Glu
            365             370                 375

CTC GAA GCT GAC AGG CTA ACC GTC AAA TCA TAC CTT GGA CGG CCG TGG        3776
Leu Glu Ala Asp Arg Leu Thr Val Lys Ser Tyr Leu Gly Arg Pro Trp
        380                 385                 390

AAA CCA TTT GCC ACC ACC GCA GTT ATC GGA ACT GAG ATT GGC GAT TTG        3824
Lys Pro Phe Ala Thr Thr Ala Val Ile Gly Thr Glu Ile Gly Asp Leu
395             400                 405                 410

ATT CAA CCG ACA GGA TGG AAC GAA TGG CAA GGA GAA AAA TTC CAT TTG        3872
Ile Gln Pro Thr Gly Trp Asn Glu Trp Gln Gly Glu Lys Phe His Leu
            415                 420                 425

ACA GCT ACA TAT GTT GAG TTC AAT AAC CGT GGA CCA GGA GCT AAC ACT        3920
Thr Ala Thr Tyr Val Glu Phe Asn Asn Arg Gly Pro Gly Ala Asn Thr
            430                 435                 440

GCT GCG AGG GTT CCT TGG GCT AAG ATG GCT AAG TCT GCT GCT GAG GTT        3968
Ala Ala Arg Val Pro Trp Ala Lys Met Ala Lys Ser Ala Ala Glu Val
            445             450                 455

GAA CGT TTC ACC GTC GCT AAC TGG TTG ACT CCT GCT AAC TGG ATT CAA        4016
Glu Arg Phe Thr Val Ala Asn Trp Leu Thr Pro Ala Asn Trp Ile Gln
        460                 465                 470

GAA GCC AAC GTT CCT GTC CAG CTT GGA TTA TAAGAAAACT AACTAACAAA          4066
Glu Ala Asn Val Pro Val Gln Leu Gly Leu
475             480

ATATATAACG AATAATATAT AGTATGTGAT CATGTAAAAA GGTAACGATA CGACCTCGTC      4126

TCTCGGGATC AGGGCTCTTT TTGGTTATTA TTAGGGTTCT AGGCGTTTTG GGATGATGTT      4186

TGTATAAGAT TGCTTTTGTT TCACATGCAA AACATATATA CAAAATATCT TATTTCTTCT      4246

TTTACTTTCT TTTATTCAAA ATAATGAGTT TTTATAACCA TGTTGATCTC TATATTATAG      4306

ACATCCTATC CCTAAACATG ATAAATATAA CTTCAAACTA ATACCCTAGT AAAAATATAT      4366

AAACAAAAAA ATACTTATGT AAGATTATGT GCAAGCATGG CTCAACAAAT ATAACTTTAT      4426

AAAAGTTTG CATTATTGCT ATGTTTATAT ATGATTGCTA TATGTAAGTA TGTTGATAGA       4486

AGTTTATGAG GACAGAGATG ACTATTGGCA AATATTAATG AGAAGTGTGA TATGTTATCA      4546

TTTATCAAAA CAAAGCAAGC CCTATATTAC CAAATCAAAT CTCACTTCAA AGCGAAGCTG      4606

CCCATTGATG ATCTCACCAA TATTTCACAC ATTACAAACG TGACATTATC TTCTCTTCTA      4666

TGGCTGTTTC CTTAACCAAA GTAAACAGAG TCCAAATCCA ACCTTCCAAA CCAACCCCAT      4726
```

```
TCATCTTATT GGGATCTGTC CTTGATCGAT AACATTCCGG TTTTAAGATG TTTCGCAAGG    4786

ACAATACATC TCTTTACGCA TGGACCTGAT GCTGCTAGTA GAGTCATAAA AGATGCATCG    4846

GCTAAAGCAG TTGTCCCTTA CTATCAATTG TTAAAGATCC TAAGGTGCTG CTATTGGATG    4906

AAGCAACAAG TTCCCTAGAC GCCTAATCGG ACTATGTGGT CCAAGATTCA CTGGACCGGG    4966

TTATGGTTGA C                                                        4977
```

( 2 ) INFORMATION FOR SEQ ID NO:8:

( i ) SEQUENCE CHARACTERISTICS:
        ( A ) LENGTH: 484 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Ala Val Gly Lys Ile Val Ile Ser Val Ala Ser Met Leu Leu Val
 1               5                  10                  15

Val Gly Val Ala Ile Gly Val Val Thr Phe Val Asn Lys Gly Gly Gly
                20                  25                  30

Ala Gly Gly Asp Lys Thr Leu Asn Ser His Gln Lys Ala Val Glu Ser
            35                  40                  45

Leu Cys Ala Ser Ala Thr Asp Lys Gly Ser Cys Ala Lys Thr Leu Asp
50                  55                  60

Pro Val Lys Ser Asp Asp Pro Ser Lys Leu Ile Lys Ala Phe Met Leu
65                  70                  75                  80

Ala Thr Lys Asp Ala Val Thr Lys Ser Thr Asn Phe Thr Ala Ser Thr
                85                  90                  95

Glu Glu Gly Met Gly Lys Asn Ile Asn Ala Thr Ser Lys Ala Val Leu
            100                 105                 110

Asp Tyr Cys Lys Arg Val Leu Met Tyr Ala Leu Glu Asp Leu Glu Thr
        115                 120                 125

Ile Val Glu Glu Met Gly Glu Asp Leu Gln Gln Ser Gly Ser Lys Met
130                 135                 140

Asp Gln Leu Lys Gln Trp Leu Thr Gly Val Phe Asn Tyr Gln Thr Asp
145                 150                 155                 160

Cys Ile Asp Asp Ile Glu Glu Ser Glu Leu Arg Lys Val Met Gly Glu
                165                 170                 175

Gly Ile Ala His Ser Lys Ile Leu Ser Ser Asn Ala Ile Asp Ile Phe
            180                 185                 190

His Ala Leu Thr Thr Ala Met Ser Gln Met Asn Val Lys Val Asp Asp
        195                 200                 205

Met Lys Lys Gly Asn Leu Gly Glu Thr Pro Ala Pro Asp Arg Asp Leu
210                 215                 220

Leu Glu Asp Leu Asp Gln Lys Gly Leu Pro Lys Trp His Ser Asp Lys
225                 230                 235                 240

Asp Arg Lys Leu Met Ala Gln Ala Gly Arg Pro Gly Ala Pro Ala Asp
                245                 250                 255

Glu Gly Ile Gly Glu Gly Gly Gly Gly Gly Lys Ile Lys Pro Thr
            260                 265                 270

His Val Val Ala Lys Asp Gly Ser Gly Gln Phe Lys Thr Ile Ser Glu
        275                 280                 285

Ala Val Lys Ala Cys Pro Glu Lys Asn Pro Gly Arg Cys Ile Ile Tyr
290                 295                 300

Ile Lys Ala Gly Val Tyr Lys Glu Gln Val Thr Ile Pro Lys Lys Val
305                 310                 315                 320
```

| | | | | | | | | | | | | | |
|---|---|---|---|---|---|---|---|---|---|---|---|---|---|
| Asn | Asn | Val | Phe | Met 325 | Phe | Gly | Asp | Gly | Ala 330 | Thr | Gln | Thr | Ile | Ile 335 | Thr |
| Phe | Asp | Arg | Ser 340 | Val | Gly | Leu | Ser | Pro 345 | Gly | Thr | Thr | Thr | Ser 350 | Leu | Ser |
| Gly | Thr | Val 355 | Arg | Glu | Lys | Gly | Lys 360 | Ala | Val | Lys | Ile | Gly 365 | Ile | Val | Leu |
| His | Asn 370 | Cys | Arg | Ile | Met | Ala 375 | Asp | Lys | Glu | Leu | Glu 380 | Ala | Asp | Arg | Leu |
| Thr 385 | Val | Lys | Ser | Tyr | Leu 390 | Gly | Arg | Pro | Trp | Lys 395 | Pro | Phe | Ala | Thr | Thr 400 |
| Ala | Val | Ile | Gly | Thr 405 | Glu | Ile | Gly | Asp | Leu 410 | Ile | Gln | Pro | Thr | Gly 415 | Trp |
| Asn | Glu | Trp | Gln 420 | Gly | Glu | Lys | Phe | His 425 | Leu | Thr | Ala | Thr | Tyr 430 | Val | Glu |
| Phe | Asn | Asn 435 | Arg | Gly | Pro | Gly | Ala 440 | Asn | Thr | Ala | Ala | Arg 445 | Val | Pro | Trp |
| Ala | Lys 450 | Met | Ala | Lys | Ser | Ala 455 | Ala | Glu | Val | Glu | Arg 460 | Phe | Thr | Val | Ala |
| Asn 465 | Trp | Leu | Thr | Pro | Ala 470 | Asn | Trp | Ile | Gln | Glu 475 | Ala | Asn | Val | Pro | Val 480 |
| Gln | Leu | Gly | Leu | | | | | | | | | | | | |

( 2 ) INFORMATION FOR SEQ ID NO:9:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

TATGTTTTAA AA                                                              12

( 2 ) INFORMATION FOR SEQ ID NO:10:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

TATGTTTAAA A                                                              11